US007700100B2

(12) United States Patent
Johnson et al.

(10) Patent No.: US 7,700,100 B2
(45) Date of Patent: Apr. 20, 2010

(54) FCγRIIB FUSION PROTEINS AND COMPOSITIONS THEREOF

(75) Inventors: Leslie S. Johnson, Darnstown, MD (US); Hua Li, Gaithersburg, MD (US); Nadine Tuaillon, Gettysburg, PA (US)

(73) Assignee: Macrogenics, Inc., Rockville, MD (US)

( * ) Notice: Subject to any disclaimer, the term of this patent is extended or adjusted under 35 U.S.C. 154(b) by 1761 days.

(21) Appl. No.: 10/756,153

(22) Filed: Jan. 13, 2004

(65) Prior Publication Data

US 2004/0265321 A1 Dec. 30, 2004

Related U.S. Application Data

(60) Provisional application No. 60/439,709, filed on Jan. 13, 2003.

(51) Int. Cl.
*A61K 39/395* (2006.01)

(52) U.S. Cl. .............. 424/134.1; 424/144.1; 424/185.1; 424/192.1

(58) Field of Classification Search ........................ None
See application file for complete search history.

(56) References Cited

U.S. PATENT DOCUMENTS

| | | | |
|---|---|---|---|
| 5,116,964 A | 5/1992 | Capon et al. | |
| 5,155,027 A | 10/1992 | Sledziewski et al. | |
| 5,219,728 A | 6/1993 | Khayat et al. | |
| 5,428,130 A | 6/1995 | Capon et al. | |
| 5,451,669 A | 9/1995 | McKenzie et al. | |
| 5,641,863 A | 6/1997 | Schreiber et al. | |
| 5,767,077 A | 6/1998 | Peltz et al. | |
| 5,817,767 A * | 10/1998 | Allaway et al. | 530/387.3 |
| 5,976,831 A | 11/1999 | Peltz et al. | |
| 5,985,599 A | 11/1999 | McKenzie et al. | |
| 5,998,166 A | 12/1999 | Luo | |
| 6,034,223 A * | 3/2000 | Maddon et al. | 530/391.7 |
| 6,294,347 B1 | 9/2001 | Peltz et al. | |
| 6,444,789 B1 | 9/2002 | Luo | |
| 6,737,056 B1 * | 5/2004 | Presta | 424/133.1 |
| 6,911,321 B2 * | 6/2005 | Presta et al. | 435/69.1 |

FOREIGN PATENT DOCUMENTS

| | | |
|---|---|---|
| EP | 0 131 142 | 1/1985 |
| EP | 0 319 307 | 6/1989 |
| EP | 0 343 950 B1 | 11/1989 |
| EP | 0791 653 A1 | 8/1997 |
| EP | 1 006 183 A1 | 6/2000 |
| WO | WO 88/03172 | 5/1988 |
| WO | WO 91/06570 | 5/1991 |
| WO | WO 96/34953 | 11/1996 |
| WO | WO 99/40117 | 8/1999 |
| WO | WO 00/32767 | 6/2000 |

OTHER PUBLICATIONS

Ashkenazi et al., Curr Opin Immunol, 1997, 9:195-200.*
Skolnick et al., Trends in Biotechnology, 18(1):34-39, 2000.*
Whisstock et al., Quarterly Reviews of Biophysics, 2003, 36:307-340.*
Durand et al., Eur J Immunol. Jul. 2001;31(7):1952-61.*
Schiller et al., Eur J Immunol. Feb. 2000;30(2):481-90.*
Rankin et al., Blood. Oct. 1, 2006;108(7):2384-91. Epub Jun. 6, 2006.*
Samuelsson et al., Science. Jan. 19, 2001;291(5503):445-6.*
Bouhlal et al., "Soluble CD16 Inhibits CR3 (CD11b/CD18)-Mediated Infection of Monocytes/Macrophages by Opsonized Primary R5 HIV-11," *Journal of Immunology*, 166: 3377-3383, 2001.
Galon et al., "Identification of the cleavage site involved in production of plasma soluble Fc gamma receptor type III (CD16)," *European Journal of Immunology*, 28(7): 2101-2107, 1998.
Gavin et al., "Recombinant soluble Fc gamma RII inhibits immune complex precipitation," *Clinical Experimental Immunology*, 102(3): 620-625, 1995.
Hibbs et al., "Membrane-Proximal Ig-like Domain of FcγRIII (CD16) Contains Residues Critical for Ligand Binding," *Journal of Immunology*, 152(9): 4466-4474, 1994.
Hoover et al., "Autoregulatory Circuits in Myeloma Tumor Cell Cytotoxicity Mediated by Soluble CD16," *Journal of Clinical Investigation*, 95(1): 241-247, 1995.
Ierino et al., "Recombinant Soluble Human FcγRII: Production, Characterization, and Inhibition of the Arthus Reaction," *Journal of Experimental Medicine*, 178: 1617-1628, 1993.
Li et al., "Recombinant CD16A-Ig forms a homodimer and cross-blocks the ligand binding functions of neutrophil and monocyte Fcγ receptors," *Molecular Immunology*, 38: 527-538, 2001.
Simpson et al., "Soluble FcR Block Suppressor T Cell Activity at Low Concentration in Vitro Allowing Isotype-Specific Antibody Production," *Cellular Immunology*, 167(1): 122-128, 1996.
Tamm A et al: "The binding epitopes of human CD16 (FcgammaRIII) monoclonal antibodies" Journal of Immunology, vol. 157, 1996, pp. 1576-1581.
Soubrane C et al: "Biologic Response to Anti-CD16 Monoclonal Antibody Therapy in a Human Immunodeficiency Virus-Related Immune Thrombocytopenic Purpura Patient" Blood, vol. 81, No. 1, Jan. 1993, pp. 15-19.

(Continued)

*Primary Examiner*—Michael Szperka
(74) *Attorney, Agent, or Firm*—Margaret B. Brivanlou; King & Spalding LLP

(57) ABSTRACT

The present invention relates to molecules, preferably soluble (i.e., not membrane bound) polypeptides, most preferably soluble fusion polypeptides comprising the extracellular soluble regions of FcγRIIB, derivatives and analogs thereof, and nucleic acids encoding same. Molecules of the invention are particularly useful for the treatment, management, or prevention of, or amelioration of one or more symptoms of, an autoimmune disease, especially for ameliorating serum platelet deficiency associated with immune thrombocytopenic purpura. The invention provides methods and compositions for enhancing the therapeutic efficacy of standard, current or experimental therapies for an autoimmune disease by administering a molecule of the invention.

4 Claims, 16 Drawing Sheets

OTHER PUBLICATIONS

Figure 1:
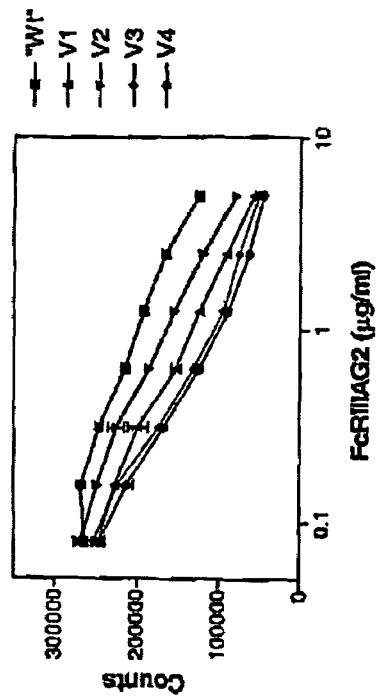
Figure 1:
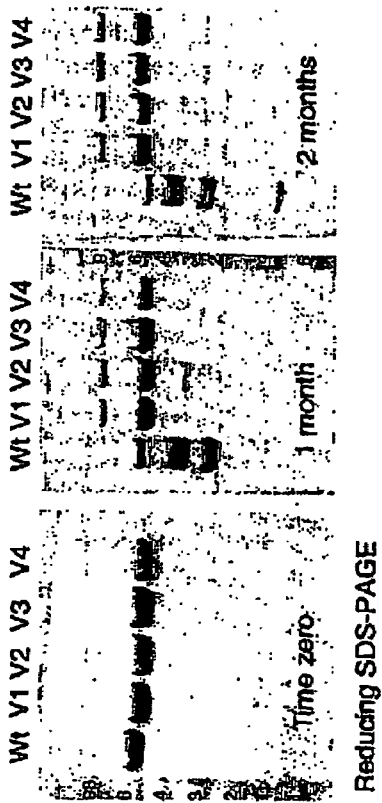

Mandelboim Ofer et al: "Human CD16 as a lysis receptor mediating direct natural killer cell cytotoxicity" Proceedings of the National Academy of Sciences of USA, National Academy of Science, vol. 96, No. 10, May 11, 1999, pp. 5640-5644.

Radaev S et al: "The Structure of a Human Type III Fc[gamma] Receptor in Complex with Fc" Journal of Biological Chemistry, American Society of Biolochemical Biologists, vol. 276, No. 19, Jan. 31, 2001, pp. 16469-16477.

EP Search Report Dated Sep. 25, 2007.

* cited by examiner

A.

B.

C.

A.

B.

SEQUENCE LISTING

```
<160> NUMBER OF SEQ ID NOS: 54

<210> SEQ ID NO 1
<211> LENGTH: 420
<212> TYPE: PRT
<213> ORGANISM: Homo sapiens
<220> FEATURE:
<223> OTHER INFORMATION: sFcRIIIa-G2

<400> SEQUENCE: 1

Met Arg Thr Glu Asp Leu Pro Lys Ala Val Val Phe Leu Glu Pro Gln
1               5                   10                  15

Trp Tyr Arg Val Leu Glu Lys Asp Ser Val Thr Leu Lys Cys Gln Gly
            20                  25                  30

Ala Tyr Ser Pro Glu Asp Asn Ser Thr Gln Trp Phe His Asn Glu Ser
        35                  40                  45

Leu Ile Ser Ser Gln Ala Ser Ser Tyr Phe Ile Asp Ala Ala Thr Val
    50                  55                  60

Asp Asp Ser Gly Glu Tyr Arg Cys Gln Thr Asn Leu Ser Thr Leu Ser
65                  70                  75                  80

Asp Pro Val Gln Leu Glu Val His Ile Gly Trp Leu Leu Leu Gln Ala
                85                  90                  95

Pro Arg Trp Val Phe Lys Glu Glu Asp Pro Ile His Leu Arg Cys His
```

-continued

```
                100                 105                 110
Ser Trp Lys Asn Thr Ala Leu His Lys Val Thr Tyr Leu Gln Asn Gly
            115                 120                 125

Lys Gly Arg Lys Tyr Phe His His Asn Ser Asp Phe Tyr Ile Pro Lys
        130                 135                 140

Ala Thr Leu Lys Asp Ser Gly Ser Tyr Phe Cys Arg Gly Leu Val Gly
145                 150                 155                 160

Ser Lys Asn Val Ser Ser Glu Thr Val Asn Ile Thr Ile Thr Gln Gly
                165                 170                 175

Leu Ala Val Ser Thr Ile Ser Ser Phe Phe Pro Pro Gly Tyr Gln Val
            180                 185                 190

Glu Arg Lys Cys Cys Val Glu Cys Pro Pro Cys Pro Ala Pro Pro Val
        195                 200                 205

Ala Gly Pro Ser Val Phe Leu Phe Pro Pro Lys Pro Lys Asp Thr Leu
210                 215                 220

Met Ile Ser Arg Thr Pro Glu Val Thr Cys Val Val Val Asp Val Ser
225                 230                 235                 240

His Glu Asp Pro Glu Val Gln Phe Asn Trp Tyr Val Asp Gly Met Glu
                245                 250                 255

Val His Asn Ala Lys Thr Lys Pro Arg Glu Glu Gln Phe Asn Ser Thr
            260                 265                 270

Phe Arg Val Val Ser Val Leu Thr Val Val His Gln Asp Trp Leu Asn
        275                 280                 285

Gly Lys Glu Tyr Lys Cys Lys Val Ser Asn Lys Gly Leu Pro Ala Pro
290                 295                 300

Ile Glu Lys Thr Ile Ser Lys Thr Lys Gly Gln Pro Arg Glu Pro Gln
305                 310                 315                 320

Val Tyr Thr Leu Pro Pro Ser Arg Glu Glu Met Thr Lys Asn Gln Val
                325                 330                 335

Ser Leu Thr Cys Leu Val Lys Gly Phe Tyr Pro Ser Asp Ile Ala Val
            340                 345                 350

Glu Trp Glu Ser Asn Gly Gln Pro Glu Asn Asn Tyr Lys Thr Thr Pro
        355                 360                 365

Pro Met Leu Asp Ser Asp Gly Ser Phe Phe Leu Tyr Ser Lys Leu Thr
370                 375                 380

Val Asp Lys Ser Arg Trp Gln Gln Gly Asn Val Phe Ser Cys Ser Val
385                 390                 395                 400

Met His Glu Ala Leu His Asn His Tyr Thr Gln Lys Ser Leu Ser Leu
                405                 410                 415

Ser Pro Gly Lys
            420
```

<210> SEQ ID NO 2
<211> LENGTH: 409
<212> TYPE: PRT
<213> ORGANISM: Homo sapiens
<220> FEATURE:
<223> OTHER INFORMATION: sFcRIIb-G2

<400> SEQUENCE: 2

```
Thr Pro Ala Ala Pro Pro Lys Ala Val Leu Lys Leu Glu Pro Gln Trp
1               5                   10                  15

Ile Asn Val Leu Gln Glu Asp Ser Val Thr Leu Thr Cys Arg Gly Thr
            20                  25                  30

His Ser Pro Glu Ser Asp Ser Ile Gln Trp Phe His Asn Gly Asn Leu
```

```
                35                  40                  45
Ile Pro Thr His Thr Gln Pro Ser Tyr Arg Phe Lys Ala Asn Asn Asn
 50                      55                  60

Asp Ser Gly Glu Tyr Thr Cys Gln Thr Gly Gln Thr Ser Leu Ser Asp
 65                  70                  75                  80

Pro Val His Leu Thr Val Leu Ser Glu Trp Leu Val Leu Gln Thr Pro
                     85                  90                  95

His Leu Glu Phe Gln Glu Gly Glu Thr Ile Val Leu Arg Cys His Ser
                100                 105                 110

Trp Lys Asp Lys Pro Leu Val Lys Val Thr Phe Phe Gln Asn Gly Lys
                115                 120                 125

Ser Lys Lys Phe Ser Arg Ser Asp Pro Asn Phe Ser Ile Pro Gln Ala
130                 135                 140

Asn His Ser His Ser Gly Asp Tyr His Cys Thr Gly Asn Ile Gly Tyr
145                 150                 155                 160

Thr Leu Phe Ser Ser Lys Pro Val Thr Ile Thr Val Gln Ala Pro Ser
                165                 170                 175

Ser Ser Pro Met Glu Glu Arg Lys Cys Cys Val Glu Cys Pro Pro Cys
                180                 185                 190

Pro Ala Pro Pro Val Ala Gly Pro Ser Val Phe Leu Phe Pro Pro Lys
                195                 200                 205

Pro Lys Asp Thr Leu Met Ile Ser Arg Thr Pro Glu Val Thr Cys Val
210                 215                 220

Val Val Asp Val Ser His Glu Asp Pro Glu Val Gln Phe Asn Trp Tyr
225                 230                 235                 240

Val Asp Gly Met Glu Val His Asn Ala Lys Thr Lys Pro Arg Glu Glu
                245                 250                 255

Gln Phe Asn Ser Thr Phe Arg Val Val Ser Val Leu Thr Val Val His
                260                 265                 270

Gln Asp Trp Leu Asn Gly Lys Glu Tyr Lys Cys Lys Val Ser Asn Lys
                275                 280                 285

Gly Leu Pro Ala Pro Ile Glu Lys Thr Ile Ser Lys Thr Lys Gly Gln
290                 295                 300

Pro Arg Glu Pro Gln Val Tyr Thr Leu Pro Pro Ser Arg Glu Glu Met
305                 310                 315                 320

Thr Lys Asn Gln Val Ser Leu Thr Cys Leu Val Lys Gly Phe Tyr Pro
                325                 330                 335

Ser Asp Ile Ala Val Glu Trp Glu Ser Asn Gly Gln Pro Glu Asn Asn
                340                 345                 350

Tyr Lys Thr Thr Pro Pro Met Leu Asp Ser Asp Gly Ser Phe Phe Leu
                355                 360                 365

Tyr Ser Lys Leu Thr Val Asp Lys Ser Arg Trp Gln Gln Gly Asn Val
370                 375                 380

Phe Ser Cys Ser Val Met His Glu Ala Leu His Asn His Tyr Thr Gln
385                 390                 395                 400

Lys Ser Leu Ser Leu Ser Pro Gly Lys
                405

<210> SEQ ID NO 3
<211> LENGTH: 409
<212> TYPE: PRT
<213> ORGANISM: Homo sapiens
<220> FEATURE:
<223> OTHER INFORMATION: sFcRIIa(131R)-G2
```

<400> SEQUENCE: 3

```
Ala Pro Pro Lys Ala Val Leu Lys Leu Glu Pro Trp Ile Asn Val
 1               5                  10                  15

Leu Gln Glu Asp Ser Val Thr Leu Thr Cys Gln Gly Ala Arg Ser Pro
             20                  25                  30

Glu Ser Asp Ser Ile Gln Trp Phe His Asn Gly Asn Leu Ile Pro Thr
             35                  40                  45

His Thr Gln Pro Ser Tyr Arg Phe Lys Ala Asn Asn Asn Asp Ser Gly
 50                  55                  60

Glu Tyr Thr Cys Gln Thr Gly Gln Thr Ser Leu Ser Asp Pro Val His
 65                  70                  75                  80

Leu Thr Val Leu Ser Glu Trp Leu Val Leu Gln Thr Pro His Leu Glu
                 85                  90                  95

Phe Gln Glu Gly Glu Thr Ile Met Leu Arg Cys His Ser Trp Lys Asp
                100                 105                 110

Lys Pro Leu Val Lys Val Thr Phe Phe Gln Asn Gly Lys Ser Gln Lys
             115                 120                 125

Phe Ser Arg Leu Asp Pro Thr Phe Ser Ile Pro Gln Ala Asn His Ser
             130                 135                 140

His Ser Gly Asp Tyr His Cys Thr Gly Asn Ile Gly Tyr Thr Leu Phe
145                 150                 155                 160

Ser Ser Lys Pro Val Thr Ile Thr Val Gln Val Pro Ser Met Gly Ser
                 165                 170                 175

Ser Ser Pro Met Glu Glu Arg Lys Cys Cys Val Glu Cys Pro Pro Cys
             180                 185                 190

Pro Ala Pro Pro Val Ala Gly Pro Ser Val Phe Leu Phe Pro Pro Lys
             195                 200                 205

Pro Lys Asp Thr Leu Met Ile Ser Arg Thr Pro Glu Val Thr Cys Val
             210                 215                 220

Val Val Asp Val Ser His Glu Asp Pro Glu Val Gln Phe Asn Trp Tyr
225                 230                 235                 240

Val Asp Gly Met Glu Val His Asn Ala Lys Thr Lys Pro Arg Glu Glu
                 245                 250                 255

Gln Phe Asn Ser Thr Phe Arg Val Val Ser Val Leu Thr Val Val His
             260                 265                 270

Gln Asp Trp Leu Asn Gly Lys Glu Tyr Lys Cys Lys Val Ser Asn Lys
             275                 280                 285

Gly Leu Pro Ala Pro Ile Glu Lys Thr Ile Ser Lys Thr Lys Gly Gln
             290                 295                 300

Pro Arg Glu Pro Gln Val Tyr Thr Leu Pro Pro Ser Arg Glu Glu Met
305                 310                 315                 320

Thr Lys Asn Gln Val Ser Leu Thr Cys Leu Val Lys Gly Phe Tyr Pro
                 325                 330                 335

Ser Asp Ile Ala Val Glu Trp Glu Ser Asn Gly Gln Pro Glu Asn Asn
             340                 345                 350

Tyr Lys Thr Thr Pro Pro Met Leu Asp Ser Asp Gly Ser Phe Phe Leu
             355                 360                 365

Tyr Ser Lys Leu Thr Val Asp Lys Ser Arg Trp Gln Gln Gly Asn Val
             370                 375                 380

Phe Ser Cys Ser Val Met His Glu Ala Leu His Asn His Tyr Thr Gln
385                 390                 395                 400

Lys Ser Leu Ser Leu Ser Pro Gly Lys
                 405
```

```
<210> SEQ ID NO 4
<211> LENGTH: 409
<212> TYPE: PRT
<213> ORGANISM: Homo sapiens
<220> FEATURE:
<223> OTHER INFORMATION: sFcRIIa(131H)-G2

<400> SEQUENCE: 4

Ala Pro Pro Lys Ala Val Leu Lys Leu Glu Pro Pro Trp Ile Asn Val
 1               5                  10                  15

Leu Gln Glu Asp Ser Val Thr Leu Thr Cys Gln Gly Ala Arg Ser Pro
            20                  25                  30

Glu Ser Asp Ser Ile Gln Trp Phe His Asn Gly Asn Leu Ile Pro Thr
        35                  40                  45

His Thr Gln Pro Ser Tyr Arg Phe Lys Ala Asn Asn Asn Asp Ser Gly
 50                  55                  60

Glu Tyr Thr Cys Gln Thr Gly Gln Thr Ser Leu Ser Asp Pro Val His
65                  70                  75                  80

Leu Thr Val Leu Ser Glu Trp Leu Val Leu Gln Thr Pro His Leu Glu
                85                  90                  95

Phe Gln Glu Gly Glu Thr Ile Met Leu Arg Cys His Ser Trp Lys Asp
            100                 105                 110

Lys Pro Leu Val Lys Val Thr Phe Phe Gln Asn Gly Lys Ser Gln Lys
        115                 120                 125

Phe Ser His Leu Asp Pro Thr Phe Ser Ile Pro Gln Ala Asn His Ser
130                 135                 140

His Ser Gly Asp Tyr His Cys Thr Gly Asn Ile Gly Tyr Thr Leu Phe
145                 150                 155                 160

Ser Ser Lys Pro Val Thr Ile Thr Val Gln Val Pro Ser Met Gly Ser
                165                 170                 175

Ser Ser Pro Met Glu Glu Arg Lys Cys Cys Val Glu Cys Pro Pro Cys
            180                 185                 190

Pro Ala Pro Pro Val Ala Gly Pro Ser Val Phe Leu Phe Pro Pro Lys
        195                 200                 205

Pro Lys Asp Thr Leu Met Ile Ser Arg Thr Pro Glu Val Thr Cys Val
210                 215                 220

Val Val Asp Val Ser His Glu Asp Pro Glu Val Gln Phe Asn Trp Tyr
225                 230                 235                 240

Val Asp Gly Met Glu Val His Asn Ala Lys Thr Lys Pro Arg Glu Glu
                245                 250                 255

Gln Phe Asn Ser Thr Phe Arg Val Val Ser Val Leu Thr Val Val His
            260                 265                 270

Gln Asp Trp Leu Asn Gly Lys Glu Tyr Lys Cys Lys Val Ser Asn Lys
        275                 280                 285

Gly Leu Pro Ala Pro Ile Glu Lys Thr Ile Ser Lys Thr Lys Gly Gln
290                 295                 300

Pro Arg Glu Pro Gln Val Tyr Thr Leu Pro Pro Ser Arg Glu Glu Met
305                 310                 315                 320

Thr Lys Asn Gln Val Ser Leu Thr Cys Leu Val Lys Gly Phe Tyr Pro
                325                 330                 335

Ser Asp Ile Ala Val Glu Trp Glu Ser Asn Gly Gln Pro Glu Asn Asn
            340                 345                 350

Tyr Lys Thr Thr Pro Pro Met Leu Asp Ser Asp Gly Ser Phe Phe Leu
        355                 360                 365
```

```
Tyr Ser Lys Leu Thr Val Asp Lys Ser Arg Trp Gln Gln Gly Asn Val
    370                 375                 380

Phe Ser Cys Ser Val Met His Glu Ala Leu His Asn His Tyr Thr Gln
385                 390                 395                 400

Lys Ser Leu Ser Leu Ser Pro Gly Lys
                405

<210> SEQ ID NO 5
<211> LENGTH: 1382
<212> TYPE: DNA
<213> ORGANISM: Homo sapiens
<220> FEATURE:
<223> OTHER INFORMATION: sFcRIIB insert with signal sequence

<400> SEQUENCE: 5
gctagccacc atgggaatcc tgtcattctt acctgtcctt gccactgaga gtgactgggc      60
tgactgcaag tcccccagc cttggggtca tatgcttctg tggacagctg tgctattcct     120
ggctcctgtt gctgggacac ctgcagctcc ccaaaggct gtgctgaaac tcgagcccca     180
gtggatcaac gtgctccagg aggactctgt gactctgaca tgccggggga ctcacagccc     240
tgagagcgac tccattcagt ggttccacaa tgggaatctc attcccaccc acacgcagcc     300
cagctacagg ttcaaggcca acaacaatga cagcggggag tacacgtgcc agactggcca     360
gaccagcctc agcgaccctg tgcatctgac tgtgctttct gagtggctgg tgctccagac     420
ccctcacctg gagttccagg agggagaaac catcgtgctg aggtgccaca gctggaagga     480
caagcctctg gtcaaggtca cattcttcca gaatggaaaa tccaagaaat tttcccgttc     540
ggatcccaac ttctccatcc acaagcaaa ccacagtcac agtggtgatt accactgcac     600
aggaaacata ggctacacgc tgttctcatc aagcctgtg accatcactg tccaagctcc     660
cagctcttca cccatggagg agcgcaaatg ttgtgtcgag tgcccaccgt gcccagcacc     720
acctgtggca ggaccgtcag tcttccttt cccccaaaa cccaaggaca ccctcatgat     780
ctcccggacc cctgaggtca cgtgcgtggt ggtggacgtg agccacgaag accccgaggt     840
ccagttcaac tggtacgtgg acggcatgga ggtgcataat gccaagacaa agccacggga     900
ggagcagttc aacagcacgt tccgtgtggt cagcgtcctc accgtcgtgc accaggactg     960
gctgaacggc aaggagtaca gtgcaaggt ctccaacaaa ggcctcccag cccccatcga    1020
gaaaaccatc tccaaaacca agggcagcc ccgagaacca caggtgtaca ccctgccccc    1080
atcccgggag gagatgacca gaaccaggt cagcctgacc tgcctggtca aaggcttcta    1140
ccccagcgac atcgccgtgg agtgggagag caatgggcag ccggagaaca actacaagac    1200
cacacctccc atgctggact ccgacggctc cttcttcctc tacagcaagc tcaccgtgga    1260
caagagcagg tggcagcagg gaacgtcctt ctcatgctct gtgatgcatg aggctctgca    1320
caaccactac acacagaaga gcctctccct gtctccgggt aaatgagtgc ggccgcgaat    1380
tc                                                                  1382

<210> SEQ ID NO 6
<211> LENGTH: 1418
<212> TYPE: DNA
<213> ORGANISM: Homo sapiens
<220> FEATURE:
<223> OTHER INFORMATION: sFcRIIIA insert

<400> SEQUENCE: 6
atgggatgga gctgtatcat cctcttcttg gtagcaacag ctacaggtaa ggggctcaca      60
```

```
gtagcaggct tgaggtctgg acatatatat gggtgacaat gacatccact ttgcctttct      120
ctccacaggt gtccactcca tgcggactga agatctcccc aaggctgtgg tgttcctgga      180
gcctcaatgg tacagggtgc tcgagaagga cagtgtgact ctgaagtgcc agggagccta      240
ctcccctgag gacaattcca cacagtggtt tcacaatgag agcctcatct caagccaggc      300
ctcgagctac ttcattgacg ctgccacagt cgacgacagt ggagagtaca ggtgccagac      360
aaacctctcc accctcagtg acccggtgca gctagaagtc catatcggct ggctgttgct      420
ccaggcccct cggtgggtgt tcaaggagga agaccctatt cacctgaggt gtcacagctg      480
gaagaacact gctctgcata aggtcacata tttacagaat ggcaaaggca ggaagtattt      540
tcatcataat tctgacttct acattccaaa agccacactc aaagacagcg gctcctactt      600 ctgcagggg cttgttggga gtaaaaatgt gtcttcagag actgtgaaca tcaccatcac      660
tcaaggtttg gcagtgtcaa ccatctcatc attctttcca cctgggtacc aagtcgagcg      720
caaatgttgt gtcgagtgcc caccgtgccc agcaccacct gtggcaggac cgtcagtctt      780
cctcttcccc ccaaaaccca aggacaccct catgatctcc cggacccctg aggtcacgtg      840
cgtggtggtg gacgtgagcc acgaagaccc cgaggtccag ttcaactggt acgtggacgg      900
catggaggtg cataatgcca agacaaagcc acgggaggag cagttcaaca gcacgttccg      960
tgtggtcagc gtcctcaccg tcgtgcacca ggactggctg aacggcaagg agtacaagtg     1020
caaggtctcc aacaaaggcc tcccagcccc catcgagaaa accatctcca aaaccaaagg     1080
gcagccccga gaaccacagg tgtacaccct gcccccatcc cggaggagaga tgaccaagaa     1140 ccaggtcagc ctgacctgcc tggtcaaagg cttctacccc agcgacatcg ccgtggagtg     1200
ggagagcaat gggcagccgg agaacaacta caagaccaca cctcccatgc tggactccga     1260
cggctccttc ttcctctaca gcaagctcac cgtggacaag agcaggtggc agcaggggaa     1320
cgtcttctca tgctccgtga tgcatgaggc tctgcacaac cactacacac agaagagcct     1380
ctccctgtct ccgggtaaat gagtgcggcc gcgaattc                              1418
```

<210> SEQ ID NO 7  
<211> LENGTH: 1391  
<212> TYPE: DNA  
<213> ORGANISM: Homo sapiens  
<220> FEATURE:  
<223> OTHER INFORMATION: sFcRIIA-131H

<400> SEQUENCE: 7

```
gctagccacc atgggaatcc tgtcattctt acctgtcctt gccactgaga gtgactgggc       60
tgactgcaag tcccccagc cttggggtca tatgcttctg tggacagctg tgctattcct      120
ggctcctgtt gctgggacac ctgcagctcc cccaaaggct gtgctgaaac ttgagccccc      180
gtggatcaac gtgctccagg aggactctgt gactctgaca tgccagggggg ctcgcagccc      240 tgagagcgac tccattcagt ggttccacaa tgggaatctc attcccaccc acacgcagcc      300
cagctacagg ttcaaggcca acaacaatga cagcggggag tacacgtgcc agactggcca      360
gaccagcctc agcgaccctg tgcatctgac tgtgctttcc gaatggctgg tgctccagac      420
ccctcacctg gagttccagg agggagaaac catcatgctg aggtgccaca gctggaagga      480
caagcctctg gtcaaggtca cattcttcca gaatggaaaa tcccagaaat tctcccattt      540
ggatcccacc ttctccatcc acaaagcaaa ccacagtcac agtggtgatt accactgcac      600
aggaaacata ggctacacag cgtgttctca tcaagcctgt gaccatcactg tccaagtgcc      660
```

| | |
|---|---|
| cagcatgggc agctcttcac ccatggagga gcgcaaatgt tgtgtcgagt gcccaccgtg | 720 |
| cccagcacca cctgtggcag gaccgtcagt cttcctcttc cccccaaaac ccaaggacac | 780 |
| cctcatgatc tcccggaccc ctgaggtcac gtgcgtggtg gtggacgtga gccacgaaga | 840 |
| ccccgaggtc cagttcaact ggtacgtgga cggcatggag gtgcataatg ccaagacaaa | 900 |
| gccacgggag gagcagttca acagcacgtt ccgtgtggtc agcgtcctca ccgtcgtgca | 960 |
| ccaggactgg ctgaacggca aggagtacaa gtgcaaggtc tccaacaaag gcctcccagc | 1020 |
| ccccatcgag aaaaccatct ccaaaaccaa agggcagccc cgagaaccac aggtgtacac | 1080 |
| cctgccccca tcccgggagg agatgaccaa gaaccaggtc agcctgacct gcctggtcaa | 1140 |
| aggcttctac cccagcgaca tcgccgtgga gtgggagagc aatgggcagc cggagaacaa | 1200 |
| ctacaagacc acacctccca tgctggactc cgacggctcc ttcttcctct acagcaagct | 1260 |
| caccgtggac aagagcaggt ggcagcaggg gaacgtcttc tcatgctctg tgatgcatga | 1320 |
| ggctctgcac aaccactaca cacagaagag cctctccctg tctccgggta aatgagtgcg | 1380 |
| gccgcgaatt c | 1391 |

<210> SEQ ID NO 8
<211> LENGTH: 1391
<212> TYPE: DNA
<213> ORGANISM: Homo sapiens
<220> FEATURE:
<223> OTHER INFORMATION: sFcRIIA-131R

<400> SEQUENCE: 8

| | |
|---|---|
| gctagccacc atgggaatcc tgtcattctt acctgtcctt gccactgaga gtgactgggc | 60 |
| tgactgcaag tcccccagc cttggggtca tatgcttctg tggacagctg tgctattcct | 120 |
| ggctcctgtt gctgggacac ctgcagctcc cccaaaggct gtgctgaaac ttgagccccc | 180 |
| gtggatcaac gtgctccagg aggactctgt gactctgaca tgccagggg ctcgcagccc | 240 |
| tgagagcgac tccattcagt ggttccacaa tgggaatctc attcccaccc acacgcagcc | 300 |
| cagctacagg ttcaaggcca caacaatga cagcggggag tacacgtgcc agactggcca | 360 |
| gaccagcctc agcgaccctg tgcatctgac tgtgctttcc gaatggctgg tgctccagac | 420 |
| ccctcacctg gagttccagg agggagaaac catcatgctg aggtgccaca gctggaagga | 480 |
| caagcctctg gtcaaggtca cattcttcca gaatggaaaa tcccagaaat tctcccgttt | 540 |
| ggatcccacc ttctccatcc acaaagcaaa ccacagtcac agtggtgatt accactgcac | 600 |
| aggaaacata ggctacacgc tgttctcatc caagcctgtg accatcactg tccaagtgcc | 660 |
| cagcatgggc agctcttcac ccatggagga gcgcaaatgt tgtgtcgagt gcccaccgtg | 720 |
| cccagcacca cctgtggcag gaccgtcagt cttcctcttc cccccaaaac ccaaggacac | 780 |
| cctcatgatc tcccggaccc ctgaggtcac gtgcgtggtg gtggacgtga gccacgaaga | 840 |
| ccccgaggtc cagttcaact ggtacgtgga cggcatggag gtgcataatg ccaagacaaa | 900 |
| gccacgggag gagcagttca acagcacgtt ccgtgtggtc agcgtcctca ccgtcgtgca | 960 |
| ccaggactgg ctgaacggca aggagtacaa gtgcaaggtc tccaacaaag gcctcccagc | 1020 |
| ccccatcgag aaaaccatct ccaaaaccaa agggcagccc cgagaaccac aggtgtacac | 1080 |
| cctgccccca tcccgggagg agatgaccaa gaaccaggtc agcctgacct gcctggtcaa | 1140 |
| aggcttctac cccagcgaca tcgccgtgga gtgggagagc aatgggcagc cggagaacaa | 1200 |
| ctacaagacc acacctccca tgctggactc cgacggctcc ttcttcctct acagcaagct | 1260 |
| caccgtggac aagagcaggt ggcagcaggg gaacgtcttc tcatgctctg tgatgcatga | 1320 |

-continued

```
ggctctgcac aaccactaca cacagaagag cctctccctg tctccgggta aatgagtgcg    1380
gccgcgaatt c                                                         1391
```

<210> SEQ ID NO 9
<211> LENGTH: 317
<212> TYPE: PRT
<213> ORGANISM: Homo sapiens
<220> FEATURE:
<223> OTHER INFORMATION: human FcRIIa

<400> SEQUENCE: 9

```
Met Ala Met Glu Thr Gln Met Ser Gln Asn Val Cys Pro Arg Asn Leu
1               5                   10                  15

Trp Leu Leu Gln Pro Leu Thr Val Leu Leu Leu Leu Ala Ser Ala Asp
            20                  25                  30

Ser Gln Ala Ala Ala Pro Pro Lys Ala Val Leu Lys Leu Glu Pro Pro
        35                  40                  45

Trp Ile Asn Val Leu Gln Glu Asp Ser Val Thr Leu Thr Cys Gln Gly
    50                  55                  60

Ala Arg Ser Pro Glu Ser Asp Ser Ile Gln Trp Phe His Asn Gly Asn
65                  70                  75                  80

Leu Ile Pro Thr His Thr Gln Pro Ser Tyr Arg Phe Lys Ala Asn Asn
                85                  90                  95

Asn Asp Ser Gly Glu Tyr Thr Cys Gln Thr Gly Gln Thr Ser Leu Ser
            100                 105                 110

Asp Pro Val His Leu Thr Val Leu Ser Glu Trp Leu Val Leu Gln Thr
        115                 120                 125

Pro His Leu Glu Phe Gln Glu Gly Glu Thr Ile Met Leu Arg Cys His
    130                 135                 140

Ser Trp Lys Asp Lys Pro Leu Val Lys Val Thr Phe Phe Gln Asn Gly
145                 150                 155                 160

Lys Ser Gln Lys Phe Ser Arg Leu Asp Pro Thr Phe Ser Ile Pro Gln
                165                 170                 175

Ala Asn His Ser His Ser Gly Asp Tyr His Cys Thr Gly Asn Ile Gly
            180                 185                 190

Tyr Thr Leu Phe Ser Ser Lys Pro Val Thr Ile Thr Val Gln Val Pro
        195                 200                 205

Ser Met Gly Ser Ser Ser Pro Met Gly Ile Ile Val Ala Val Val Ile
    210                 215                 220

Ala Thr Ala Val Ala Ala Ile Val Ala Ala Val Val Ala Leu Ile Tyr
225                 230                 235                 240

Cys Arg Lys Lys Arg Ile Ser Ala Asn Ser Thr Asp Pro Val Lys Ala
                245                 250                 255

Ala Gln Phe Glu Pro Pro Gly Arg Gln Met Ile Ala Ile Arg Lys Arg
            260                 265                 270

Gln Leu Glu Glu Thr Asn Asn Asp Tyr Glu Thr Ala Asp Gly Gly Tyr
        275                 280                 285

Met Thr Leu Asn Pro Arg Ala Pro Thr Asp Asp Lys Asn Ile Tyr
    290                 295                 300

Leu Thr Leu Pro Pro Asn Asp His Val Asn Ser Asn Asn
305                 310                 315
```

<210> SEQ ID NO 10
<211> LENGTH: 42
<212> TYPE: DNA

<213> ORGANISM: Artificial Sequence
<220> FEATURE:
<223> OTHER INFORMATION: Primer: SJ45f

<400> SEQUENCE: 10
ctctccacag gtgtccactc catgcggact gaagatctcc cc          42

<210> SEQ ID NO 11
<211> LENGTH: 24
<212> TYPE: DNA
<213> ORGANISM: Artificial Sequence
<220> FEATURE:
<223> OTHER INFORMATION: primer: SJ48r

<400> SEQUENCE: 11
gcgctcgact tggtacccag gtgg                              24

<210> SEQ ID NO 12
<211> LENGTH: 30
<212> TYPE: DNA
<213> ORGANISM: Artificial Sequence
<220> FEATURE:
<223> OTHER INFORMATION: primer: H009

<400> SEQUENCE: 12
cgagctagct gagatcacag ttctctctac                        30

<210> SEQ ID NO 13
<211> LENGTH: 21
<212> TYPE: DNA
<213> ORGANISM: Artificial Sequence
<220> FEATURE:
<223> OTHER INFORMATION: primer: SJ27r

<400> SEQUENCE: 13
ggagtggaca cctgtggaga g                                 21

<210> SEQ ID NO 14
<211> LENGTH: 41
<212> TYPE: DNA
<213> ORGANISM: Artificial Sequence
<220> FEATURE:
<223> OTHER INFORMATION: primer: SJ47f

<400> SEQUENCE: 14
cctgggtacc aagtcgagcg caaatgttgt gtcgagtgcc c           41

<210> SEQ ID NO 15
<211> LENGTH: 38
<212> TYPE: DNA
<213> ORGANISM: Artificial Sequence
<220> FEATURE:
<223> OTHER INFORMATION: primer: SJ20r

<400> SEQUENCE: 15
ggcgaattcg cggccgcact catttacccg gagacagg                38

<210> SEQ ID NO 16
<211> LENGTH: 37
<212> TYPE: DNA
<213> ORGANISM: Artificial Sequence
<220> FEATURE:
<223> OTHER INFORMATION: primer: SJ84f

<400> SEQUENCE: 16
ggcggctagc caccatggga atcctgtcat tcttacc                 37

```
<210> SEQ ID NO 17
<211> LENGTH: 35
<212> TYPE: DNA
<213> ORGANISM: Artificial Sequence
<220> FEATURE:
<223> OTHER INFORMATION: primer: SJ82r

<400> SEQUENCE: 17
catttgcgct cccccatggg tgaagagctg ggagc                                35

<210> SEQ ID NO 18
<211> LENGTH: 34
<212> TYPE: DNA
<213> ORGANISM: Artificial Sequence
<220> FEATURE:
<223> OTHER INFORMATION: primer: SJ83f

<400> SEQUENCE: 18
ccatggggga gcgcaaatgt tgtgtcgagt gccc                                 34

<210> SEQ ID NO 19
<211> LENGTH: 38
<212> TYPE: DNA
<213> ORGANISM: Artificial Sequence
<220> FEATURE:
<223> OTHER INFORMATION: primer: SJ20r

<400> SEQUENCE: 19
ggcgaattcg cggccgcact catttacccg gagacagg                             38

<210> SEQ ID NO 20
<211> LENGTH: 83
<212> TYPE: PRT
<213> ORGANISM: Homo sapiens
<220> FEATURE:
<223> OTHER INFORMATION: Membrane proximal domain of RIIIa

<400> SEQUENCE: 20

Val His Ile Gly Trp Leu Leu Leu Gln Ala Pro Arg Trp Val Phe Lys
1               5                   10                  15

Glu Glu Asp Pro Ile His Leu Arg Cys His Ser Trp Lys Asn Thr Ala
            20                  25                  30

Leu His Lys Val Thr Tyr Leu Gln Asn Gly Lys Gly Arg Lys Tyr Phe
        35                  40                  45

His His Asn Ser Asp Phe Tyr Ile Pro Lys Ala Thr Leu Lys Asp Ser
    50                  55                  60

Gly Ser Tyr Phe Cys Arg Gly Leu Val Gly Ser Lys Asn Val Ser Ser
65                  70                  75                  80

Glu Thr Val

<210> SEQ ID NO 21
<211> LENGTH: 78
<212> TYPE: PRT
<213> ORGANISM: Homo sapiens
<220> FEATURE:
<223> OTHER INFORMATION: Membrane proximal domain of RIIb

<400> SEQUENCE: 21

Val Leu Ser Glu Trp Leu Val Leu Gln Thr Pro His Leu Glu Phe Gln
1               5                   10                  15

Glu Gly Glu Thr Ile Val Leu Arg Cys His Ser Trp Lys Asp Lys Pro
            20                  25                  30
```

-continued

```
Leu Val Lys Val Thr Phe Phe Gln Asn Gly Lys Ser Lys Lys Phe Ser
        35                  40                  45

Arg Ser Asp Pro Asn Phe Ser Ile Pro Gln Ala Asn His Ser His Ser
    50                  55                  60

Gly Asp Tyr His Cys Thr Gly Asn Ile Gly Tyr Thr Leu Phe
65                  70                  75

<210> SEQ ID NO 22
<211> LENGTH: 78
<212> TYPE: PRT
<213> ORGANISM: Homo sapiens
<220> FEATURE:
<223> OTHER INFORMATION: Membrane proximal domain of RIIa(131R)

<400> SEQUENCE: 22

Val Leu Ser Glu Trp Leu Val Leu Gln Thr Pro His Leu Glu Phe Gln
1               5                   10                  15

Glu Gly Glu Thr Ile Met Leu Arg Cys His Ser Trp Lys Asp Lys Pro
            20                  25                  30

Leu Val Lys Val Thr Phe Phe Gln Asn Gly Lys Ser Gln Lys Phe Ser
        35                  40                  45

Arg Leu Asp Pro Thr Phe Ser Ile Pro Gln Ala Asn His Ser His Ser
    50                  55                  60

Gly Asp Tyr His Cys Thr Gly Asn Ile Gly Tyr Thr Leu Phe
65                  70                  75

<210> SEQ ID NO 23
<211> LENGTH: 78
<212> TYPE: PRT
<213> ORGANISM: Homo sapiens
<220> FEATURE:
<223> OTHER INFORMATION: Membrane proximal domain of RIIa(131H)

<400> SEQUENCE: 23

Val Leu Ser Glu Trp Leu Val Leu Gln Thr Pro His Leu Glu Phe Gln
1               5                   10                  15

Glu Gly Glu Thr Ile Met Leu Arg Cys His Ser Trp Lys Asp Lys Pro
            20                  25                  30

Leu Val Lys Val Thr Phe Phe Gln Asn Gly Lys Ser Gln Lys Phe Ser
        35                  40                  45

His Leu Asp Pro Thr Phe Ser Ile Pro Gln Ala Asn His Ser His Ser
    50                  55                  60

Gly Asp Tyr His Cys Thr Gly Asn Ile Gly Tyr Thr Leu Phe
65                  70                  75

<210> SEQ ID NO 24
<211> LENGTH: 887
<212> TYPE: DNA
<213> ORGANISM: Homo sapiens
<220> FEATURE:
<223> OTHER INFORMATION: human FcRIIIa

<400> SEQUENCE: 24
tctttggtga cttgtccact ccagtgtggc atcatgtggc agctgctcct cccaactgct     60
ctgctacttc tagtttcagc tggcatgcgg actgaagatc tcccaaaggc tgtggtgttc    120
ctggagcctc aatggtacag ggtgctcgag aaggacagtg tgactctgaa gtgccaggga    180
gcctactccc ctgaggacaa ttccacacag tggtttcaca tgagagcct catctcaagc    240 caggcctcga gctacttcat tgacgctgcc acagtcgacg acagtggaga gtacaggtgc    300
```

```
cagacaaacc tctccaccct cagtgacccg gtgcagctag aagtccatat cggctggctg    360
ttgctccagg cccctcggtg ggtgttcaag gaggaagacc ctattcacct gaggtgtcac    420
agctggaaga acactgctct gcataaggtc acatatttac agaatggcaa aggcaggaag    480
tattttcatc ataattctga cttctacatt ccaaaagcca cactcaaaga cagcggctcc    540
tacttctgca gggggctttt tgggagtaaa aatgtgtctt cagagactgt gaacatcacc    600
atcactcaag gtttggcagt gtcaaccatc tcatcattct ttccacctgg gtaccaagtc    660
tctttctgct tggtgatggt actcctttt gcagtggaca caggactata tttctctgtg    720
aagacaaaca ttcgaagctc aacaagagac tggaaggacc ataaatttaa atggagaaag    780
gaccctcaag acaaatgacc cccatcccat gggggtaata agagcagtag cagcagcatc    840
tctgaacatt tctctggatt tgcaaccca tcatcctcag gcctctc                    887
```

<210> SEQ ID NO 25
<211> LENGTH: 254
<212> TYPE: PRT
<213> ORGANISM: Homo sapiens
<220> FEATURE:
<223> OTHER INFORMATION: human FcRIIIa

<400> SEQUENCE: 25

```
Met Trp Gln Leu Leu Pro Thr Ala Leu Leu Leu Leu Val Ser Ala
 1               5                  10                  15

Gly Met Arg Thr Glu Asp Leu Pro Lys Ala Val Val Phe Leu Glu Pro
                20                  25                  30

Gln Trp Tyr Arg Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
        50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250
```

<210> SEQ ID NO 26
<211> LENGTH: 1393
<212> TYPE: DNA
<213> ORGANISM: Homo sapiens
<220> FEATURE:
<223> OTHER INFORMATION: human FcRIIB2

<400> SEQUENCE: 26

```
gactgctgtg ctctgggcgc cagctcgctc cagggagtga tgggaatcct gtcattctta      60
cctgtccttg ccactgagag tgactgggct gactgcaagt cccccagcc ttggggtcat     120
atgcttctgt ggacagctgt gctattcctg gctcctgttg ctgggacacc tgcagctccc     180
ccaaaggctg tgctgaaact cgagcccag tggatcaacg tgctccagga ggactctgtg     240
actctgacat gccggggac tcacagccct gagagcgact ccattcagtg gttccacaat     300
gggaatctca ttcccaccca cacgcagccc agctacaggt tcaaggccaa caacaatgac     360
agcggggagt cacgtgcca gactggccag accagcctca cgaccctgt gcatctgact     420
gtgctttctg agtggctggt gctccagacc cctcacctgg agttccagga gggagaaacc     480
atcgtgctga ggtgccacag ctggaaggac aagcctctgg tcaaggtcac attcttccag     540
aatggaaaat ccaagaaatt ttcccgttcg atcccaact tctccatccc acaagcaaac     600
cacagtcaca gtggtgatta ccactgcaca ggaaacatag ctacacgct gttctcatcc     660
aagcctgtga ccatcactgt ccaagctccc agctcttcac cgatggggat cattgtggct     720
gtggtcactg ggattgctgt agcggccatt gttgctgctg tagtggcctt gatctactgc     780
aggaaaaagc ggatttcagc caatcccact aatcctgatg aggctgacaa agttggggct     840
gagaacacaa tcacctattc acttctcatg caccgggatg ctctggaaga gcctgatgac     900
cagaaccgta tttagtctcc attgtcttgc attgggattt gagaagaaaa tcagagaggg     960
aagatctggt atttcctggc ctaaattccc cttggaggac aggagatgc tcgagttcca    1020
aaagagaagg tttcttccag agtcatctac ctgagtcctg aagctccctg tcctgaaagc    1080
cacagacaat atggtcccaa ataccgact gcacctgctg tcttcagctc ttcttgacat    1140
caaggctctt ccgttccaca tccacacagc caatccaatt aatcaaacca ctgttattaa    1200
cagataatag caacttggga aatgcttatg ttacaggtta ccgttgagaa caatcatcta    1260
aatctatatg atttcagaaa tgttaaaata gactaacctc taccagcaca ttaaaagtga    1320
ttgtttctgg gtgatttatt gatgattttt attttcttta tttttctata aagatcatat    1380
attactttta ata                                                       1393
```

<210> SEQ ID NO 27
<211> LENGTH: 291
<212> TYPE: PRT
<213> ORGANISM: Homo sapiens
<220> FEATURE:
<223> OTHER INFORMATION: human FcRIIB

<400> SEQUENCE: 27

Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro
        35                  40                  45

Lys Ala Val Leu Lys Leu Glu Pro Gln Trp Ile Asn Val Leu Gln Glu
    50                  55                  60

```
Asp Ser Val Thr Leu Thr Cys Arg Gly Thr His Ser Pro Glu Ser Asp
 65                  70                  75                  80

Ser Ile Gln Trp Phe His Asn Gly Asn Leu Ile Pro Thr His Thr Gln
                 85                  90                  95

Pro Ser Tyr Arg Phe Lys Ala Asn Asn Asn Asp Ser Gly Glu Tyr Thr
            100                 105                 110

Cys Gln Thr Gly Gln Thr Ser Leu Ser Asp Pro Val His Leu Thr Val
        115                 120                 125

Leu Ser Glu Trp Leu Val Leu Gln Thr Pro His Leu Glu Phe Gln Glu
    130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Lys Phe Ser Arg
                165                 170                 175

Ser Asp Pro Asn Phe Ser Ile Pro Gln Ala Asn His Ser His Ser Gly
            180                 185                 190

Asp Tyr His Cys Thr Gly Asn Ile Gly Tyr Thr Leu Phe Ser Ser Lys
        195                 200                 205

Pro Val Thr Ile Thr Val Gln Ala Pro Ser Ser Ser Pro Met Gly Ile
    210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Asn Pro
                245                 250                 255

Thr Asn Pro Asp Glu Ala Asp Lys Val Gly Ala Glu Asn Thr Ile Thr
            260                 265                 270

Tyr Ser Leu Leu Met His Pro Asp Ala Leu Glu Glu Pro Asp Asp Gln
        275                 280                 285

Asn Arg Ile
    290

<210> SEQ ID NO 28
<211> LENGTH: 1303
<212> TYPE: DNA
<213> ORGANISM: Homo sapiens
<220> FEATURE:
<223> OTHER INFORMATION: human FcRIIB1

<400> SEQUENCE: 28
tgactgcaag tcccccagc cttggggtca tatgcttctg tggacagctg tgctattcct      60
ggctcctgtt gctgggacac ctgcagctcc cccaaaggct gtgctgaaac tcgagcccca   120
gtggatcaac gtgctccagg aggactctgt gactctgaca tgccggggga ctcacagccc   180
tgagagcgac tccattcagt ggttccacaa tgggaatctc attcccaccc acacgcagcc   240
cagctacagg ttcaaggcca acaacaatga cagcggggag tacacgtgcc agactggcca   300
gaccagcctc agcgaccctg tgcatctgac tgtgctttct gagtggctgg tgctccagac   360
ccctcacctg gagttccagg agggagaaac catcgtgctg aggtgccaca gctggaagga   420
caagcctctg gtcaaggtca cattcttcca gaatggaaaa tccaagaaat tttcccgttc   480
ggatcccaac ttctccatcc cacaagcaaa ccacagtcac agtggtgatt accactgcac   540
aggaaacata ggctacacgc tgttctcatc aagcctgtg accatcactg tccaagctcc   600
cagctcttca ccgatgggga tcattgtggc tgtggtcact gggattgctg tagcggccat   660
tgttgctgct gtagtggcct tgatctactg caggaaaaag cggatttcag ctctcccagg   720
```

```
ataccctgag tgcagggaaa tgggagagac cctccctgag aaaccagcca atcccactaa      780
tcctgatgag gctgacaaag ttggggctga gaacacaatc acctattcac ttctcatgca      840
cccggatgct ctggaagagc ctgatgacca gaaccgtatt tagtctccat tgtcttgcat      900
tgggatttga agaaaatc agagagggaa gatctggtat ttcctggcct aaattcccct       960
tggaggacag ggagatgctc gagttccaaa agagaaggtt tcttccagag tcatctacct     1020
gagtcctgaa gctccctgtc ctgaaagcca cagacaatat ggtcccaaat aaccgactgc     1080
acctgctgtc ttcagctctt cttgacatca aggctcttcc gttccacatc cacacagcca     1140
atccaattaa tcaaaccact gttattaaca gataatagca acttgggaaa tgcttatgtt     1200
acaggttacc gttgagaaca atcatctaaa tctatatgat ttcagaaatg ttaaaataga     1260
ctaacctcta ccagcacatt aaaagtgatt gtttctgggt gat                       1303
```

<210> SEQ ID NO 29
<211> LENGTH: 1466
<212> TYPE: DNA
<213> ORGANISM: Homo sapiens
<220> FEATURE:
<223> OTHER INFORMATION: human FcRIIB

<400> SEQUENCE: 29

```
gccctctagg gtagaatcgc caagctttga gagaaggctg tgactgctgt gctctgggcg       60
ccagctcgct ccagggagtg atgggaatcc tgtcattctt acctgtcctt gccactgaga      120
gtgactgggc tgactgcaag tcccccagc cttggggtca tatgcttctg tggacagctg      180
tgctattcct ggcagctccc ccaaaggctg tgctgaaact cgagcccag tggatcaacg       240 tgctccagga ggactctgtg actctgacat gccgggggac tcacagccct gagagcgact      300
ccattcagtg gttccacaat gggaatctca ttcccaccca cacgcagccc agctacaggt      360
tcaaggccaa caacaatgac agcggggagt acacgtgcca gactggccag accagcctca      420
gcgaccctgt gcatctgact gtgctttctg agtggctggt gctccagacc cctcacctgg      480
agttccagga gggagaaacc atcgtgctga ggtgccacag ctggaaggac aagcctctgg      540
tcaaggtcac attcttccag aatggaaaat ccaagaaatt tcccgttcg atcccaact       600 tctccatccc acaagcaaac cacagtcaca gtggtgatta ccactgcaca ggaaacatag      660
gctacacgct gttctcatcc aagcctgtga ccatcactgt ccaagctccc agctcttcac      720
cgatggggat cattgtggct gtggtcactg ggattgctgt agcggccatt gttgctgctg      780
tagtggcctt gatctactgc aggaaaaagc ggatttcagc tctcccagga taccctgagt      840
gcagggaaat gggagagacc ctccctgaga aaccagccaa tccccactaat cctgatgagg      900 ctgacaaagt tggggctgag aacacaatca cctattcact tctcatgcac ccggatgctc      960
tggaagagcc tgatgaccag aaccgtattt agtctccatt gtcttgcatt gggatttgag     1020
aagaaaatca gagagggaag atctggtatt tcctggccta aattcccctt ggaggacagg     1080
gagatgctcg agttccaaaa gagaaggttt cttccagagt catctacctg agtcctgaag     1140
ctccctgtcc tgaaagccac agacaatatg gtcccaaata accgactgca cctgctgtct     1200
tcagctcttc ttgacatcaa ggctcttccg ttccacatcc acacagccaa tccaattaat     1260
caaaccactg ttattaacag ataatagcaa cttgggaaat gcttatgtta caggttaccg     1320
ttgagaacaa tcatctaaat ctatatgatt tcagaaatgt taaaatagac taacctctac     1380
cagcacatta aaagtgattg tttctgggtg atttattgat gattttatt ttctttattt     1440
```

```
ttctataaag atcatatatt actttt                                          1466
```

<210> SEQ ID NO 30
<211> LENGTH: 2372
<212> TYPE: DNA
<213> ORGANISM: Homo sapiens
<220> FEATURE:
<223> OTHER INFORMATION: Human FcRIIa

<400> SEQUENCE: 30

```
ttctgggatg gctatggaga cccaaatgtc tcagaatgta tgtcccagaa acctgtggct        60
gcttcaacca ttgacagttt tgctgctgct ggcttctgca gacagtcaag ctgcagctcc       120
cccaaaggct gtgctgaaac ttgagccccc gtggatcaac gtgctccagg aggactctgt       180
gactctgaca tgccagggggg ctcgcagccc tgagagcgac tccattcagt ggttccacaa      240
tgggaatctc attcccaccc acacgcagcc cagctacagg ttcaaggcca caacaatga       300
cagcggggag tacacgtgcc agactggcca gaccagcctc agcgaccctg tgcatctgac      360
tgtgctttcc gaatggctgg tgctccagac ccctcacctg gagttccagg agggagaaac      420
catcatgctg aggtgccaca gctggaagga caagcctctg tcaaggtca cattcttcca       480
gaatggaaaa tcccagaaat ctcccgtttt ggatcccacc ttctccatcc acaagcaaa       540
ccacagtcac agtggtgatt accactgcac aggaaacata ggctacacgc tgttctcatc      600
caagcctgtg accatcactg tccaagtgcc agcatgggc agctcttcac caatggggat      660
cattgtggct gtggtcattg cgactgctgt agcagccatt gttgctgctg tagtggcctt      720
gatctactgc aggaaaaagc ggatttcagc caattccact gatcctgtga aggctgccca      780
atttgagcca cctggacgtc aaatgattgc catcagaaag agacaacttg aagaaaccaa      840
caatgactat gaaacagctg acggcggcta catgactctg aaccccaggg cacctactga     900
cgatgataaa aacatctacc tgactcttcc tcccaacgac catgtcaaca gtaataacta     960
aagagtaacg ttatgccatg tggtcatact ctcagcttgc tagtggatga caaaaagagg     1020
ggaattgtta aaggaaaatt taaatggaga ctggaaaaat cctgagcaaa caaaaccacc     1080
tggcccttag aaatagcttt aactttgctt aaactacaaa cacaagcaaa acttcacggg     1140
gtcatactac atacaagcat aagcaaaact taacttggat catttctggt aaatgcttat     1200
gttagaaata agacaacccc agccaatcac aagcagccta ctaacatata attaggtgac     1260
tagggacttt ctaagaagat acctaccccc aaaaaacaat tatgtaattg aaaaccaacc     1320
gattgccttt attttgcttc cacatttttcc caataaatac ttgcctgtga cattttgcca     1380
ctggaacact aaacttcatg aattgcgcct cagattttg ctttaacatc tttttttttt      1440
tttgacagag tctcaatctg ttacccaggc tggagtgcag tggtgctatc ttggctcact     1500
gcaaacccgc ctcccaggtt aagcgattc tcatgcctca gcctcccagt agctgggatt     1560
agaggcatgt gcatcatacc cagctaattt ttgtatttt tatttttat ttttagtaga      1620
gacagggttt cgcaatgttg gccaggcgat ctcgaacttc tggcctctag cgatctgccg     1680
cctcggcctc ccaaagtgct gggatgacca gcatcagccc caatgtccag cctctttaac     1740
atcttctttc ctatgccctc tctgtggatc cctactgctg gtttctgcct tctccatgct     1800
gagaacaaaa tcacctattc actgcttatg cagtcggaag ctccagaaga caaagagcc     1860
caattaccag aaccacatta agtctccatt gttttgcctt gggatttgag aagagaatta     1920
gagaggtgag gatctggtat ttcctggact aaattcccct tggaagacga agggatgctg     1980
cagttccaaa agagaaggac tcttccagag tcatctacct gagtcccaaa gctccctgtc     2040
```

| | | | |
|---|---|---|---|
| ctgaaagcca | cagacaatat | ggtcccaaat | gactgactgc | accttctgtg | cctcagccgt | 2100 |
| tcttgacatc | aagaatcttc | tgttccacat | ccacacagcc | aatacaatta | gtcaaaccac | 2160 |
| tgttattaac | agatgtagca | acatgagaaa | cgcttatgtt | acaggttaca | tgagagcaat | 2220 |
| catgtaagtc | tatatgactt | cagaaatgtt | aaaatagact | aacctctaac | aacaaattaa | 2280 |
| aagtgattgt | ttcaaggtga | tgcaattatt | gatgacctat | tctatttgtc | tataatgatc | 2340 |
| atatattacc | tttgtaataa | aacattataa | tc | | | 2372 |

<210> SEQ ID NO 31
<211> LENGTH: 2009
<212> TYPE: DNA
<213> ORGANISM: Homo sapiens
<220> FEATURE:
<223> OTHER INFORMATION: Human IgG2

<400> SEQUENCE: 31

| | | | | | | |
|---|---|---|---|---|---|---|
| agctttctgg | ggcgagccgg | gcctgacttt | ggctttgggg | cagggagtgg | gctaaggtga | 60 |
| ggcaggtggc | gccagccagg | tgcacaccca | atgcccgtga | gcccagacac | tggaccctgc | 120 |
| ctggaccctc | gtggatagac | aagaaccgag | gggcctctgc | gcctgggccc | agctctgtcc | 180 |
| cacaccgcgg | tcacatggca | ccacctctct | tgcagcctcc | accaagggcc | catcggtctt | 240 |
| cccccctggcg | ccctgctcca | ggagcacctc | cgagagcaca | gccgccctgg | gctgcctggt | 300 |
| caaggactac | ttccccgaac | cggtgacggt | gtcgtggaac | tcaggcgctc | tgaccagcgg | 360 |
| cgtgcacacc | ttcccagctg | tcctacagtc | ctcaggactc | tactccctca | gcagcgtggt | 420 |
| gaccgtgccc | tccagcaact | tcggcaccca | gacctacacc | tgcaacgtag | atcacaagcc | 480 |
| cagcaacacc | aaggtggaca | agacagttgg | tgagaggcca | gctcagggag | ggagggtgtc | 540 |
| tgctggaagc | caggctcagc | cctcctgcct | ggacgcaccc | cggctgtgca | gccccagccc | 600 |
| agggcagcaa | ggcaggcccc | atctgtctcc | tcacccggag | gcctctgccc | gccccactca | 660 |
| tgctcaggga | gagggtcttc | tggctttttc | caccaggctc | caggcaggca | caggctgggt | 720 |
| gcccctaccc | caggccctc | acacacaggg | gcaggtgctt | ggctcagacc | tgccaaaagc | 780 |
| catatccggg | aggaccctgc | ccctgaccta | agccgacccc | aaaggccaaa | ctgtccactc | 840 |
| cctcagctcg | gacaccttct | ctcctcccag | atccgagtaa | ctcccaatct | tctctctgca | 900 |
| gagcgcaaat | gttgtgtcga | gtgcccaccg | tgcccaggta | agccagccca | ggcctcgccc | 960 |
| tccagctcaa | ggcgggacag | gtgccctaga | gtagcctgca | tccagggaca | ggccccagct | 1020 |
| gggtgctgac | acgtccacct | ccatctcttc | ctcagcacca | cctgtggcag | gaccgtcagt | 1080 |
| cttcctcttc | cccccaaaac | ccaaggacac | cctcatgatc | tcccggaccc | ctgaggtcac | 1140 |
| gtgcgtggtg | gtggacgtga | gccacgaaga | ccccgaggtc | cagttcaact | ggtacgtgga | 1200 |
| cggcgtggag | gtgcataatg | ccaagacaaa | gccacgggag | gagcagttca | acagcacgtt | 1260 |
| ccgtgtggtc | agcgtcctca | ccgttgtgca | ccaggactgg | ctgaacggca | aggagtacaa | 1320 |
| gtgcaaggtc | tccaacaaag | gcctcccagc | ccccatcgag | aaaaccatct | ccaaaaccaa | 1380 |
| aggtgggacc | cgcggggtat | gagggccaca | tggacagagg | ccggctcggc | ccaccctctg | 1440 |
| ccctgggagt | gaccgctgtg | ccaacctctg | tccctacagg | gcagcccga | gaaccacagg | 1500 |
| tgtacaccct | gcccccatcc | cgggaggaga | tgaccaagaa | ccaggtcagc | ctgacctgcc | 1560 |
| tggtcaaagg | cttctacccc | agcgacatcg | ccgtggagtg | ggagagcaat | gggcagccgg | 1620 |
| agaacaacta | caagaccaca | cctcccatgc | tggactccga | cggctccttc | ttcctctaca | 1680 |

```
gcaagctcac cgtggacaag agcaggtggc agcaggggaa cgtcttctca tgctccgtga    1740
tgcatgaggc tctgcacaac cactacacgc agaagagcct ctccctgtct ccgggtaaat    1800
gagtgccacg gccggcaagc ccccgctccc caggctctcg gggtcgcgtg aggatgcttg    1860
gcacgtaccc cgtgtacata cttcccaggc acccagcatg gaaataaagc acccagcgct    1920
gccctgggcc cctgcgagac tgtgatggtt ctttccgtgg gtcaggccga gtctgaggcc    1980
tgagtggcat gagggaggca gagtgggtc                                      2009
```

<210> SEQ ID NO 32
<211> LENGTH: 326
<212> TYPE: PRT
<213> ORGANISM: Homo sapiens
<220> FEATURE:
<223> OTHER INFORMATION: Human IgG2

<400> SEQUENCE: 32

```
Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300
```

Ser Val Met His Glu Ala Leu His Asn His Tyr Thr Gln Lys Ser Leu
305                 310                 315                 320

Ser Leu Ser Pro Gly Lys
            325

<210> SEQ ID NO 33
<211> LENGTH: 1224
<212> TYPE: DNA
<213> ORGANISM: Homo sapiens
<220> FEATURE:
<223> OTHER INFORMATION: sFcRIIIAG2-V1

<400> SEQUENCE: 33

| | | | | | |
|---|---|---|---|---|---|
| atgcggactg | aagatctccc | caaggctgtg | gtgttcctgg | agcctcaatg | gtacagggtg | 60 |
| ctcgagaagg | acagtgtgac | tctgaagtgc | cagggagcct | actcccctga | ggacaattcc | 120 |
| acacagtggt | ttcacaatga | gagcctcatc | tcaagccagg | cctcgagcta | cttcattgac | 180 |
| gctgccacag | tcgacgacag | tggagagtac | aggtgccaga | caaacctctc | caccctcagt | 240 |
| gacccggtgc | agctagaagt | ccatatcggc | tggctgttgc | tccaggcccc | tcggtgggtg | 300 |
| ttcaaggagg | aagaccctat | tcacctgagg | tgtcacagct | ggaagaacac | tgctctgcat | 360 |
| aaggtcacat | atttacagaa | tggcaaaggc | aggaagtatt | tcatcataa | ttctgacttc | 420 |
| tacattccaa | agccacact | caaagacagc | ggctcctact | tctgcagggg | gcttgttggg | 480 |
| agtaaaaatg | tgtcttcaga | gactgtgaac | atcaccatca | ctcaaggtgg | cggaggatca | 540 |
| gagcgcaaat | gttgtgtcga | gtgcccaccg | tgcccagcac | cacctgtggc | aggaccgtca | 600 |
| gtcttcctct | tccccccaaa | acccaaggac | accctcatga | tctcccggac | ccctgaggtc | 660 |
| acgtgcgtgg | tggtggacgt | gagccacgaa | gaccccgagg | tccagttcaa | ctggtacgtg | 720 |
| gacggcatgg | aggtgcataa | tgccaagaca | aagccacggg | aggagcagtt | caacagcacg | 780 |
| ttccgtgtgg | tcagcgtcct | caccgtcgtg | caccaggact | ggctgaacgg | caaggagtac | 840 |
| aagtgcaagg | tctccaacaa | aggcctccca | gcccccatcg | agaaaaccat | ctccaaaacc | 900 |
| aaagggcagc | cccgagaacc | acaggtgtac | accctgcccc | catcccggga | ggagatgacc | 960 |
| aagaaccagg | tcagcctgac | ctgcctggtc | aaaggcttct | accccagcga | catcgccgtg | 1020 |
| gagtgggaga | gcaatgggca | gccggagaac | aactacaaga | ccacacctcc | catgctggac | 1080 |
| tccgacggct | ccttcttcct | ctacagcaag | ctcaccgtgg | acaagagcag | gtggcagcag | 1140 |
| gggaacgtct | tctcatgctc | cgtgatgcat | gaggctctgc | acaaccacta | cacacagaag | 1200 |
| agcctctccc | tgtctccggg | taaa | | | | 1224 |

<210> SEQ ID NO 34
<211> LENGTH: 408
<212> TYPE: PRT
<213> ORGANISM: Homo sapiens
<220> FEATURE:
<223> OTHER INFORMATION: sFcRIIIAG2-V1

<400> SEQUENCE: 34

Met Arg Thr Glu Asp Leu Pro Lys Ala Val Val Phe Leu Glu Pro Gln
 1               5                  10                  15

Trp Tyr Arg Val Leu Glu Lys Asp Ser Val Thr Leu Lys Cys Gln Gly
            20                  25                  30

Ala Tyr Ser Pro Glu Asp Asn Ser Thr Gln Trp Phe His Asn Glu Ser
        35                  40                  45

Leu Ile Ser Ser Gln Ala Ser Ser Tyr Phe Ile Asp Ala Ala Thr Val
    50                  55                  60

```
Asp Asp Ser Gly Glu Tyr Arg Cys Gln Thr Asn Leu Ser Thr Leu Ser
 65                  70                  75                  80

Asp Pro Val Gln Leu Glu Val His Ile Gly Trp Leu Leu Leu Gln Ala
                 85                  90                  95

Pro Arg Trp Val Phe Lys Glu Glu Asp Pro Ile His Leu Arg Cys His
            100                 105                 110

Ser Trp Lys Asn Thr Ala Leu His Lys Val Thr Tyr Leu Gln Asn Gly
        115                 120                 125

Lys Gly Arg Lys Tyr Phe His His Asn Ser Asp Phe Tyr Ile Pro Lys
    130                 135                 140

Ala Thr Leu Lys Asp Ser Gly Ser Tyr Phe Cys Arg Gly Leu Val Gly
145                 150                 155                 160

Ser Lys Asn Val Ser Ser Glu Thr Val Asn Ile Thr Ile Thr Gln Gly
                165                 170                 175

Gly Gly Gly Ser Glu Arg Lys Cys Cys Val Glu Cys Pro Pro Cys Pro
            180                 185                 190

Ala Pro Pro Val Ala Gly Pro Ser Val Phe Leu Phe Pro Pro Lys Pro
        195                 200                 205

Lys Asp Thr Leu Met Ile Ser Arg Thr Pro Glu Val Thr Cys Val Val
    210                 215                 220

Val Asp Val Ser His Glu Asp Pro Glu Val Gln Phe Asn Trp Tyr Val
225                 230                 235                 240

Asp Gly Met Glu Val His Asn Ala Lys Thr Lys Pro Arg Glu Glu Gln
                245                 250                 255

Phe Asn Ser Thr Phe Arg Val Val Ser Val Leu Thr Val Val His Gln
            260                 265                 270

Asp Trp Leu Asn Gly Lys Glu Tyr Lys Cys Lys Val Ser Asn Lys Gly
        275                 280                 285

Leu Pro Ala Pro Ile Glu Lys Thr Ile Ser Lys Thr Lys Gly Gln Pro
    290                 295                 300

Arg Glu Pro Gln Val Tyr Thr Leu Pro Pro Ser Arg Glu Glu Met Thr
305                 310                 315                 320

Lys Asn Gln Val Ser Leu Thr Cys Leu Val Lys Gly Phe Tyr Pro Ser
                325                 330                 335

Asp Ile Ala Val Glu Trp Glu Ser Asn Gly Gln Pro Glu Asn Asn Tyr
            340                 345                 350

Lys Thr Thr Pro Pro Met Leu Asp Ser Asp Gly Ser Phe Phe Leu Tyr
        355                 360                 365

Ser Lys Leu Thr Val Asp Lys Ser Arg Trp Gln Gln Gly Asn Val Phe
370                 375                 380

Ser Cys Ser Val Met His Glu Ala Leu His Asn His Tyr Thr Gln Lys
385                 390                 395                 400

Ser Leu Ser Leu Ser Pro Gly Lys
                405

<210> SEQ ID NO 35
<211> LENGTH: 1224
<212> TYPE: DNA
<213> ORGANISM: Homo sapiens
<220> FEATURE:
<223> OTHER INFORMATION: sFcRIIIAG2-V2

<400> SEQUENCE: 35
atgcggactg aagatctccc caaggctgtg gtgttcctgg agcctcaatg gtacagggtg      60
```

-continued

```
ctcgagaagg acagtgtgac tctgaagtgc cagggagcct actcccctga ggacaattcc    120
acacagtggt ttcacaatga gagcctcatc tcaagccagg cctcgagcta cttcattgac    180
gctgccacag tcgacgacag tggagagtac aggtgccaga caaacctctc caccctcagt    240
gacccggtgc agctagaagt ccatatcggc tggctgttgc tccaggcccc tcggtgggtg    300
ttcaaggagg aagaccctat tcacctgagg tgtcacagct ggaagaacac tgctctgcat    360
aaggtcacat atttacagaa tggcaaaggc aggaagtatt tcatcataa ttctgacttc    420 tacattccaa aagccacact caaagacagc ggctcctact tctgcagggg gcttgttggg    480
agtaaaaatg tgtcttcaga gactgtgacc atcaccatca ctcaaggtgg cggaggatca    540
gagcgcaaat gttgtgtcga gtgcccaccg tgcccagcac acctgtggc aggaccgtca    600 gtcttcctct ccccccaaa acccaaggac accctcatga tctcccggac ccctgaggtc    660
acgtgcgtgg tggtggacgt gagccacgaa gaccccgagg tccagttcaa ctggtacgtg    720
gacggcatgg aggtgcataa tgccaagaca aagccacggg aggagcagtt caacagcacg    780
ttccgtgtgg tcagcgtcct caccgtcgtg caccaggact ggctgaacgg caaggagtac    840
aagtgcaagg tctccaacaa aggcctccca gcccccatcg agaaaaccat ctccaaaacc    900
aaagggcagc cccgagaacc acaggtgtac accctgcccc catcccggga ggagatgacc    960
aagaaccagg tcagcctgac ctgcctggtc aaaggcttct accccagcga catcgccgtg   1020
gagtgggaga gcaatgggca gccggagaac aactacaaga ccacacctcc catgctggac   1080
tccgacggct ccttcttcct ctacagcaag ctcaccgtgg acaagagcag gtggcagcag   1140
gggaacgtct tctcatgctc cgtgatgcat gaggctctgc acaaccacta cacacagaag   1200
agcctctccc tgtctccggg taaa                                           1224
```

<210> SEQ ID NO 36
<211> LENGTH: 408
<212> TYPE: PRT
<213> ORGANISM: Homo sapiens
<220> FEATURE:
<223> OTHER INFORMATION: sFcRIIIAG2-V2

<400> SEQUENCE: 36

```
Met Arg Thr Glu Asp Leu Pro Lys Ala Val Val Phe Leu Glu Pro Gln
 1               5                  10                  15

Trp Tyr Arg Val Leu Glu Lys Asp Ser Val Thr Leu Lys Cys Gln Gly
                20                  25                  30

Ala Tyr Ser Pro Glu Asp Asn Ser Thr Gln Trp Phe His Asn Glu Ser
            35                  40                  45

Leu Ile Ser Ser Gln Ala Ser Ser Tyr Phe Ile Asp Ala Ala Thr Val
 50                  55                  60

Asp Asp Ser Gly Glu Tyr Arg Cys Gln Thr Asn Leu Ser Thr Leu Ser
 65                  70                  75                  80

Asp Pro Val Gln Leu Glu Val His Ile Gly Trp Leu Leu Leu Gln Ala
                 85                  90                  95

Pro Arg Trp Val Phe Lys Glu Glu Asp Pro Ile His Leu Arg Cys His
            100                 105                 110

Ser Trp Lys Asn Thr Ala Leu His Lys Val Thr Tyr Leu Gln Asn Gly
        115                 120                 125

Lys Gly Arg Lys Tyr Phe His His Asn Ser Asp Phe Tyr Ile Pro Lys
    130                 135                 140

Ala Thr Leu Lys Asp Ser Gly Ser Tyr Phe Cys Arg Gly Leu Val Gly
145                 150                 155                 160
```

```
Ser Lys Asn Val Ser Ser Glu Thr Val Thr Ile Thr Ile Thr Gln Gly
            165                 170                 175
Gly Gly Gly Ser Glu Arg Lys Cys Cys Val Glu Cys Pro Pro Cys Pro
            180                 185                 190
Ala Pro Pro Val Ala Gly Pro Ser Val Phe Leu Phe Pro Pro Lys Pro
            195                 200                 205
Lys Asp Thr Leu Met Ile Ser Arg Thr Pro Glu Val Thr Cys Val Val
            210                 215                 220
Val Asp Val Ser His Glu Asp Pro Glu Val Gln Phe Asn Trp Tyr Val
225                 230                 235                 240
Asp Gly Met Glu Val His Asn Ala Lys Thr Lys Pro Arg Glu Glu Gln
                245                 250                 255
Phe Asn Ser Thr Phe Arg Val Val Ser Val Leu Thr Val Val His Gln
                260                 265                 270
Asp Trp Leu Asn Gly Lys Glu Tyr Lys Cys Lys Val Ser Asn Lys Gly
                275                 280                 285
Leu Pro Ala Pro Ile Glu Lys Thr Ile Ser Lys Thr Lys Gly Gln Pro
            290                 295                 300
Arg Glu Pro Gln Val Tyr Thr Leu Pro Pro Ser Arg Glu Glu Met Thr
305                 310                 315                 320
Lys Asn Gln Val Ser Leu Thr Cys Leu Val Lys Gly Phe Tyr Pro Ser
                325                 330                 335
Asp Ile Ala Val Glu Trp Glu Ser Asn Gly Gln Pro Glu Asn Asn Tyr
                340                 345                 350
Lys Thr Thr Pro Pro Met Leu Asp Ser Asp Gly Ser Phe Phe Leu Tyr
                355                 360                 365
Ser Lys Leu Thr Val Asp Lys Ser Arg Trp Gln Gln Gly Asn Val Phe
            370                 375                 380
Ser Cys Ser Val Met His Glu Ala Leu His Asn His Tyr Thr Gln Lys
385                 390                 395                 400
Ser Leu Ser Leu Ser Pro Gly Lys
                405
```

<210> SEQ ID NO 37
<211> LENGTH: 1230
<212> TYPE: DNA
<213> ORGANISM: Homo sapiens
<220> FEATURE:
<223> OTHER INFORMATION: sFcRIIIAG2-V3

<400> SEQUENCE: 37

```
atgcggactg aagatctccc caaggctgtg gtgttcctgg agcctcaatg gtacagggtg    60
ctcgagaagg acagtgtgac tctgaagtgc cagggagcct actcccctga ggacaattcc   120
acacagtggt ttcacaatga gagcctcatc tcaagccagg cctcgagcta cttcattgac   180
gctgccacag tcgacgacag tggagagtac aggtgccaga caaacctctc caccctcagt   240
gacccggtgc agctagaagt ccatatcggc tggctgttgc tccaggcccc tcggtgggtg   300
ttcaaggagg aagaccctat tcacctgagg tgtcacagct ggaagaacac tgctctgcat   360
aaggtcacat atttacagaa tggcaaaggc aggaagtatt tcatcataa ttctgacttc   420
tacattccaa aagccacact caaagacagc ggctcctact tctgcagggg gcttgttggg   480
agtaaaaatg tgtcttcaga gactgtgaac atcactgtcc aagctcccag ctcttcaccc   540
atggaggagc gcaaatgttg tgtcgagtgc ccaccgtgcc cagcaccacc tgtggcagga   600
```

```
ccgtcagtct tcctcttccc cccaaaaccc aaggacaccc tcatgatctc ccggaccct      660 gaggtcacgt gcgtggtggt ggacgtgagc cacgaagacc ccgaggtcca gttcaactgg     720
tacgtggacg gcatggaggt gcataatgcc aagacaaagc cacgggagga gcagttcaac    780
agcacgttcc gtgtggtcag cgtcctcacc gtcgtgcacc aggactggct gaacggcaag    840
gagtacaagt gcaaggtctc caacaaaggc ctcccagccc ccatcgagaa aaccatctcc   900
aaaaccaaag ggcagccccg agaaccacag gtgtacaccc tgcccccatc ccgggaggag    960
atgaccaaga accaggtcag cctgacctgc ctggtcaaag gcttctaccc cagcgacatc   1020
gccgtggagt gggagagcaa tgggcagccg gagaacaact acaagaccac acctcccatg   1080
ctggactccg acggctcctt cttcctctac agcaagctca ccgtggacaa gagcaggtgg   1140
cagcagggga acgtcttctc atgctccgtg atgcatgagg ctctgcacaa ccactacaca   1200
cagaagagcc tctccctgtc tccgggtaaa                                    1230
```

<210> SEQ ID NO 38
<211> LENGTH: 410
<212> TYPE: PRT
<213> ORGANISM: Homo sapiens
<220> FEATURE:
<223> OTHER INFORMATION: sFcRIIIAG2-V3

<400> SEQUENCE: 38

```
Met Arg Thr Glu Asp Leu Pro Lys Ala Val Val Phe Leu Glu Pro Gln
 1               5                  10                  15

Trp Tyr Arg Val Leu Glu Lys Asp Ser Val Thr Leu Lys Cys Gln Gly
            20                  25                  30

Ala Tyr Ser Pro Glu Asp Asn Ser Thr Gln Trp Phe His Asn Glu Ser
        35                  40                  45

Leu Ile Ser Ser Gln Ala Ser Ser Tyr Phe Ile Asp Ala Ala Thr Val
    50                  55                  60

Asp Asp Ser Gly Glu Tyr Arg Cys Gln Thr Asn Leu Ser Thr Leu Ser
65                  70                  75                  80

Asp Pro Val Gln Leu Glu Val His Ile Gly Trp Leu Leu Leu Gln Ala
                85                  90                  95

Pro Arg Trp Val Phe Lys Glu Glu Asp Pro Ile His Leu Arg Cys His
            100                 105                 110

Ser Trp Lys Asn Thr Ala Leu His Lys Val Thr Tyr Leu Gln Asn Gly
        115                 120                 125

Lys Gly Arg Lys Tyr Phe His His Asn Ser Asp Phe Tyr Ile Pro Lys
    130                 135                 140

Ala Thr Leu Lys Asp Ser Gly Ser Tyr Phe Cys Arg Gly Leu Val Gly
145                 150                 155                 160

Ser Lys Asn Val Ser Ser Glu Thr Val Asn Ile Thr Val Gln Ala Pro
                165                 170                 175

Ser Ser Ser Pro Met Glu Glu Arg Lys Cys Cys Val Glu Cys Pro Pro
            180                 185                 190

Cys Pro Ala Pro Pro Val Ala Gly Pro Ser Val Phe Leu Phe Pro Pro
        195                 200                 205

Lys Pro Lys Asp Thr Leu Met Ile Ser Arg Thr Pro Glu Val Thr Cys
    210                 215                 220

Val Val Val Asp Val Ser His Glu Asp Pro Glu Val Gln Phe Asn Trp
225                 230                 235                 240

Tyr Val Asp Gly Met Glu Val His Asn Ala Lys Thr Lys Pro Arg Glu
                245                 250                 255
```

```
Glu Gln Phe Asn Ser Thr Phe Arg Val Val Ser Val Leu Thr Val Val
                260                 265                 270

His Gln Asp Trp Leu Asn Gly Lys Glu Tyr Lys Cys Lys Val Ser Asn
            275                 280                 285

Lys Gly Leu Pro Ala Pro Ile Glu Lys Thr Ile Ser Lys Thr Lys Gly
        290                 295                 300

Gln Pro Arg Glu Pro Gln Val Tyr Thr Leu Pro Pro Ser Arg Glu Glu
305                 310                 315                 320

Met Thr Lys Asn Gln Val Ser Leu Thr Cys Leu Val Lys Gly Phe Tyr
                325                 330                 335

Pro Ser Asp Ile Ala Val Glu Trp Glu Ser Asn Gly Gln Pro Glu Asn
            340                 345                 350

Asn Tyr Lys Thr Thr Pro Pro Met Leu Asp Ser Asp Gly Ser Phe Phe
        355                 360                 365

Leu Tyr Ser Lys Leu Thr Val Asp Lys Ser Arg Trp Gln Gln Gly Asn
370                 375                 380

Val Phe Ser Cys Ser Val Met His Glu Ala Leu His Asn His Tyr Thr
385                 390                 395                 400

Gln Lys Ser Leu Ser Leu Ser Pro Gly Lys
                405                 410

<210> SEQ ID NO 39
<211> LENGTH: 1230
<212> TYPE: DNA
<213> ORGANISM: Homo sapiens
<220> FEATURE:
<223> OTHER INFORMATION: sFcRIIIAG2-V4

<400> SEQUENCE: 39
atgcggactg aagatctccc caaggctgtg gtgttcctgg agcctcaatg gtacagggtg      60
ctcgagaagg acagtgtgac tctgaagtgc cagggagcct actcccctga ggacaattcc     120
acacagtggt ttcacaatga gagcctcatc tcaagccagg cctcgagcta cttcattgac     180
gctgccacag tcgacgacag tggagagtac aggtgccaga caaacctctc caccctcagt     240
gacccggtgc agctagaagt ccatatcggc tggctgttgc tccaggcccc tcggtgggtg     300
ttcaaggagg aagaccctat tcacctgagg tgtcacagct ggaagaacac tgctctgcat     360
aaggtcacat atttacagaa tggcaaaggc aggaagtatt tccatcataa ttctgacttc     420
tacattccaa aagccacact caaagacagc ggctcctact ctgcaggggg cttgttgggg     480
agtaaaaatg tgtcttcaga gactgtgacc atcactgtcc aagctcccag ctcttcaccc     540
atggaggagc gcaaatgttg tgtcgagtgc ccaccgtgcc cagcaccacc tgtggcagga     600
ccgtcagtct tcctcttccc cccaaaaccc aaggacaccc tcatgatctc ccggacccct     660
gaggtcacgt gcgtggtggt ggacgtgagc cacgaagacc ccgaggtcca gttcaactgg     720
tacgtggacg gcatggaggt gcataatgcc aagacaaagc cacgggagga gcagttcaac     780
agcacgttcc gtgtggtcag cgtcctcacc gtcgtgcacc aggactggct gaacggcaag     840
gagtacaagt gcaaggtctc caacaaaggc ctcccagccc ccatcgagaa aaccatctcc     900
aaaaccaaag ggcagccccg agaaccacag gtgtacaccc tgcccccatc ccgggaggag     960
atgaccaaga accaggtcag cctgacctgc ctggtcaaag gcttctaccc cagcgacatc    1020
gccgtggagt gggagagcaa tgggcagccg gagaacaact acaagaccac acctcccatg    1080
ctggactccg acggctcctt cttcctctac agcaagctca ccgtggacaa gagcaggtgg    1140
```

-continued

```
cagcagggga acgtcttctc atgctccgtg atgcatgagg ctctgcacaa ccactacaca    1200
cagaagagcc tctccctgtc tccgggtaaa                                     1230
```

<210> SEQ ID NO 40
<211> LENGTH: 410
<212> TYPE: PRT
<213> ORGANISM: Homo sapiens
<220> FEATURE:
<223> OTHER INFORMATION: sFcRIIIAG2-V4

<400> SEQUENCE: 40

```
Met Arg Thr Glu Asp Leu Pro Lys Ala Val Val Phe Leu Glu Pro Gln
  1               5                  10                  15

Trp Tyr Arg Val Leu Glu Lys Asp Ser Val Thr Leu Lys Cys Gln Gly
             20                  25                  30

Ala Tyr Ser Pro Glu Asp Asn Ser Thr Gln Trp Phe His Asn Glu Ser
         35                  40                  45

Leu Ile Ser Ser Gln Ala Ser Ser Tyr Phe Ile Asp Ala Ala Thr Val
     50                  55                  60

Asp Asp Ser Gly Glu Tyr Arg Cys Gln Thr Asn Leu Ser Thr Leu Ser
 65                  70                  75                  80

Asp Pro Val Gln Leu Glu Val His Ile Gly Trp Leu Leu Leu Gln Ala
                 85                  90                  95

Pro Arg Trp Val Phe Lys Glu Glu Asp Pro Ile His Leu Arg Cys His
            100                 105                 110

Ser Trp Lys Asn Thr Ala Leu His Lys Val Thr Tyr Leu Gln Asn Gly
        115                 120                 125

Lys Gly Arg Lys Tyr Phe His His Asn Ser Asp Phe Tyr Ile Pro Lys
    130                 135                 140

Ala Thr Leu Lys Asp Ser Gly Ser Tyr Phe Cys Arg Gly Leu Val Gly
145                 150                 155                 160

Ser Lys Asn Val Ser Ser Glu Thr Val Thr Ile Thr Val Gln Ala Pro
                165                 170                 175

Ser Ser Ser Pro Met Glu Glu Arg Lys Cys Cys Val Glu Cys Pro Pro
            180                 185                 190

Cys Pro Ala Pro Pro Val Ala Gly Pro Ser Val Phe Leu Phe Pro Pro
        195                 200                 205

Lys Pro Lys Asp Thr Leu Met Ile Ser Arg Thr Pro Glu Val Thr Cys
    210                 215                 220

Val Val Val Asp Val Ser His Glu Asp Pro Glu Val Gln Phe Asn Trp
225                 230                 235                 240

Tyr Val Asp Gly Met Glu Val His Asn Ala Lys Thr Lys Pro Arg Glu
                245                 250                 255

Glu Gln Phe Asn Ser Thr Phe Arg Val Val Ser Val Leu Thr Val Val
            260                 265                 270

His Gln Asp Trp Leu Asn Gly Lys Glu Tyr Lys Cys Lys Val Ser Asn
        275                 280                 285

Lys Gly Leu Pro Ala Pro Ile Glu Lys Thr Ile Ser Lys Thr Lys Gly
    290                 295                 300

Gln Pro Arg Glu Pro Gln Val Tyr Thr Leu Pro Pro Ser Arg Glu Glu
305                 310                 315                 320

Met Thr Lys Asn Gln Val Ser Leu Thr Cys Leu Val Lys Gly Phe Tyr
                325                 330                 335

Pro Ser Asp Ile Ala Val Glu Trp Glu Ser Asn Gly Gln Pro Glu Asn
            340                 345                 350
```

```
Asn Tyr Lys Thr Thr Pro Met Leu Asp Ser Asp Gly Ser Phe Phe
            355                 360                 365

Leu Tyr Ser Lys Leu Thr Val Asp Lys Ser Arg Trp Gln Gln Gly Asn
        370                 375                 380

Val Phe Ser Cys Ser Val Met His Glu Ala Leu His Asn His Tyr Thr
385                 390                 395                 400

Gln Lys Ser Leu Ser Leu Ser Pro Gly Lys
            405                 410

<210> SEQ ID NO 41
<211> LENGTH: 1227
<212> TYPE: DNA
<213> ORGANISM: Homo sapiens
<220> FEATURE:
<223> OTHER INFORMATION: sFcRIIBG2-N297Q

<400> SEQUENCE: 41
```

| | | | | |
|---|---|---|---|---|
| acacctgcag ctcccccaaa ggctgtgctg aaactcgagc cccagtggat caacgtgctc | | | | 60 |
| caggaggact ctgtgactct gacatgccgg gggactcaca gccctgagag cgactccatt | | | | 120 |
| cagtggttcc acaatgggaa tctcattccc acccacacgc agcccagcta caggttcaag | | | | 180 |
| gccaacaaca tgacagcgg ggagtacacg tgccagactg ccagaccag cctcagcgac | | | | 240 |
| cctgtgcatc tgactgtgct ttctgagtgg ctggtgctcc agacccctca cctggagttc | | | | 300 |
| caggagggag aaaccatcgt gctgaggtgc acagctgga aggacaagcc tctggtcaag | | | | 360 |
| gtcacattct tccagaatgg aaaatccaag aatttttccc gttcggatcc caacttctcc | | | | 420 |
| atcccacaag caaaccacag tcacagtggt gattaccact gcacaggaaa cataggctac | | | | 480 |
| acgctgttct catccaagcc tgtgaccatc actgtccaag ctcccagctc ttcacccatg | | | | 540 |
| gaggagcgca atgttgtgt cgagtgccca ccgtgcccag caccacctgt ggcaggaccg | | | | 600 |
| tcagtcttcc tcttcccccc aaaacccaag gacaccctca tgatctcccg gacccctgag | | | | 660 |
| gtcacgtgcg tggtggtgga cgtgagccac gaagaccccg aggtccagtt caactggtac | | | | 720 |
| gtggacggca tggaggtgca taatgccaag acaaagccac gggaggagca gttccagagc | | | | 780 |
| acgttccgtg tggtcagcgt cctcaccgtc gtgcaccagg actggctgaa cggcaaggag | | | | 840 |
| tacaagtgca aggtctccaa caaaggcctc ccagccccca tcgagaaaac catctccaaa | | | | 900 |
| accaaagggc agccccgaga accacaggtg tacaccctgc ccccatcccg ggaggagatg | | | | 960 |
| accaagaacc aggtcagcct gacctgcctg gtcaaaggct tctacccag cgacatcgcc | | | | 1020 |
| gtggagtggg agagcaatgg gcagccggag aacaactaca agaccacacc tcccatgctg | | | | 1080 |
| gactccgacg gctccttctt cctctacagc aagctcaccg tggacaagag caggtggcag | | | | 1140 |
| caggggaacg tcttctcatg ctctgtgatg catgaggctc tgcacaacca ctacacacag | | | | 1200 |
| aagagcctct ccctgtctcc gggtaaa | | | | 1227 |

```
<210> SEQ ID NO 42
<211> LENGTH: 409
<212> TYPE: PRT
<213> ORGANISM: Homo sapiens
<220> FEATURE:
<223> OTHER INFORMATION: sFcRIIBG2-N297Q

<400> SEQUENCE: 42

Thr Pro Ala Ala Pro Pro Lys Ala Val Leu Lys Leu Glu Pro Gln Trp
1               5                   10                  15

Ile Asn Val Leu Gln Glu Asp Ser Val Thr Leu Thr Cys Arg Gly Thr
```

-continued

```
                  20                  25                  30
His Ser Pro Glu Ser Asp Ser Ile Gln Trp Phe His Asn Gly Asn Leu
            35                  40                  45
Ile Pro Thr His Thr Gln Pro Ser Tyr Arg Phe Lys Ala Asn Asn Asn
 50                  55                  60
Asp Ser Gly Glu Tyr Thr Cys Gln Thr Gly Gln Thr Ser Leu Ser Asp
 65                  70                  75                  80
Pro Val His Leu Thr Val Leu Ser Glu Trp Leu Val Leu Gln Thr Pro
                85                  90                  95
His Leu Glu Phe Gln Glu Gly Thr Ile Val Leu Arg Cys His Ser
            100                 105                 110
Trp Lys Asp Lys Pro Leu Val Lys Val Thr Phe Phe Gln Asn Gly Lys
            115                 120                 125
Ser Lys Lys Phe Ser Arg Ser Asp Pro Asn Phe Ser Ile Pro Gln Ala
            130                 135                 140
Asn His Ser His Ser Gly Asp Tyr His Cys Thr Gly Asn Ile Gly Tyr
145                 150                 155                 160
Thr Leu Phe Ser Ser Lys Pro Val Thr Ile Thr Val Gln Ala Pro Ser
                165                 170                 175
Ser Ser Pro Met Glu Glu Arg Lys Cys Cys Val Glu Cys Pro Pro Cys
                180                 185                 190
Pro Ala Pro Pro Val Ala Gly Pro Ser Val Phe Leu Phe Pro Pro Lys
            195                 200                 205
Pro Lys Asp Thr Leu Met Ile Ser Arg Thr Pro Glu Val Thr Cys Val
 210                 215                 220
Val Val Asp Val Ser His Glu Asp Pro Glu Val Gln Phe Asn Trp Tyr
 225                 230                 235                 240
Val Asp Gly Met Glu Val His Asn Ala Lys Thr Lys Pro Arg Glu Glu
                245                 250                 255
Gln Phe Gln Ser Thr Phe Arg Val Val Ser Val Leu Thr Val Val His
                260                 265                 270
Gln Asp Trp Leu Asn Gly Lys Glu Tyr Lys Cys Lys Val Ser Asn Lys
            275                 280                 285
Gly Leu Pro Ala Pro Ile Glu Lys Thr Ile Ser Lys Thr Lys Gly Gln
 290                 295                 300
Pro Arg Glu Pro Gln Val Tyr Thr Leu Pro Pro Ser Arg Glu Glu Met
 305                 310                 315                 320
Thr Lys Asn Gln Val Ser Leu Thr Cys Leu Val Lys Gly Phe Tyr Pro
                325                 330                 335
Ser Asp Ile Ala Val Glu Trp Glu Ser Asn Gly Gln Pro Glu Asn Asn
                340                 345                 350
Tyr Lys Thr Thr Pro Pro Met Leu Asp Ser Asp Gly Ser Phe Phe Leu
            355                 360                 365
Tyr Ser Lys Leu Thr Val Asp Lys Ser Arg Trp Gln Gln Gly Asn Val
            370                 375                 380
Phe Ser Cys Ser Val Met His Glu Ala Leu His Asn His Tyr Thr Gln
385                 390                 395                 400
Lys Ser Leu Ser Leu Ser Pro Gly Lys
                405

<210> SEQ ID NO 43
<211> LENGTH: 5
<212> TYPE: PRT
<213> ORGANISM: Homo sapiens
```

```
<220> FEATURE:
<223> OTHER INFORMATION: FcgammaRIIIA F/G loop region fragment

<400> SEQUENCE: 43

Gly Ser Lys Asn Val
1               5

<210> SEQ ID NO 44
<211> LENGTH: 5
<212> TYPE: PRT
<213> ORGANISM: Artificial Sequence
<220> FEATURE:
<223> OTHER INFORMATION: FcgammaRIIIA F/G loop region mutant

<400> SEQUENCE: 44

Gly Tyr Thr Leu Phe
1               5

<210> SEQ ID NO 45
<211> LENGTH: 16
<212> TYPE: PRT
<213> ORGANISM: Homo sapiens
<220> FEATURE:
<223> OTHER INFORMATION: FcgammaRIIIA-G2 extracellular domain C-terminal
      fragment

<400> SEQUENCE: 45

Leu Ala Val Ser Thr Ile Ser Ser Phe Phe Pro Gly Tyr Gln Val
1               5                   10                  15

<210> SEQ ID NO 46
<211> LENGTH: 5
<212> TYPE: PRT
<213> ORGANISM: Artificial Sequence
<220> FEATURE:
<223> OTHER INFORMATION: flexible linker sequence

<400> SEQUENCE: 46

Gly Gly Gly Gly Ser
1               5

<210> SEQ ID NO 47
<211> LENGTH: 20
<212> TYPE: PRT
<213> ORGANISM: Homo sapiens
<220> FEATURE:
<223> OTHER INFORMATION: FcgammaRIIIA-G2 extracellular domain C-terminal
      fragment

<400> SEQUENCE: 47

Ile Thr Gln Gly Leu Ala Val Ser Thr Ile Ser Ser Phe Phe Pro Pro
1               5                   10                  15

Gly Tyr Gln Val
            20

<210> SEQ ID NO 48
<211> LENGTH: 10
<212> TYPE: PRT
<213> ORGANISM: Homo sapiens
<220> FEATURE:
<223> OTHER INFORMATION: FcgammaRIIB-G2 extracellular domain C-terminal
      fragment

<400> SEQUENCE: 48

Val Gln Ala Pro Ser Ser Ser Pro Met Glu
1               5                   10
```

```
<210> SEQ ID NO 49
<211> LENGTH: 24
<212> TYPE: PRT
<213> ORGANISM: Homo sapiens
<220> FEATURE:
<223> OTHER INFORMATION: FcgammaRIIIA-G2 wild type subsequence

<400> SEQUENCE: 49

Val Asn Ile Thr Ile Thr Gln Gly Leu Ala Val Ser Thr Ile Ser Ser
 1               5                  10                  15

Phe Phe Pro Pro Gly Tyr Gln Val
                20

<210> SEQ ID NO 50
<211> LENGTH: 12
<212> TYPE: PRT
<213> ORGANISM: Artificial Sequence
<220> FEATURE:
<223> OTHER INFORMATION: FcgammaRIIIA-G2, V1 subsequence

<400> SEQUENCE: 50

Val Asn Ile Thr Ile Thr Gln Gly Gly Gly Gly Ser
 1               5                  10

<210> SEQ ID NO 51
<211> LENGTH: 12
<212> TYPE: PRT
<213> ORGANISM: Artificial Sequence
<220> FEATURE:
<223> OTHER INFORMATION: FcgammaRIIIA-G2, V2 subsequence

<400> SEQUENCE: 51

Val Thr Ile Thr Ile Thr Gln Gly Gly Gly Gly Ser
 1               5                  10

<210> SEQ ID NO 52
<211> LENGTH: 14
<212> TYPE: PRT
<213> ORGANISM: Artificial Sequence
<220> FEATURE:
<223> OTHER INFORMATION: FcgammaRIIIA-G2, V3 subsequence

<400> SEQUENCE: 52

Val Asn Ile Thr Val Gln Ala Pro Ser Ser Ser Pro Met Glu
 1               5                  10

<210> SEQ ID NO 53
<211> LENGTH: 14
<212> TYPE: PRT
<213> ORGANISM: Artificial Sequence
<220> FEATURE:
<223> OTHER INFORMATION: FcgammaRIIIA-G2, V4 subsequence

<400> SEQUENCE: 53

Val Thr Ile Thr Val Gln Ala Pro Ser Ser Ser Pro Met Glu
 1               5                  10

<210> SEQ ID NO 54
<211> LENGTH: 14
<212> TYPE: PRT
<213> ORGANISM: Homo sapiens
<220> FEATURE:
<223> OTHER INFORMATION: FcgammaRIIB-G2 wild type subsequence

<400> SEQUENCE: 54

Val Thr Ile Thr Val Gln Ala Pro Ser Ser Ser Pro Met Glu
 1               5                  10
```

FCγRIIB FUSION PROTEINS AND COMPOSITIONS THEREOF

This application claims priority to U.S. Provisional Application Ser. No. 60/439,709 filed on, Jan. 13, 2003 which is incorporated herein by reference in its entirety.

1. FIELD OF THE INVENTION

The present invention relates to molecules, preferably soluble (i.e., not membrane bound) polypeptides, most preferably soluble fusion polypeptides comprising the extracellular soluble regions of an FcγR, derivatives and analogs thereof, and nucleic acids encoding same. Molecules of the invention are particularly useful for the treatment, management, or prevention of, or amelioration of one or more symptoms of, an autoimmune disease, especially for ameliorating serum platelet deficiency associated with immune thrombocytopenic purpura. The invention provides methods and compositions for enhancing the therapeutic efficacy of standard, current or experimental therapies for an autoimmune disease by administering a molecule of the invention.

2. BACKGROUND OF THE INVENTION

2.1 Fcγ Receptors and their Role in the Immune System

The interaction of antibody-antigen complexes with cells of the immune system results in a wide array of responses, ranging from effector functions such as antibody-dependent cytotoxicity, mast cell degranulation, and phagocytosis to immunomodulatory signals such as regulating lymphocyte proliferation and antibody secretion. All these interactions are initiated through the binding of the Fcγ domain of antibodies or immune complexes to specialized cell surface receptors on hematopoietic cells. The diversity of cellular responses triggered by antibodies and immune complexes results from the structural heterogeneity of Fcγ receptors. Fcγ receptors share structurally related ligand binding domains which presumably mediate intracellular signaling.

The Fcγ receptors, members of the immunoglobulin gene superfamily of proteins, are surface glycoproteins that can bind the Fcγ portion of immunoglobulin molecules. Each member of the family recognizes immunoglobulins of one or more isotypes through a recognition domain on the α chain of the Fcγ receptor. Fcγ receptors are defined by their specificity for immunoglobulin subtypes. Fcγ receptors for IgG are referred to as FcγR, for IgE as FcεR, and for IgA as FcαR. Different accessory cells bear Fcγ receptors for antibodies of different isotype, and the isotype of the antibody determines which accessory cells will be engaged in a given response (reviewed by Ravetch J. V. et al. 1991, Annu. Rev. Immunol. 9: 457-92; Gerber J. S. et al. 2001 Microbes and Infection, 3: 131-139; Billadeau D. D. et al. 2002, The Journal of Clinical Investigation, 2(109): 161-1681; Ravetch J. V. et al. 2000, Science, 290: 84-89; Ravetch J. V. et al., 2001 Annu. Rev. Immunol. 19:275-90; Ravetch J. V. 1994, Cell, 78(4): 553-60). The different Fcγ receptors, the cells that express them, and their isotype specificity is summarized in Table 1 (adapted from Immunobiology: The Immune System in Health and Disease, 4$^{th}$ ed. 1999, Elsevier Science Ltd/Garland Publishing, New York).

Fcγ Receptors

Each member of this family is an integral membrane glycoprotein, possessing extracellular domains related to a C2-set of immunoglobulin-related domains, a single membrane spanning domain and an intracytoplasmic domain of variable length. There are three known FcγRs, designated FcγRI(CD64), FcγRII(CD32), and FcγIII(CD16). The three receptors are encoded by distinct genes; however, the extensive homology between the three family members suggest they arose from a common progenitor perhaps by gene duplication.

FcγRII(CD32)

FcγRII proteins are 40 KDa integral membrane glycoproteins which bind only the complexed IgG due to a low affinity for monomeric Ig ($10^6 M^{-1}$). This receptor is the most widely expressed FcγR, present on all hematopoietic cells, including monocytes, macrophages, B cells, NK cells, neutrophils, mast cells, and platelets. FcγRII has only two immunoglobulin-like regions in its immunoglobulin binding chain and hence a much lower affinity for IgG than FcγRI. There are three human FcγRII genes (FcγRII-A, FcγII-B, FcγRII-C), all of which bind IgG in aggregates or immune complexes.

Distinct differences within the cytoplasmic domains of FcγRII-A and FcγRII-B create two functionally heterogenous responses to receptor ligation. The fundamental difference is that the A isoform initiates intracellular signaling leading to cell activation such as phagocytosis and respiratory burst, whereas the B isoform initiates inhibitory signals, e.g., inhibiting B-cell activation.

FcγRIII (CD16)

Due to heterogeneity within this class, the size of FcγRIII ranges between 40 and 80 KDa in mouse and man. Two human genes encode two transcripts, FcγRIIIA, an integral membrane glycoprotein, and FcγRIIIB, a glycosylphosphatidyl-inositol (GPI)-linked version. One murine gene encodes an FcγRIII homologous to the membrane spanning human FcγRIIIA. The FcγRIII shares structral characteristics with each of the other two FcγRs. Like FcγRII, FcγRIII binds IgG with low affinity and contains the corresponding two extracellular Ig-like domains. FcγRIIIA is expressed in macrophages, mast cells and is the lone FcγR in NK cells. The GPI-linked FcγRIIIB is currently known to be expressed only in human neutrophils.

Signaling through FcγRs

Both activating and inhibitory signals are transduced through the FcγRs following ligation. These diametrically opposing functions result from structural differences among the different receptor isoforms. Two distinct domains within the cytoplasmic signaling domains of the receptor called immunoreceptor tyrosine based activation motifs (ITAMs) or immunoreceptor tyrosine based inhibitory motifs (ITIMS) account for the different responses. The recruitment of different cytoplasmic enzymes to these structures dictates the outcome of the FcγR-mediated cellular responses. ITAM-containing FcγR complexes include FcγRI, FcγRIIA, FcγIIIA, whereas ITIM-containing complexes only include FcγRIIB.

Human neutrophils express the FcγRIIA gene. FcγRIIA clustering via immune complexes or specific antibody cross-linking serves to aggregate ITAMs along with receptor-associated kinases which facilitate ITAM phosphorylation. ITAM phosphorylation serves as a docking site for Syk kinase, activation of which results in activation of downstream substrates (e.g., PI₃K). Cellular activation leads to release of proinflammatory mediators.

The FcγRIIB gene is expressed on B lymphocytes; its extracellular domain is 96% identical to FcγRIIA and binds IgG complexes in an indistinguishable manner. The presence of an ITIM in the cytoplasmic domain of FcγRIIB defines this inhibitory subclass of FcγR. Recently the molecular basis of this inhibition was established. When co-ligated along with an activating FcγR, the ITIM in FcγRIIB becomes phosphorylated and attracts the SH2 domain of the inositol polyphosphate 5'-phosphatase (SHIP), which hydrolyzes phosphoinositol messengers released as a consequence of ITAM-containing FcγR-mediated tyrosine kinase activation, consequently preventing the influx of intracellular $Ca^{++}$. Thus crosslinking of FcγRIIB dampens the activating response to FcγR ligation and inhibits cellular responsiveness. B cell activation, B cell proliferation and antibody secretion is thus aborted.

immune response is incapable of removing the offending autoantigen from the body, the immune response persists, and there is a constant supply of new autoantigen, which amplifies the response.

IgG or IgM responses to antigens located on the surface of blood cells lead to the rapid destruction of these cells. An example of this is autoimmune hemolytic anemia, where antibodies against self antigens on red blood cells trigger

TABLE 1

Receptors for the Fcγ Regions of Immunoglobulin Isotypes

| Receptor | FcγRI (CD64) | FcγRII-A (CD32) | FcγRII-B2 (CD32) | FcγRII-B1 (CD32) | FcγRIII (CD16) | FcεRI | FcαRI (CD89) |
|---|---|---|---|---|---|---|---|
| Binding | IgG1 $10^8 M^{-1}$ | IgG1 $2 \times 10^6 M^{-1}$ | IgG1 $2 \times 10^6 M^{-1}$ | IgG1 $2 \times 10^6 M^{-1}$ | IgG1 $5 \times 10^5 M^{-1}$ | IgE $10^{10} M^{-1}$ | IgA1, IgA2 $10^7 M^{-1}$ |
| Cell Type | Macrophages Neutrophils Eosinophils Dendritic cells | Macrophages Neutrophils Eosinophils Dendritic cells Platelets Langerhan cells | Macrophages Neutrophils Eosinophils | B cells Mast cells | NK cells Eosinophil Macrophages Neutrophils Mast Cells | Mast cells Eosinophil Basophils | Macrophages Neutrophils Eosinophils |
| Effect of Ligation | Uptake Stimulation Activation of respiratory burst Induction of killing | Uptake Granule release | Uptake Inhibition of Stimulation | No uptake Inhibition of Stimulation | Induction of Killing | Secretion of granules | Uptake Induction of killing |

2.2 Diseases of Relevance 2.2.1 Autoimmune Diseases

Autoimmune disease occurs when a specific adaptive immune response is mounted against self antigens. The normal consequence of an adaptive immune response against a foreign antigen is the clearance of the antigen from the body. Virus-infected cells, for example, are destroyed by cytotoxic T cells, whereas soluble antigens are cleared by formation of immune complexes of antibody and antigen, which are taken up by cells of the mononuclear phagocytic system such as macrophages. When an adaptive immune response develops against self antigens, however, it is usually impossible for immune effector mechanisms to eliminate the antigen completely, and so a sustained response occurs. The consequence is that the effector pathways of immunity cause chronic inflammatory injury to tissues, which may prove lethal. The mechanisms of tissue damage in autoimmune diseases are essentially the same as those that operate in protective immunity and in hypersensitivity diseases.

It is useful to distinguish two major patterns of autoimmune disease, the diseases in which the expression of autoimmunity is restricted to specific organs of the body, known as 'organ-specific' autoimmune diseases, and those in which many tissues of the body are affected, the 'systemic' autoimmune diseases. Examples of organ-specific autoimmune diseases are Hashimoto's thyroiditis and Graves' disease, each predominantly affecting the thyroid gland, and type I insulin-dependent diabetes mellitus (IDDM), which affects the pancreatic islets. Examples of systemic autoimmune disease are systemic lupus erythematosus (SLE) and primary Sjögren's syndrome, in which tissues as diverse as the skin, kidneys, and brain may all be affected.

Tissue injury in autoimmune disease results because the self antigen is an intrinsic component of the body and, consequently, the effector mechanisms of the immune system are directed at the body's own tissues. Also, because the adaptive destruction of the cells, leading to anemia. This can occur in two ways. Red cells with bound IgG or IgM antibody are rapidly cleared from the circulation by interaction with Fcγ or complement receptors, respectively, on cells of the fixed mononuclear phagocytic system; this occurs particularly in the spleen. Alternatively, the autoantibody-sensitized red cells are lysed by formation of the membrane-attack complex of complement. In autoimmune thrombocytopenic purpura, autoantibodies primarily against the GpIIb:IIIa fibrinogen receptor on platelets can cause thrombocytopenia (a depletion of platelets), which can in turn cause hemorrhage.

Current treatments for immunological disorders are nearly all empirical in origin, using immunosuppressive drugs identified by screening large numbers of natural and synthetic compounds. The drugs currently used to suppress the immune system can be divided into three categories: first, powerful anti-inflammatory drugs of the corticosteroid family such as prednisone; second, cytotoxic drugs such as azathioprine and cyclophosphamide; and third, fungal and bacterial derivatives, such as cyclosporin A, FK506 (tacrolimus), and rapamycin (sirolimus), which inhibit signaling events within T lymphocytes. These drugs are all very broad in their actions and inhibit protective functions of the immune system as well as harmful ones. Opportunistic infection is therefore a common complication of immuno-suppressive drug therapy. There thus still remains a need for developing safer, more effective therapeutic agents for autoimmune disorders.

Fcγ receptors have been implicated in the pathogenesis of autoimmune disorders. In particular, mice deficient in activating Fcγ receptors were unable to mount inflammatory responses when immunoglobulins (IgG) were bound to their cognate antigens (Sylvestere et al., 1994, Science, 265: 1095-8; Hazenbos et al., 1996, Immunity, 5: 181-8; Clynes et al., 1995, Immunity, 3: 21-26). In marked contrast, animals deficient in complement components had a normal inflammatory response to these experimentally induced cytotoxic antibodies and IgG-antigen complexes (Sylvestre et al., 1996, J. Exp. Med, 184: 2385-2392). This finding demonstrated that FcγRs provided the molecular coupling that allowed bound antibodies to elicit an effector cell response. This observation has led to a fundamental revision of the mechanism by which antibodies trigger inflammation as pathogenic agents in autoimmune diseases.

Idiopathic thrombocytopenic purpura (ITP), a disease in which the patient's immune system attacks and destroys platelets has been a key target for understanding the molecular basis of autoimmune disorders given the availability of experimental animal models (Bussel, 2000, Semin. Oncol. 27: 91-98). Antibodies to platelet glycoproteins have been implicated in the pathogenesis of ITP in humans (McMillan et al., 1981, N. Engl. J. Med., 304: 1135-1147). The development of a mouse model for this disease combined with the use of FcγR knockouts and transgenic mice has allowed greater insight into the mechanisms of pathogenesis and treatment. (NZW×BXSB) F1 mice spontaneously develop thrombocytopenia due to the production of autoantibodies (Oyaizu et al., 1988, J. Exp. Med., 167: 2017-22; Mizutani et al., 1993, Blood, 82: 837-844). An anti-platelet monoclonal antibody, 6A6, was derived from these mice and has been used in other mouse strains as a passive model for ITP. Clynes and Ravetch showed that in FcγR −/− mice, which are deficient in FcγRI and FcγRIIIA function, the monoclonal antibody 6A6 failed to induce thrombocytopenia (Clynes et al., 1995, Immunity, 3:21-26). Further studies demonstrated that the 6A6 antibody failed to induce platelet depletion in animals deleted for FcγRIII, but not in animals deleted for FcγRI. They further demonstrated that IVIG therapy was able to protect wild type animals, but not animals deleted for FcγRIIB, from platelet depletion. Wild type animals treated with IVIG showed increased expression of FcγRIIB (Samuelsson et al., 2001, Science, 291: 484-486). Thus these studies showed that IVIG acts not necessarily by the obvious mechanism of blocking the activating receptor but rather by inducing the inhibitory receptor, FcγRIIB.

Approximately 100,000 people in the United States have ITP including 18,000 with primary ITP, 50,000 with ITP secondary to HIV infection, and 30,000 with ITP secondary to other conditions. Among adults, about three times more women are affected than men, while in children the ratio is about even. The disease affects all age groups. There are approximately 20,000 new cases per year and estimates of incidence range broadly from about 10 to 125 per million people. Current therapeutic strategies to control ITP include administration of intravenous immunoglobulin (IVIG) or Anti-D (anti-rhesus globulin; which can also be delivered via rather than via IV infusion), immunosuppressive agents (such as steroids, azathioprine, or cyclosporine) or splenectomy. However, to date the therapeutic regimens for ITP are deficient and safer more efficacious treatment methods are needed.

3. SUMMARY OF THE INVENTION

Activating FcγR receptors, e.g., FcγIIIA receptor (CD16A), play a critical role in mediating the pathogenic effects of autoantibodies. Although not intending to be bound by a particular theory, the pathogenic IgG's observed in autoimmune diseases are either the pathogenic triggers for these diseases or contribute to disease progression and mediate disease through the inappropriate activation of cellular Fcγ receptors. Aggregated autoantibodies and/or autoantibodies complexed with self antigens (i.e., immune complexes; as used herein, immune complex, refers to a structure which forms when at least one target molecule and at least one heterologous Fc region-containing polypeptide bind to one another forming a larger molecular weight complex. Examples of immune complexes are antigen-antibody complexes which can be either soluble or particulate (e.g., an antigen/antibody complex on a cell surface.)) bind to activating FcγRs, e.g., FcγRIIIA receptor, thereby triggering the pathogenic effects of numerous autoimmune diseases. Although not intending to be bound by any mechanism of action, reducing the activation (i.e., signaling) of an activating FcγR receptor, e.g., FcγRIIIA receptor, by immunoglobulin aggregates (i.e., immune complexes) would be a promising therapeutic approach for treating and/or preventing autoimmune diseases. There, thus, remains a need for either enhancing the therapeutic efficacy of current methods for treating and/or preventing autoimmune diseases, or developing alternative therapeutic regimens, by targeting the FcγR-mediated pathway.

The present invention provides alternative methods and compositions for the treatment and/or prevention of autoimmune diseases. Specifically, the present invention provides molecules and compositions for preventing immune complexes from interacting with activating FcγRs, e.g., FcγRIIIA, with therapeutic efficacy for the treatment and/or prevention of autoimmune diseases. Thus, the invention encompasses treatment regimens or protocols that provide better therapeutic profiles than current single agent therapies or current combination therapy regimens for an autoimmune disease. Preferably, the molecules and compositions of the invention either alone or in combination with additional therapeutic agents also reduce or avoid unwanted or adverse effects. In certain embodiments, the invention includes combination therapies that provide an improved overall therapy relative to current therapies known in the art for an autoimmune disease.

The methods and compositions of the invention are useful not only in untreated subjects, but are also useful in the treatment of patients partially or completely refractory to current standard and experimental therapies for an autoimmune disease. In a preferred embodiment, the invention provides therapeutic and prophylactic methods for the treatment or prevention of an autoimmune disease that has been shown to be or may be refractory or non-responsive to therapies other than those comprising administration of the molecules of the invention. The invention further encompasses administering a molecule of the invention in combination with one or more other therapeutic and/or prophylactic agents known in the art for the treatment and/or prevention of an autoimmune disease.

The present invention relates to molecules, preferably soluble (i.e., not membrane bound) polypeptides, most preferably soluble fusion polypeptides, comprising the extracellular soluble regions of FcγR, and nucleic acids encoding same. The invention encompasses analogs, derivatives, and conjugates of these molecules, and nucleic acids encoding same. The invention particularly relates to soluble FcγRIIIA, and soluble FcγRIIB polypeptides, fusion proteins comprising the extracellular regions of FcγRIIIA, and FcγRIIB and nucleic acids encoding same. The invention also relates to soluble FcγRIIIB, and soluble FcγRIIA polypeptides, fusion proteins comprising the extracellular regions of FcγRIIIB, and FcγRIIA and nucleic acids encoding same.

The invention encompasses fusion proteins that may be monomeric but are preferably dimeric, comprising an extracellular region of an FcγR covalently linked to a heterologous polypeptide. The dimeric fusion proteins of the invention may have one or more specifities. In some embodiments, the fusion proteins of the invention have at least two different binding sites, for example, the fusion protein comprises the extracellular region of the FcγR which specifically binds an FcγR and a molecule that binds an FcRn such as, for example, Fc region of an IgG molecule. By way of example, in one embodiment, the heterologous polypeptide extends the in vivo plasma half life of the extracellular region of FcγR. In preferred embodiments, the extracellular region of FcγR is joined to an immunoglobulin constant region, more preferably a hinge-constant region or a portion thereof. In a most preferred embodiment, the hinge-constant region has a lower affinity for other soluble receptor fusion proteins than it does for a circulating antibody in the patient to which the soluble receptors are administered. In another preferred embodiment, the hinge-constant region of the soluble receptor fusion protein has a lower affinity for membrane bound native FcγRs than it does for a circulating antibody in a patient to which the soluble receptors are administered. Preferably, the Fc region of the fusion proteins of the invention do not bind or have a reduced affinity for the soluble FcγR to which the Fc region is fused. In other embodiments, the Fc region of the fusion proteins of the invention do not bind one or a combination of FcγRs such as FcγRIIA, FcγRIIIA, FcγRIIB. The invention encompasses variants of the hinge-constant region that have been engineered to contain at least one amino acid modification to modulate their affinity for the soluble FcγR, using standard methods known to those in the art, or using any of the methods disclosed in U.S. Provisional Application Nos. 60/439,498; 60/456,041, filed on Jan. 9, 2003, and Mar. 19, 2003, respectively and U.S. Provisional Application No. 60/514,549 filed on Oct. 23, 2003, U.S. application Ser. No. 10/754,922 filed on Jan. 9, 2004, which are incorporate herein by reference in entirely. In a most preferred embodiment, the extracellular region of the FcγR is joined to the IgG2 hinge-constant region.

In certain embodiments, the dimeric fusion proteins of the invention are at least bivalent in that they comprise two soluble extracellular regions of an FcγR wherein each soluble extracellular region contains a binding site for an Fc constant region. Preferably, the soluble extracelullar regions are from the same FcγR, and, more preferably, have the same amino acid sequence. In other embodiments, the soluble extracellular regions are from different FcγRs, i.e., have different specificities, such that the dimeric fusion protein is at least bi-specific. The dimeric fusion proteins of the invention may further comprise a molecule fused to each soluble extracellular region of the FcγRs, wherein the molecule increases the stability (e.g., the serum half-life) of the dimeric fusion proteins. These molecules are preferably the Fc domain of an immunoglobulin, preferably, of an IgG, most preferably, the hinge-constant region of the immunoglobulin Fc. Such molecules may contain one or more additional binding domains, for example, a binding domain for FcRn, and, preferably, do not bind an FcγR. Thus, such molecules of the invention may be at least trivalent, in that they comprise at least three binding sites. In other specific embodiments, the invention includes monomeric fusion proteins having a soluble extracellular region of an FcγR that contains a binding site for an Fc constant region fused to a molecule that increases the stability of the soluble extracellular region. Such monomeric fusion proteins may be monovalent (i.e., have only one binding site) but may also comprise additional binding sites, for example, when the soluble extracellular region is fused to an Fc constant or hinge-constant domain, that domain may also have a binding site for, e.g., FcRn and, as such, are at least bivalent.

In some embodiments, the invention encompasses dimeric fusion proteins comprising an extracellular region of an FcγR covalently linked to any molecule that binds a FcRn (Fc receptor neonate) wherein said dimeric fusion protein preferably does not bind an FcγR. Molecules that bind an FcRn include for example IgG molecules or portions thereof that contain an Fc region or a portion thereof (including hinge-constant region), e.g., IgG1 subclass of IgGs, but may also be any other IgG subclasses of given animals. For example, in humans, the IgG class includes IgG1, IgG2, IgG3, and IgG4; and mouse IgG includes IgG1, IgG2a, IgG2b, IgG2c and IgG3. IgG molecules may comprise at least one or more amino acid modifications that alter their binding affinities for FcγRs and or FcRns. Amino acid modifications that alter binding affinities of IgGs are known in the art and encompassed herein.

In a specific embodiment, the invention encompasses a dimeric fusion protein comprising two identical polypeptide chains, each said chain comprising an extracellular region of FcγRIIIA comprising an Fcγ binding site, joined to a hinge-constant region of IgG2, wherein the dimeric fusion protein specifically binds an immune complex. In yet another specific embodiment, the invention encompasses a dimeric fusion protein comprising two identical polypeptide chains, each said chain comprising an extracellular region of FcγRIIB comprising an Fcγ binding site, joined to a hinge-constant region of IgG2, wherein the dimeric fusion protein specifically binds an immune complex.

The invention relates to therapeutic uses of such molecules, particularly for the treatment and/or prevention of autoimmune diseases. Although not intending to be bound by any mechanism of action, the soluble FcγRIIIA polypeptides, fusion proteins comprising same, and derivatives thereof block the interaction between FcγRIIIA and an immune complex and thus have therapeutic utility as single agent therapeutics. The invention encompasses the use of the soluble FcγRIIIA and/or FcγRIIA polypeptides, fusion proteins comprising same, and derivatives thereof as single agent therapeutics for the treatment/and or prevention of autoimmune diseases. The invention also provides the use of soluble FcγRIIB polypeptides, fusion proteins comprising same, and derivatives thereof for the treatment and/or prevention of autoimmune diseases. This is based, in part, on the surprising discovery by the inventors, as disclosed herein, that fusion proteins comprising FcγRIIB extracellular regions have therapeutic utility in an animal model for an autoimmune disease, even though FcγRIIB is classically not implicated in clearance of immune complexes.

The invention provides soluble FcγR polypeptides which consist of the extracellular region of a FcγR, e.g., FcγRIIIA, FcγRIIA, FcγRIIB. The invention encompasses a method for treating, preventing, or ameliorating one or more symptoms of an autoimmune disorder (examples of autoimmune disorders is disclosed herein in Section 5.4.1), comprising administering a therapeutically effective amount of a soluble FcγR polypeptide in combination with a therapeutically effective amount of one or more therapeutic agents used for the treatment of an autoimmune disease known to those skilled in the art. Therapeutic agents that can be used in combination with the molecules of the invention are disclosed herein in Section 5.4.3. In one specific embodiment, the invention encompasses a method for treating, preventing, or ameliorating one or more symptoms of an autoimmune disorder, comprising administering a therapeutically effective amount of a soluble FcγR polypeptide in combination with a 3G8 monoclonal antibody.

The invention encompasses a method for treating, preventing, or ameliorating one or more symptoms of an autoimmune disorder, comprising administering a therapeutically effective amount of a fusion protein comprising the extracellular region of an FcγR, e.g., FcγRIIIA, FcγRIIIB, joined to an IgG2 hinge constant region (or other polypeptides that enhance stability but do not bind the particular FcγR, e.g., FcγRIIIA, FcγRIIB). In an alternative embodiment, the invention encompasses a combination therapy comprising administering a therapeutically effective amount of a fusion protein comprising the extracellular region of an FcγR, e.g., FcγRIIIA, FcγRIIB, joined to an IgG2 hinge constant region, in combination with one or more additional therapeutic agents known to those skilled in the art for the treatment and/or prevention of an autoimmune disease. The fusion proteins of the invention comprising the extracellular region of an FcγR, e.g., FcγRIIIA, FcγRIIB, joined to an IgG2 hinge constant region are particularly useful for the treatment, prevention, or amelioration of one or more symptoms of idiopathic thrombocytopenic purpura. In one embodiment, the invention encompasses treating, preventing, or ameliorating one or more symptoms of idiopathic thrombocytopenic purpura (ITP) by administering a fusion protein comprising the extracellular region of an FcγR, e.g., FcγRIIIA, FcγRIIB, joined to an IgG2 hinge constant region in combination with a standard idiopathic thrombocytopenic purpura therapy, e.g., IVIG. In a preferred embodiment, administering a fusion protein comprising the extracellular region of an FcγR, e.g., FcγRIIIA, FcγRIIB, joined to an IgG2 hinge constant region for the treatment of ITP has reduced adverse side effects compared to the adverse side effects of a standard ITP therapy, e.g., neutropenia, cytokine release syndrome. In a most preferred embodiment, the fusion protein of the invention comprising the extracellular region of an FcγR, e.g., FcγRIIIA, FcγRIIB, joined to an IgG2 hinge constant region has an enhanced clinical efficacy for an autoimmune disease while incurring minimal side effects.

The invention encompasses engineering the molecules of the invention using standard recombinant DNA technology known to those skilled in the art. In a specific embodiment, the invention encompasses engineering the fusion proteins of the invention comprising an extracellular region of FcγR, e.g., FcγRIIIA, FcγRIIB, such that the fusion proteins comprise at least one amino acid modification in the extracellular region that lowers the affinity of the soluble extracellular protein for an agent greater than 100-fold, preferably 1000-fold (e.g., in the micromolar range) e.g., an antibody which specifically binds the extracellular region of an FcγR for the treatment and/or prevention of an autoimmune disease, so that the resulting modified fusion protein can be administered in combination with that agent, without significant complexing to the agent. The modified fusion protein comprising at least one amino acid modification in the extracellular region also specifically binds an immune complex. In one embodiment, the modified fusion protein comprising at least one amino acid modification in the extracellular region specifically binds an immune complex with a higher affinity relative to a wild-type extracellular region.

In yet another embodiment, the invention encompasses engineering the fusion proteins of the invention comprising an extracellular region of an FcγR, such that the fusion proteins comprise at least one amino acid modification in the extracellular region that abolishes the affinity of the soluble extracellular protein for an agent, and the fusion protein further has an has an enhanced affinity for an immune complex relative to a wild-type extracellular region.

In one specific embodiment, the invention encompasses a dimeric fusion protein comprising two identical polypeptide chains, each chain comprising a variant extracellular region of FcγRIIIA joined to a hinge-constant region of IgG2, wherein said variant extracellular region comprises at least one amino acid modification relative to a wild-type extracellular region of FcγRIIIA, such that a 3G8 monoclonal antibody (or any other antibody that competes with binding of 3G8 antibody to wild-type FcγRIIIA) binds said dimeric fusion protein with a lower affinity than said monoclonal 3G8 antibody binds said wild-type extracellular region, and wherein the dimeric fusion protein specifically binds an immune complex. In one embodiment, the one or more amino acid modifications in the extracellular region of FcγRIIIA comprise a substitution in the 3G8 binding site. In another embodiment, the amino acid modification in the extracellular region of FcγRIIIA comprises a substitution at position 112 with aspartic acid, at position 113 with lysine, and at position 114 with proline. In yet another embodiment, the amino acid modification in the extracellular region of FcγRIIIA comprises a substitution at position 160 with phenylalanine. In another embodiment, the amino acid modification in the extracellular region of FcγRIIIA comprises a substitution at position 154 with asparagine and at position 155 with isoleucine.

The invention also encompasses a dimeric fusion protein comprising two identical polypeptide chains, each chain comprising a wild-type extracellular region of FcγR (e.g., FcγRIIIA, FcγRIIA, FcγRIIB) joined to a hinge-constant region of IgG2.

The invention encompasses treatment and/or prevention of an autoimmune disease using the engineered molecules of the invention. In one embodiment, the invention encompasses a combination regimen for treating, preventing or ameliorating one or more symptoms of an autoimmune disorder, said regimen comprising administering to a subject in need thereof, a therapeutically effective amount of a molecule which specifically binds a wild-type extracellular region of FcγRIIIA comprising an Fc binding site, preferably an antibody, e.g., CLB-GRAN1, BW2-9/2, GRM1, DJ130c, LNK16. (See Tamm et al., 1996, Journal of Immunology, 157(4): 1566-81; Fleit et al., 1989, Leukocyte Typing IV: White Cell Differentiation Antigens, p. 159); and a therapeutically effective amount of a dimeric fusion protein comprising two identical polypeptide chains, each said chain comprising a variant extracellular region of FcγRIIIA, wherein said variant extracellular region comprises at least one amino acid modification relative to said wild-type extracellular region, such that said molecule binds said dimeric fusion protein with a lower affinity than said molecule binds said wild-type extracellular region, and wherein said dimeric fusion protein specifically binds an immune complex.

In one specific embodiment, the invention encompasses a method for treating, preventing or ameliorating one or more symptoms of an autoimmune disorder, said method comprising a combination treatment by administering to a subject in need thereof a therapeutically effective amount of CD16A antagonists such as a dimeric fusion protein of the invention, comprising two identical polypeptide chains, each said chain comprising a variant extracellular region of FcγRIIIA joined to a hinge-constant region of IgG2, wherein said variant extracellular region comprises at least one amino acid modification relative to a wild-type extracellular region of FcγRIIA, such that a 3G8 monoclonal antibody binds said dimeric fusion protein with a lower affinity than said monoclonal 3G8 antibody binds said wild-type extracellular region, and wherein the dimeric fusion protein specifically binds an immune complex.

In another specific embodiment, the invention encompasses a method for treating, preventing or ameliorating one or more symptoms of an autoimmune disorder, said method comprising administering to a subject in need thereof, a therapeutically effective amount of an antibody which specifically binds a wild-type extracellular region of FcγRIIB comprising an Fcγ binding site, e.g., an antibody produced from clone 2B6 having ATCC accession number PTA-4591 (deposited at ATCC, 10801 University Boulevard, Manassas, Va. 02209-2011, which are incorporated herein by reference), and a therapeutically effective amount of a dimeric fusion protein comprising two identical polypeptide chains, each said chain comprising a variant extracellular region of FcγRIIB, wherein said variant extracellular region comprises at least one amino acid modification relative to said wild-type extracellular region, such that said antibody binds said dimeric fusion protein with a lower affinity than said antibody binds said wild-type extracellular region, and wherein said dimeric fusion protein specifically binds an immune complex.

In yet another specific embodiment, the invention encompasses a method for treating, preventing or ameliorating one or more symptoms of an autoimmune disorder, said method comprising administering to a subject in need thereof, a therapeutically effective amount of any of the antibodies disclosed in U.S. Provisional Application No. 60/403,266, filed Aug. 14, 2002, and U.S. application Ser. No. 10/643,857, filed Aug. 14, 2003 which are incorporated herein by reference in their entireties, which specifically binds a wild-type extracellular region of FcγRIIB comprising an Fcγ binding site; and a therapeutically effective amount of a dimeric fusion protein comprising two identical polypeptide chains, each said chain comprising a variant extracellular region of FcγRIIB, wherein said variant extracellular region comprises at least one amino acid modification relative to said wild-type extracellular region, such that said antibody binds said dimeric fusion protein with a lower affinity than said antibody binds said wild-type extracellular region, and wherein said dimeric fusion protein specifically binds an immune complex.

Preferably, the hinge-constant region of an immunoglobulin constant region is defined as the amino acids corresponding to the boundaries of the hinge region of an immunoglobulin constant region, the CH2 domain, and the CH3 domain. In a specific embodiment, the hinge constant region of IgG2 comprises of amino acids 680 to 1366 based on the EU Index as in Kabat et al., Sequences of Proteins of Immunological Interest, 5$^{th}$ Ed. Public Health Science, NIH, Bethesda, Md. (1991), incorporated herein by reference. The "EU index" as in Kabat refers to residue numbering of the human IgG1 EU antibody. In a specific embodiment, a fusion protein of the invention comprises fusing the N-terminal amino acid of the hinge-constant region to the C-terminal amino acid of the extracellular region of an FcγR. The invention encompasses fusing the hinge-constant region to the N-terminal or C-terminal amino acids of an FcγR extracellular region. The invention encompasses portions of the hinge-constant region. As used herein the term "portion of a hinge-constant" refers to a fragment of the hinge-constant region. The fragments may range in size from 5 amino acids to the entire hing-constant region minus one. Preferably, such portions increase the stability of the soluble FcγR.

The invention also encompasses a biologically active fragment of a molecule of the invention. In one embodiment, the invention relates to a fragment of the extracellular region of an FcγR that maintains Fcγ binding as determined by standard assays known to those skilled in the art. In another embodiment, the invention encompasses a biologically active fragment of a dimeric fusion protein of the invention which retains the activity of the native dimeric fusion protein, as described herein. The invention also encompasses polypeptides sufficiently identical (e.g., at least about 45%, preferably 55%, 65%, 75%, 85%, 95%, 99%) to or derived from the amino acid sequences of the molecules of the invention.

The invention also encompass polynucleotides that encode the molecules of the invention, e.g., an isolated nucleic acid molecule encoding a dimeric fusion protein of the invention comprising an extracellular region of an Fcγ R fused to an immunoglobulin constant region. The invention provides nucleic acid molecules that encode a molecule of the invention or a biologically active fragment thereof. In certain embodiments, the invention provides nucleic acid molecules encoding a variant of a molecule of the invention that maintains biological activity compared to the native molecule, as determined by standard assays known to those skilled in the art or described herein. Nucleic acid molecules corresponding to any immunoglobulin constant region is within the scope of the invention, including but not limited to, IgM, IgG, IgG1, IgG2, IgD, IgE, IgA. The invention also encompasses nucleic acid molecules encoding a variant of an immunoglobulin constant region. In a preferred embodiment, the invention encompasses nucleic acid molecules encoding a variant of an immunoglobulin constant region that has a lower affinity for an FcγRIIIA as determined by standard assays known to those skilled in the art. In another preferred embodiment, the constant region is one of the variants disclosed in U.S. Provisional Application Nos. 60/439,498; 60/456,041, filed on Jan. 9, 2003, Mar. 19, 2003 and U.S. Provisional Application No. 60/514,549 filed on Oct. 23, 2003, and U.S. application Ser. No. 10/754,922 filed on Jan. 9, 2004; all of which are incorporated herein by reference in their entirety, as well particular variants identified by the methods disclosed therein.

In one embodiment, the invention provides an isolated nucleic acid sequence encoding the extracellular region of FcγRIIIA, preferably human. In one embodiment, the invention encompasses cDNA encoded by cDNA with GENBANK Accession No X52645 (cDNA=GI:31323). In an alternative embodiment, the invention provides a protein encoded by the GENBANK Accession Number P08637 (Protein=GI: 119876). In preferred embodiments, the invention encompasses allelic variants referenced herein, especially 158V/F. In one embodiment, the invention provides an isolated nucleic acid sequence encoding the extracellular region of FcγRIIIB, preferably human. In another embodiment, the invention provides an isolated nucleic acid sequence encoding the extracellular region of FcγRIIB, preferably human. The fusion proteins of the invention encompasses protein and DNA encoded by the following sequences of deposits, or portions thereof: Genbank Accession No.'s M31934 (GI: 182600, FcγRIIB-2 cDNA); AAA35842 (FcγRIIB-2 Protein=GI:182601); M31935, (FcγRIIB-1 cDNA=GI: 182602); M31933 (FcγRIIB-3 cDNA=GI:182598), all of which are incorporated herein by reference. The invention also encompasses an isolated nucleic acid sequence encoding the extracellular region of FcγRIIA, preferably human. The invention encompasses Genbank Accession No M31932 (GI: 182473; FcγRIIA cDNA). In one embodiment, the invention provides an isolated nucleic acid sequence encoding the extracellular region of FcγRIIIA, preferably human, fused to the hinge-constant region of IgG2. In one embodiment, the invention provides an isolated nucleic acid sequence encoding the extracellular region of FcγRIIIB, preferably human, fused to the hinge-constant region of IgG2. In another embodiment the invention provides an isolated nucleic acid sequence encoding the extracellular region of FcγRIIB, preferably human, fused to the hinge-constant region of IgG2. In yet another embodiment the invention provides an isolated nucleic acid sequence encoding the extracellular region of FcγRIIA, preferably human, fused to the hinge-constant region of IgG2.

The invention also relates to a vector comprising said nucleic acids. In one specific embodiment, said vector is an expression vector. In a preferred embodiment, a vector expressing a soluble fusion protein comprising the extracellular region of FcγRIIB, FcγRIIA, FcγRIIIA or FcγRIIIB, preferably human, fused to the hinge-constant region of IgG2, is stably transfected into HEK-293 cells, by standard transfection methods known to those skilled in the art, and the soluble fusion protein is secreted. The secreted fusion protein is preferably purified by a protein G chromatography procedure, followed by affinity chromatography on an IgG column. In a most preferred embodiment, the fusion protein is purified to 95% homogeneity.

The invention further provides host cells containing the vectors of or polynucleotides encoding the molecules of the invention. The invention further provides methods for the production of molecules of the invention. The molecules of the invention can be produced by any method known in the art for the production of polypeptides, in particular, fusion polypeptides, e.g., chemical synthesis or by recombinant expression techniques known in the art.

The invention encompasses methods for characterizing the molecules of the invention in cell-based and cell-free assays. The invention encompasses methods for determining the ability of a molecule of the invention comprising or consisting of an extracellular FcγR region to immunospecifically bind a ligand, e.g., an immune complex. Any standard assay known to those skilled in the art is contemplated in the methods of the invention, including for example, ELISA-based assays, radioimmunobased assays, FACS analysis, etc. (See Section 5.2, infra) In one specific embodiment, molecules of the invention bind an immune complex with a Kd in the range of 1-10 nM as determined in an immunobased assay, e.g., ELISA or Biacore analysis. In another embodiment, molecules of the invention comprising at least one amino acid modification in the extracellular region of FcγRIIIA bind an immune complex with a higher avidity relative to a molecule comprising a wild-type extracellular region. The invention further encompasses characterizing the molecules of the invention by immune complex blocking assays known to those skilled in the art. Additionally the therapeutic efficacy of the molecules of the invention can be determined in animal model. An exemplary model system is a mouse model system for ITP (see, Oyaizu et al., 1988, J. Exp. Med. 167: 2017-22; and Mizutani et al., 1993, Blood, 82: 837-44, both of which are incorporated herein by reference in their entirety). See Example 6, infra.

The invention also encompasses pharmaceutical compositions comprising the molecules of the invention. In one embodiment the invention encompasses a pharmaceutical composition comprising a therapeutically effective amount of a dimeric fusion protein comprising two identical polypeptide chains, each said chain comprising an extracellular region of FcγRIIIA comprising an Fcγ binding site, joined to a hinge-constant region of IgG2, wherein the dimeric fusion protein specifically binds an immune complex; and a pharmaceutically acceptable carrier. In another embodiment, the invention encompasses a pharmaceutical composition comprising a therapeutically effective amount of a dimeric fusion protein comprising two identical polypeptide chains, each said chain comprising an extracellular region of FcγRIIB comprising an Fcγ binding site, joined to a hinge-constant region of IgG2, wherein the dimeric fusion protein specifically binds an immune complex, and a pharmaceutically acceptable carrier.

In yet another embodiment, the invention encompasses a pharmaceutical composition comprising: a therapeutically effective amount of a molecule which specifically binds a wild-type extracellular region of FcγRIIIA; a therapeutically effective amount of a dimeric fusion protein comprising two identical polypeptide chains, each said chain comprising a variant extracellular region of FcγRIIIA, wherein said variant extracellular region comprises at least one amino acid modification relative to said wild-type extracellular region, such that said molecule binds said dimeric fusion protein with a lower affinity than said molecule binds said wild-type extracellular region, and wherein said dimeric fusion protein specifically binds an immune complex; and a pharmaceutically acceptable carrier.

3.1 Definitions

As used herein, the term "specifically binds an immune complex" and analogous terms refer to molecules that specifically bind to an immune complex and do not specifically bind to another molecule. A molecule that specifically binds to an immune complex may bind to other peptides or polypeptides with lower affinity as determined by, e.g., immunoassays, BIAcore, or other assays known in the art. Preferably, molecules that specifically bind an immune complex do not cross-react with other proteins. Molecules that specifically bind an immune complex can be identified, for example, by immunoassays, BIAcore, or other techniques known to those of skill in the art.

As used herein, immune complex, refers to a structure which forms when at least one target molecule and at least one heterologous Fcγ region-containing polypeptide bind to one another forming a larger molecular weight complex. Examples of immune complexes are antigen-antibody complexes which can be either soluble or particulate (e.g., an antigen/antibody complex on a cell surface.)

As used herein, the terms "heavy chain," "light chain," "variable region," "framework region," "constant domain," and the like, have their ordinary meaning in the immunology art and refer to domains in naturally occurring immunoglobulins and the corresponding domains of synthetic (e.g., recombinant) binding proteins (e.g., humanized antibodies, single chain antibodies, etc.). The basic structural unit of naturally occurring immunoglobulins (e.g., IgG) is a tetramer having two light chains and two heavy chains, usually expressed as a glycoprotein of about 150,000 daltons. The amino-terminal ("N") portion of each chain includes a variable region of about 100 to 110 or more amino acids primarily responsible for antigen recognition. The carboxy-terminal ("C") portion of each chain defines a constant region, with light chains having a single constant domain and heavy chains usually having three constant domains and a hinge region. Thus, the structure of the light chains of an IgG molecule is n-$V_L$-$C_L$-c and the structure of IgG heavy chains is n-$V_H$-$C_{H1}$-H—$C_{H2}$-$C_{H3}$-c (where H is the hinge region). The variable regions of an IgG molecule consist of the complementarity determining regions (CDRs), which contain the residues in contact with antigen and non-CDR segments, referred to as framework segments, which in general maintain the structure and determine the positioning of the CDR loops (although certain framework residues may also contact antigen). Thus, the $V_L$ and $V_H$ domains have the structure n-FR1, CDR1, FR2, CDR2, FR3, CDR3, FR4-c.

As used herein the terms "FcγRIIIA binding protein," "FcγRIIIA antibody," and "anti-FcγRIIIA antibody", are used interchangeably and refer to a variety of immunoglobulin-like or immunoglobulin-derived proteins. "FcγRIIIA binding proteins" bind FcγRIIIA via an interaction with $V_L$ and/or $V_H$ domains (as distinct from Fcγ-mediated binding). Examples of FcγRIIIA binding proteins include fully human, polyclonal, chimeric and humanized antibodies (e.g., comprising 2 heavy and 2 light chains), fragments thereof (e.g., Fab, Fab', $F(ab')_2$, and Fv fragments), bifunctional or multifunctional antibodies (see, e.g., Lanzavecchia et al., 1987, *Eur. J Immunol.* 17:105), single chain antibodies (see, e.g., Bird et al., 1988, *Science* 242:423-26), fusion proteins (e.g., phage display fusion proteins), "minibodies" (see, e.g., U.S. Pat. No. 5,837,821) and other antigen binding proteins comprising a $V_L$ and/or $V_H$ domain or fragment thereof. In one aspect, the FcγRIIIA binding protein is a "tetrameric antibody" i.e., having generally the structure of a naturally occurring IgG and comprising variable and constant domains, i.e., two light chains comprising a $V_L$ domain and a light chain constant domain and two heavy chains comprising a $V_H$ domain and a heavy chain hinge and constant domains.

As used herein the term "CD16 antagonists," refers to protein and non-proteinacious substances, including small molecules which antagonize at least one biological activity of FcγRIIIA, e.g., block signaling. For example, the molecules of the invention block signaling by blocking the binding of IgGs to FcγRIIIA.

When referring to binding proteins or antibodies (as broadly defined herein), the assignment of amino acids to each domain is in accordance with the definitions of Kabat, Sequences of Proteins of Immunological Interest (National Institutes of Health, Bethesda, Md., 1987 and 1991). Amino acids from the variable regions of the mature heavy and light chains of immunoglobulins are designated by the position of an amino acid in the chain. Kabat described numerous amino acid sequences for antibodies, identified an amino acid consensus sequence for each subgroup, and assigned a residue number to each amino acid. Kabat's numbering scheme is extendible to antibodies not included in his compendium by aligning the antibody in question with one of the consensus sequences in Kabat by reference to conserved amino acids. This method for assigning residue numbers has become standard in the field and readily identifies amino acids at equivalent positions in different antibodies, including chimeric or humanized variants. For example, an amino acid at position 50 of a human antibody light chain occupies the equivalent position to an amino acid at position 50 of a mouse antibody light chain.

The "Fcγ region" of immunoglobulins refers to the C-terminal region of an immunoglobulin heavy chain. Although the boundaries of the Fcγ region may vary somewhat, usually the Fcγ region is from about position 226-230 extending to the carboxy terminus of the polypeptide (and encompassing the CH2 and CH3 domains). The term "Fcγ region-containing polypeptide" refers to a polypeptide such as an antibody which comprises an Fcγ region.

The Fcγ region of an IgG comprises two constant domains, CH2 and CH3. The CH2 domain of a human IgG Fcγ region (also referred to as "Cg2" domain) usually extends from amino acid 231-340. The CH2 domain is unique in that it is not closely paired with another domain. Rather, two N-linked branched carbohydrate chains are interposed between the two CH2 domains of an intact native IgG.

Throughout the present specification, the numbering of the residues in an IgG heavy chain is that of the EU index as in Kabat et al., Sequences of Proteins of Immunological Interest, $5^{th}$ Ed. Public Health Service, NH1, MD (1991), expressly incorporated herein by references. The "EU index as in Kabat" refers to the numbering of the human IgG1 EU antibody. For the IgG2 hinge region, not all residues are numbered by the Eu index. Throughout the present specification, unless otherwise specified, the numbering of the residues in the FcRs is based on the numbering as disclosed by Sondermann et al., 2000 *Nature*, 406: 267-273, which is incorporated herein by reference in its entirety. In the case of the commonly referenced polymorphic variant of FcγRIIIA at position 158 (see, e.g., Koene et al., 1997, *Blood*, 90:1109-14; Wu et al., 1997, *J. Clin. Invest.* 100, which are incorporated herein by reference) the numbering commonly used is referenced rather than the numbering based on Sondermarn et al. (i.e., position 158 refers to position 155 in Sondermann et al., and position 159 in SEQ ID No. 1:

"Identical polypeptide chains" as used herein also refers to polypeptide chains having almost identical amino acid sequence, for example, including chains having one or more amino acid differences, preferably conservative amino acid substitutions, such that the activity of the two polypeptide chains is not significantly different "Hinge region" is generally defined as stretching from Glu 216 to Pro 230 of human IgG1 (Burton, *Molec. Immunol.*, 22: 161-206, 1985). Hinge regions of other IgG isotypes may be aligned with the IgG1 sequence by placing the first and last cysteine residues forming inter-heavy chain S—S bonds in the same positions.

As used herein, the terms "antibody" and "antibodies" refer to monoclonal antibodies, multispecific antibodies, human antibodies, humanized antibodies, synthetic antibodies, chimeric antibodies, camelized antibodies, polyclonal antibodies, single-chain Fvs (scFv), single chain antibodies, Fab fragments, F(ab') fragments, disulfide-linked Fvs (sdFv), intrabodies, and anti-idiotypic (anti-Id) antibodies (including, e.g., anti-Id and anti-anti-Id antibodies to antibodies of the invention), and epitope-binding fragments of any of the above. In particular, antibodies include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

As used herein, "immune complex", refers to a structure which forms when at least one target molecule and at least one heterologous Fcγ region-containing polypeptide bind to one another forming a larger molecular weight complex. Examples of immune complexes are antigen-antibody complexes which can be either soluble or particulate (e.g., an antigen/antibody complex on a cell surface.)

A "stable fusion protein" as used herein refers to a fusion protein that undergoes minimal to no detectable level of degradation during production and/or storage as assessed using common biochemical and functional assays known to one skilled in the art, and can be stored for an extended period of time with no loss in biological activity, e.g., binding to FcγR.

As used herein, the term "derivative" in the context of polypeptides or proteins refers to a polypeptide or protein that comprises an amino acid sequence which has been altered by the introduction of amino acid residue substitutions, deletions or additions. The term "derivative" as used herein also refers to a polypeptide or protein which has been modified, i.e, by the covalent attachment of any type of molecule to the polypeptide or protein. For example, but not by way of limitation, an antibody may be modified, e.g., by glycosylation, acetylation, pegylation, phosphorylation, amidation, derivatization by known protecting/blocking groups, proteolytic cleavage, linkage to a cellular ligand or other protein, etc. A derivative polypeptide or protein may be produced by chemical modifications using techniques known to those of skill in the art, including, but not limited to specific chemical cleavage, acetylation, formylation, metabolic synthesis of tunicamycin, etc. Further, a derivative polypeptide or protein derivative possesses at least one similar or identical biological function as the polypeptide or protein from which it was derived.

As used herein, the term "derivative" in the context of a non-proteinaceous derivative refers to a second organic or inorganic molecule that is formed based upon the structure of a first organic or inorganic molecule. A derivative of an organic molecule includes, but is not limited to, a molecule modified, e.g., by the addition or deletion of a hydroxyl, methyl, ethyl, carboxyl or amine group. An organic molecule may also be esterified, alkylated and/or phosphorylated.

As used herein, the terms "disorder" and "disease" are used interchangeably to refer to a condition in a subject. In particular, the term "autoimmune disease" is used interchangeably with the term "autoimmune disorder" to refer to a condition in a subject characterized by cellular, tissue and/or organ injury caused by an immunologic reaction of the subject to its own cells, tissues and/or organs. The term "inflammatory disease" is used interchangeably with the term "inflammatory disorder" to refer to a condition in a subject characterized by inflammation, preferably chronic inflammation. Autoimmune disorders may or may not be associated with inflammation. Moreover, inflammation may or may not be caused by an autoimmune disorder. Thus, certain disorders may be characterized as both autoimmune and inflammatory disorders.

As used herein, the term "immunomodulatory agent" and variations thereof including, but not limited to, immunomodulatory agents, refer to an agent that modulates a host's immune system. In certain embodiments, an immunomodulatory agent is an immunosuppressant agent. In certain other embodiments, an immunomodulatory agent is an immunostimulatory agent. Immunomodatory agents include, but are not limited to, small molecules, peptides, polypeptides, fusion proteins, antibodies, inorganic molecules, mimetic agents, and organic molecules.

As used herein, the term "epitope" refers to a fragment of a molecule having antigenic or immunogenic activity in an animal, preferably in a mammal, and most preferably in a human. An epitope having immunogenic activity is a fragment of a polypeptide or protein that elicits an antibody response in an animal. An epitope having antigenic activity is a fragment of a polypeptide or protein to which an antibody immunospecifically binds as determined by any method well-known to one of skill in the art, for example by immunoassays. Antigenic epitopes need not necessarily be immunogenic.

As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of another polypeptide. In a specific embodiment, a fragment of a polypeptide retains at least one function of the polypeptide.

As used herein, the terms "nucleic acids" and "nucleotide sequences" include DNA molecules (e.g., cDNA or genomic DNA), RNA molecules (e.g., mRNA), combinations of DNA and RNA molecules or hybrid DNA/RNA molecules, and analogs of DNA or RNA molecules. Such analogs can be generated using, for example, nucleotide analogs, which include, but are not limited to, inosine or tritylated bases. Such analogs can also comprise DNA or RNA molecules comprising modified backbones that lend beneficial attributes to the molecules such as, for example, nuclease resistance or an increased ability to cross cellular membranes. The nucleic acids or nucleotide sequences can be single-stranded, double-stranded, may contain both single-stranded and double-stranded portions, and may contain triple-stranded portions, but preferably is double-stranded DNA.

As used herein, a "therapeutically effective amount" refers to that amount of the therapeutic agent sufficient to treat or manage a disease or disorder associated with the loss of regulation in the Fcγ receptor signaling pathway, e.g., an autoimmune disease, or to enhance the therapeutic efficacy of another therapy, e.g., IVIG therapy, etc. A therapeutically effective amount may refer to the amount of therapeutic agent sufficient to delay or minimize the onset of disease. A therapeutically effective amount may also refer to the amount of the therapeutic agent that provides a therapeutic benefit in the treatment or management of a disease. Further, a therapeutically effective amount with respect to a therapeutic agent of the invention means that amount of therapeutic agent alone, or in combination with other therapies, that provides a therapeutic benefit in the treatment or management of a disease, e.g., an amount sufficient to enhance the therapeutic efficacy of IVIG therapy sufficient to treat or manage a disease. Used in connection with an amount of a molecule of the invention, the term can encompass an amount that improves overall therapy, reduces or avoids unwanted effects, or enhances the therapeutic efficacy of or synergies with another therapeutic agent.

As used herein, the terms "prophylactic agent" and "prophylactic agents" refer to any agent(s) which can be used in the prevention of a disorder, or prevention of recurrence or spread of a disorder. A prophylactically effective amount may also refer to the amount of the prophylactic agent that provides a prophylactic benefit in the prevention of disease. Further, a prophylactically effective amount with respect to a prophylactic agent of the invention means that amount of prophylactic agent alone, or in combination with other agents, that provides a prophylactic benefit in the prevention of disease. Used in connection with an amount of a molecule the invention, the term can encompass an amount that improves overall prophylaxis or enhances the prophylactic efficacy of or synergies with another prophylactic agent, such as but not limited to a therapeutic antibody.

As used herein, the terms "prevent", "preventing" and "prevention" refer to the prevention of the recurrence or onset of one or more symptoms of a disorder in a subject resulting from the administration of a prophylactic or therapeutic agent.

As used herein, the term "in combination" refers to the use of more than one prophylactic and/or therapeutic agents. The use of the term "in combination" does not restrict the order in which prophylactic and/or therapeutic agents are administered to a subject with a disorder. A first prophylactic or therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a subject with a disorder.

4. BRIEF DESCRIPTION OF THE DRAWINGS

FIGS. 1A-C sFcγRIIIA-G2 Variants with Enhanced Stability

A. The construct sFcγRIIIA-G2 was mutagenized to generate variants V1-V4 which are shown in panel A.

B. The stability of variants V1-4 was compared to that of wild-type by monitoring the protein on SDS-PAGE under reducing conditions at time zero, 1 month and 2 months at 25° C. The wild type molecule showed significant breakdown at 1 month with almost no full length protein left at 2 months. All four variants exhibited a small degree of breakdown after 2 months at 25° C.

C. The variants were tested for their ability to inhibit binding of labeled monomeric FcγRIIIA to immune compleses in an ELISA assay. Each variants showed increased potency relative to wild-type.

Figure 2:
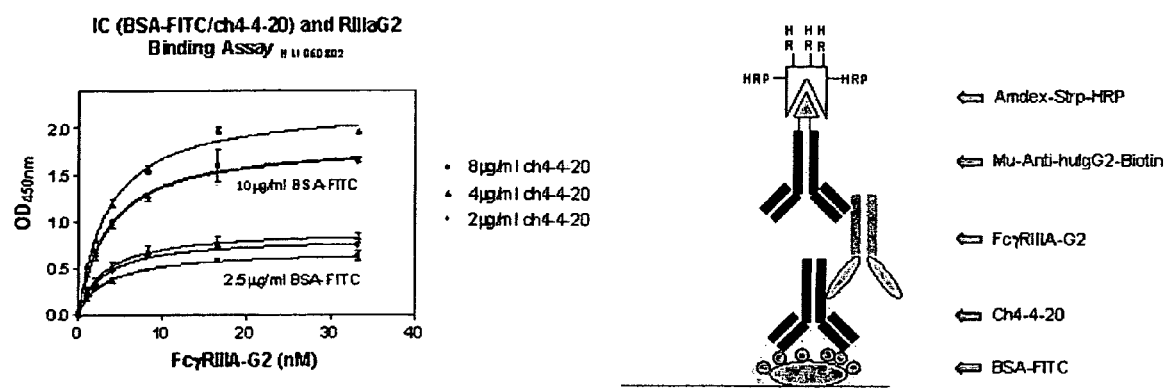

FIG. 2 FcγRIII Binding with BSA-FITC ch4-4-20 Immune Complex

The right panel schematically shows the assay used to measure FcγR binding with an immune complex (BSA-FITC/4-4-20). Briefly, FITC-labeled BSA is coated onto MaxiSorp plates. Immune complex is formed by incubating the coated plate with ch 4-4-20. sFcγRIIIA-G2 or mutants thereof bind to the immune complex human IgG1 Fcγ portion. The bound sFcγRIIIA-G2 or mutants thereof are detected with mouse anti-human IgG2 monoclonal antibody. The left panel shows immune complex binding to FcγRIIIA-G2 at various concentrations of ch-4-4-20, 2 µg/mL, 4 µg/mL, and 8 µg/mL.

Figure 3:
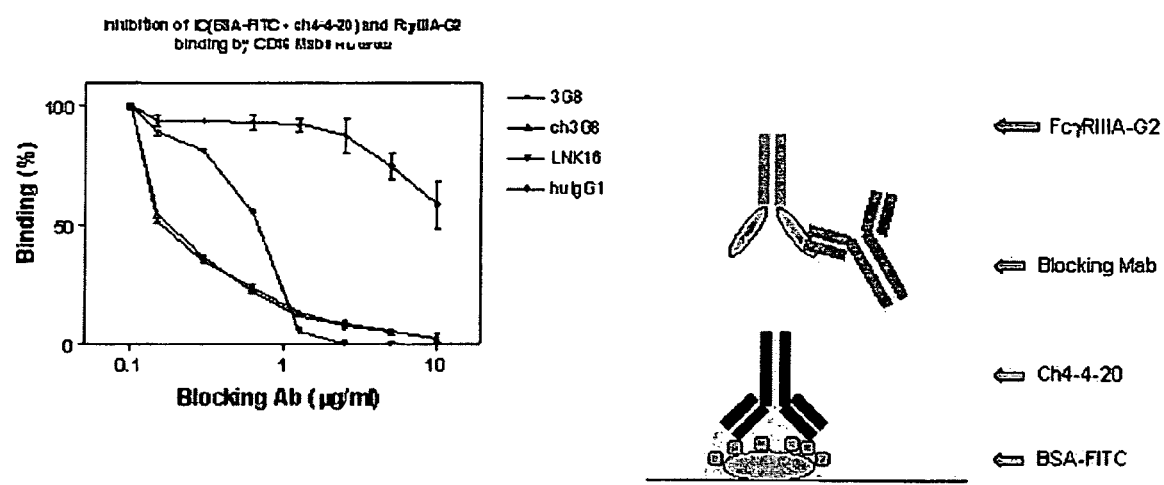

FIG. 3 Assay for Immune Complex/FcγRIIIA Binding Inhibition by 3G8

On the right panel the assay for immune complex/FcγRIIIA binding inhibition by 3G8 is schematically represented. On the left panel inhibition of the immune complex, BSA-FITC/ch-4-4-20 bound to FcγRIIIA-G2 by various antibodies is measured. ■ represents inhibition by 3G8; ▲ represents inhibition by ch3G8; ♦ represents inhibition by human IgG1; and ▼ represents inhibition by LNK 16.

Figure 4:
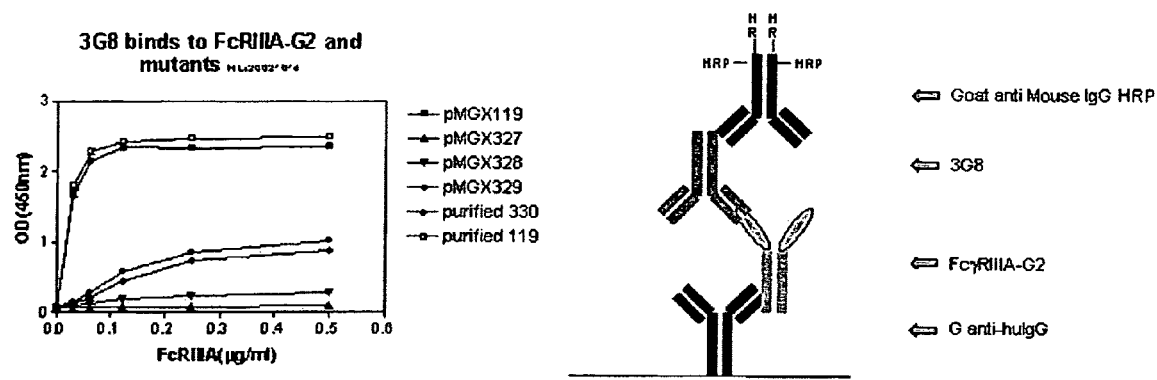

FIG. 4 Assay for Binding of 3G8 and FcγRIIIA Fusion Proteins

On the right panel the assay for measuring the binding of 3G8 and FcγRIIIA fusion proteins is schematically depicted. Briefly, Goat anti human IgG antibody was coated on MaxiSorp plate. sFcγRIIIA-G2 or mutants thereof were captured through their IgG2 Fcγ portion. The captured sFcγRIIIA-G2 or mutants thereof were incubated with the 3G8 monoclonal antibody. The amount of attached 3G8 was detected by goat anti-mouse antibody conjugated with HRP. On the left panel, binding of 3G8 to sFcγRIIIA-G2, and various mutants is compared to the binding of wild-type extracellular region (pMGX119). ¤ and ■ represent the wild-type extracellular region; ▲ is pMGX327 (156GSKNV160→GYTLF); ▼ is pMGX-328 (V160F); ■ is pMGX-329 (154LV155→NI).

FIGS. 5A-C Immune Complex Binding Assays

In FIGS. 5A-5C immune complex binding of sFcγRIIIA-G2 and its mutants are compared to the immune complex binding of wild-type protein.

A. Immune complex binding of pMGX330 ▲ is compared to wild-type ■.

B. Immune complex binding of pMGX327 ▲, pMGX328 ▼, pMGX329 ♦, is compared to wild-type ■.

C. Immune complex binding of pMGX 335.1 ▲, pMGX336.1 ▼, pMGX337.1 ♦, pMGX337.2●, pMGX339.1 ¤, is compared to wild-type ■.

FIGS. 6A-D Inhibition Assays of Immune Complex/FcγRIIIA Binding by 3G8 or Chimeric 3-G8

A. Inhibition assay with ch3G8 with sFcγRIIIA-G2 mutants

B. 3G8 blocking activity of pMGX327 ▲, pMGX328 ▼, pMGX329 ♦ is compared to that of wild-type ■.

C. 3G8 blocking activity of pMGX335.1, ▲ pMGX336.1 ▼, pMGX337.1 ♦ is compared to wild type.

D. 3G8 blocking activity of pMGX338.1 ▲, pMGX339.1 ▼, pMGX340.1 ♦ is compared to wild-type.

FIGS. 7A-C 3G8 Binding Assay

A. 3G8 binding of pMGX327 ▲, pMGX328 ▼, pMGX327 ▲, pMGX329 ♦, purified 330 ●, is compared to pMGX119 ■ and purified 119 (¤wild type).

B. 3G8 binding of pMGX335.1 ▲, pMGX336.1 ▼, pMGX337.1 ♦, pMGX338.1, pMGX339.1 ¤ is compared to pMGX119 ■ (wild-type).

C. 3G8 binding of pMGX340.1 ▲, pMGX335.2 ▼, pMGX336.2 ♦, pMGX338.2, pMGX339.2 ¤ is compared to pMGX119 (wild-type).

Figure 8:
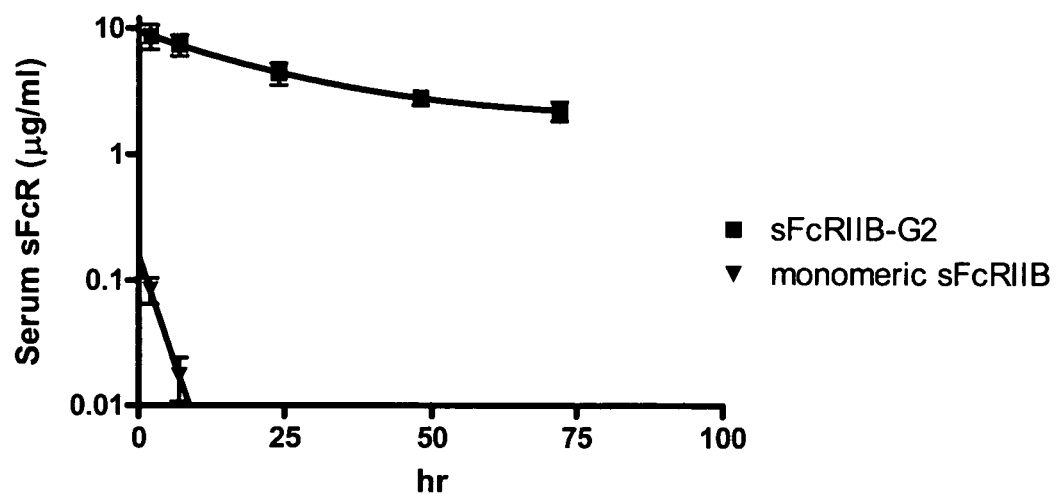

FIG. 8 Pharmacokinetics of sFcγRIIB Molecules in BALB/C Mice sFcγRIIB-G2-N297Q or sFcγRIIB were administered by IV injection into groups of 4 to 5 mice at a dose of 1 mg/Kg. At times 2, 7, 24, 48, and 72 hours later animals were bled and the level of soluble receptor in the resulting serum determined by a sandwich ELISA assay.

Figure 9:
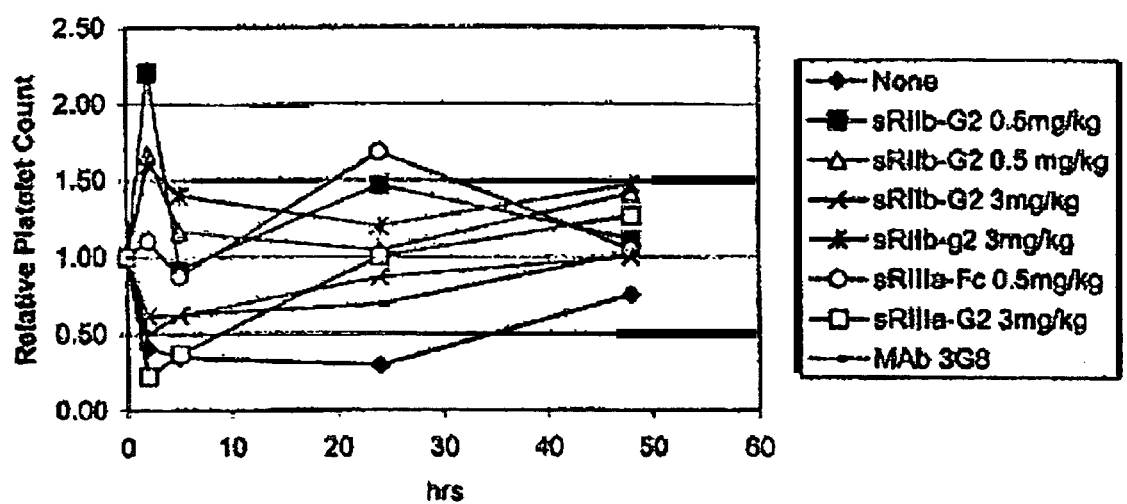

FIG. 9 Platelet Depletion Assay

Plasma platelet counts were determined after administering sFcγRIII-G2 (3 mg/kg) ¤, sFcγRIIIA-Fcγ(0.5 mg.kg)○, sFcγRIIB-G2(0.5 mg/kg) ■, sFcγRIIB-G2 (3 mg/kg)*.

Figure 10:
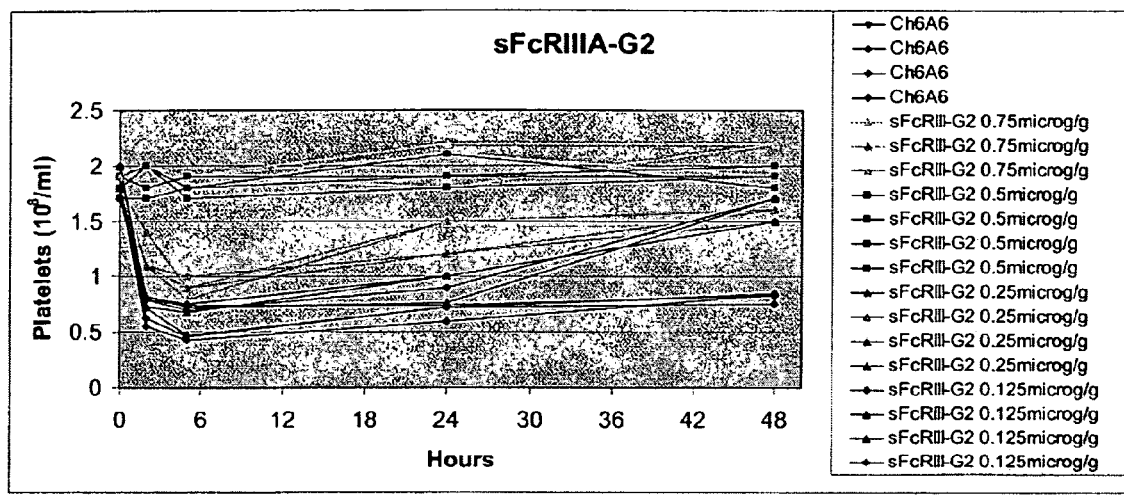

FIG. 10 Dosing Curves

Mice induced to have ITP were treated with sFcγRIIIA-G2 at the concentration ranges indicated.

Figure 11:
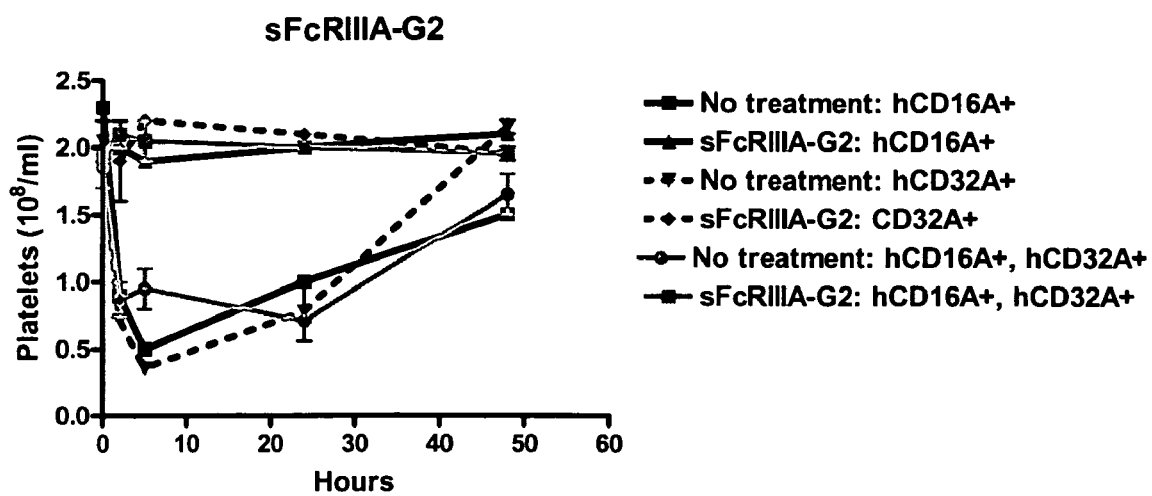

FIG. 11 Use of FcγRIIIA-G2 in ITP Prevention.

mFcγRIIIA−/−, hCD32A+, mFcγRIIIA−/− hCD16A+ and mFcγRIIIA−/− hCD32A+ and mFcγRIIIA−/− hCD16A+ mice induced to have ITP were treated with sFcγRIIIA-G2 at the concentration ranges indicated. Pre-injection with 0.5 µg/g prevents the development of ITP in all mice.

Figure 12:
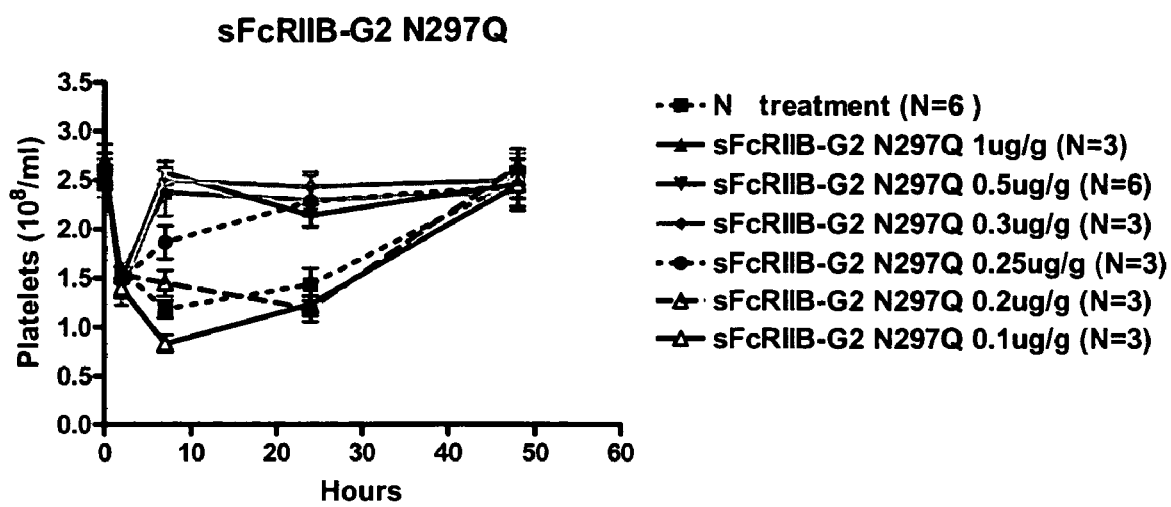

FIG. 12 Use of FcγRIIB-G2-N297Q in Therapy Against ITP

ITP was induced in mFcγRIIIA−/−, hCD16A+ mice by i.p. injection of 0.1 µg/g ch6A6 at time 0. Two hours later, the number of platelets in the plasma was determined to confirm the presence of ITP. Three hours after i.p. injection of ch6A6, mice were injected i.v. with sFcγRIIB-G2-N297Q at different concentrations (arrow).

Figure 13:
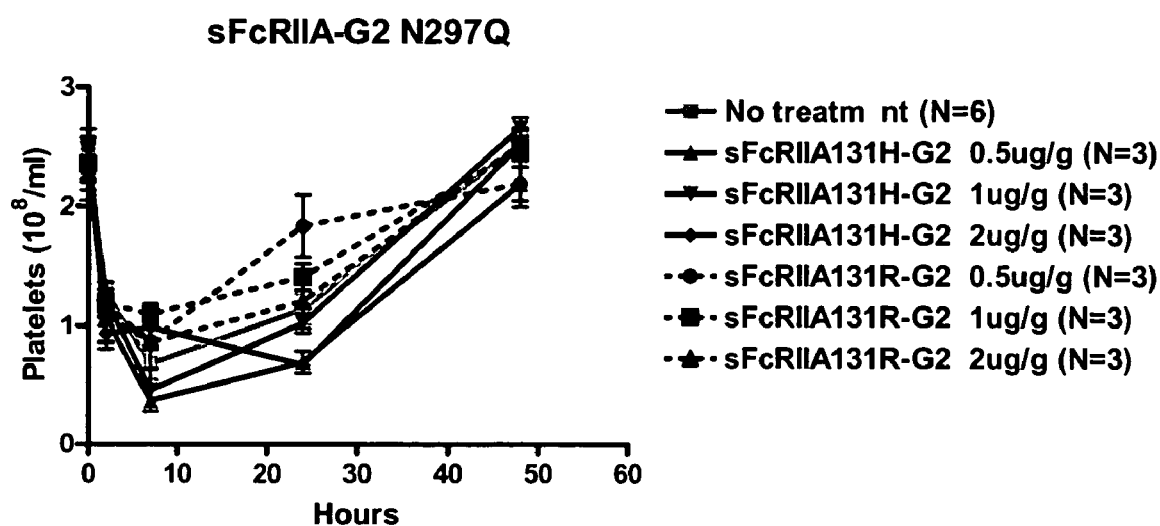

FIG. 13 Use of FcγRIIA-G2-N297Q in Therapy Against ITP

ITP was induced in mFcγRIIIA−/−, hCD16A+ mice by i.p. injection of 0.1 µg/g ch6A6 at time 0. Two hours later, the number of platelets in the plasma was determined to confirm the presence of ITP. Three hours after i.p. injection of ch6A6, mice were injected i.v. with sFcγRIIA131H-G2-N297Q or sFcγRIIA131R-G2-N297Q at different concentrations (arrow).

Figure 14:
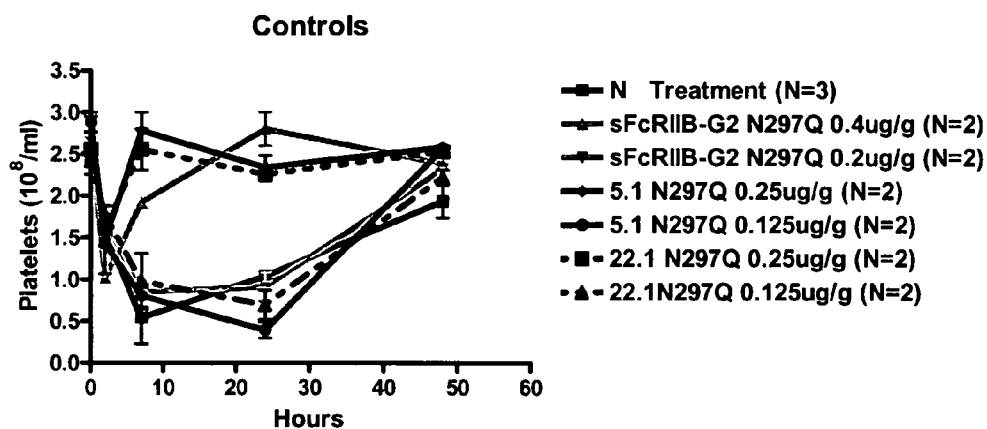
Figure 14:
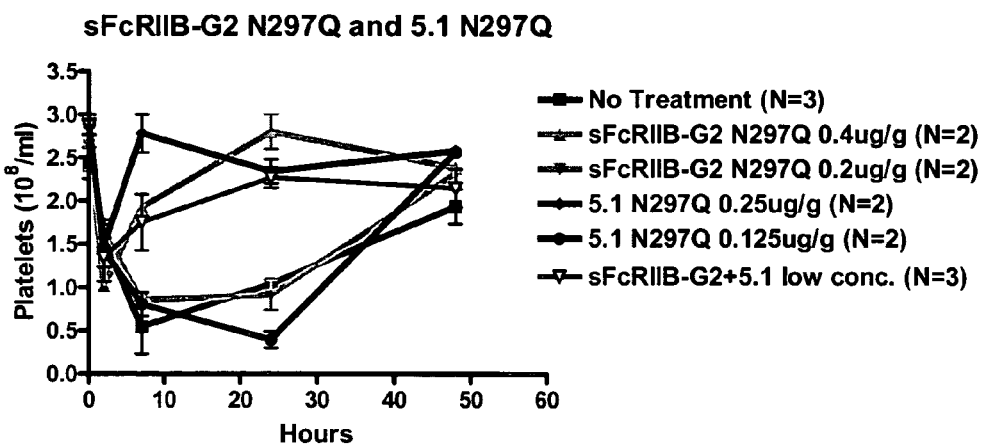
Figure 14:
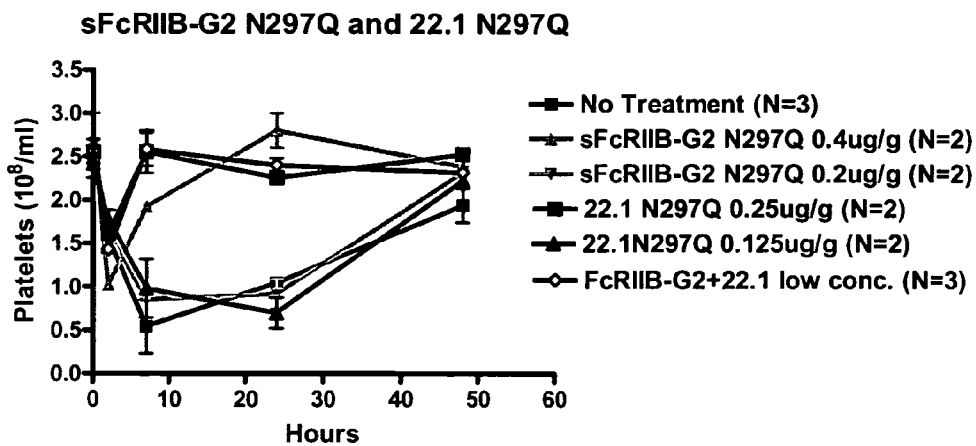

FIGS. 14A-C Use of Combination of sFcγRIIB-G2 N297Q and Anti-hFcγRIIIA Antibodies in Therapy Against ITP.

A. Control treatments with no combination therapy.

B. ITP was induced in mFcγRIIIA−/−, hCD16A+ mice by i.p. injection of 0.1 µg/g ch6A6 at time 0. Two hours later, the number of platelets in the plasma was determined to confirm the presence of ITP. Three hours after i.p. injection of ch6A6, mice were injected i.v. with sFcγRIIB-G2-N297Q or anti-hFcγRIIIA 5.1 N297Q and 22.1 N297Q antibodies at different concentrations (arrow). The "low" concentration does not cure ITP in these experimental conditions whereas the "high" concentration does.

Figure 15:
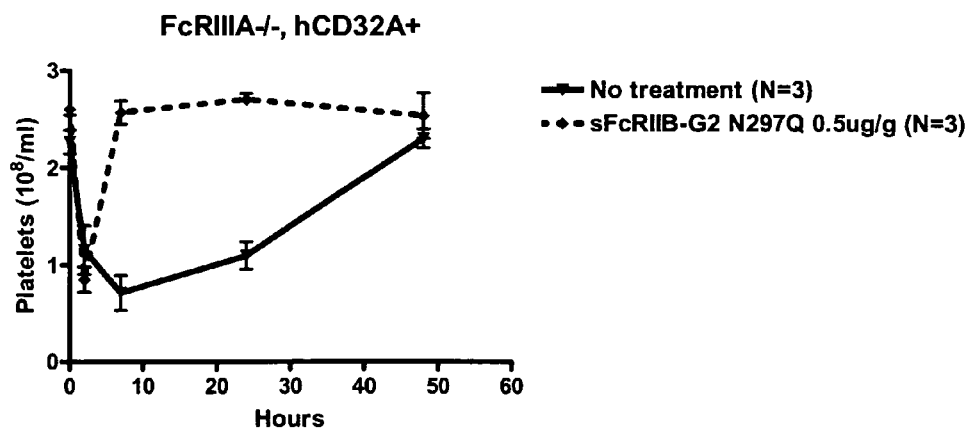
Figure 15:
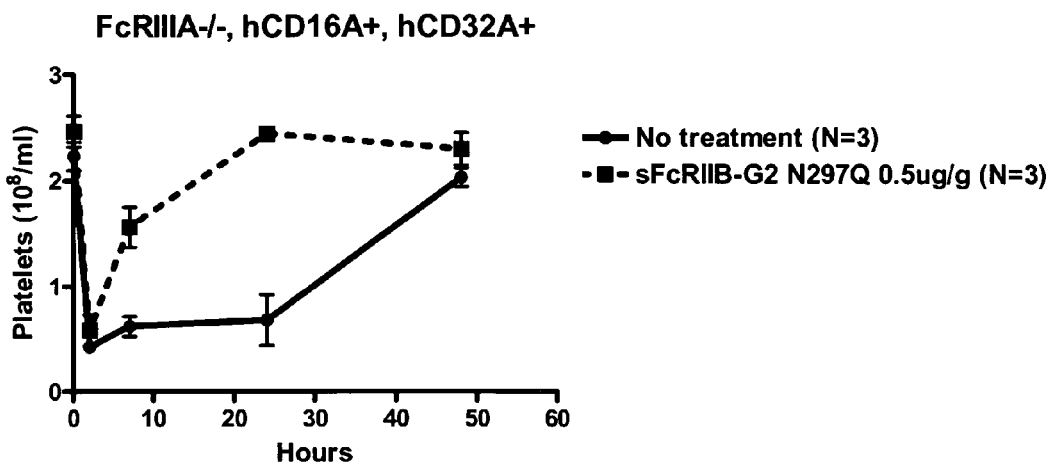

C. Additional mice were injected 3 hours after ch6A6 with combination of sFcγRIIB-G2 N297Q and either 5.1 N297Q or 22.1 N297Q at low concentrations. Data indicate that although low concentration (0.2 μg/g) of sFcγRIIB-G2 N297Q does not cure mFcγRIIA-/-, hCD16A+ mice from ITP. Combination of low concentration (0.2 μg/g) of sFcγRIIB-G2 N297Q and low concentration (0.125 μg/g) of anti-FcγRIIIA antibodies cures mice from ITP. Data indicate that sFcγRIIB-G2 N297Q and 5.1 N297Q or 22.1 N297Q can be used in combination therapy of ITP FIG. 15 Use of sFcγRIIIA-G2 in ITP Prevention in mFcγRIIIA-/- hCD32A+ Mice.

ITP was induced groups of single transgenic (mFcγRIIIA-/- hCD32A+, FIG. 13) or double transgenic (mFcγRIIIA-/- hCD16A+ hCD32A+, FIG. 14) mice by i.p. injection of 0.1 μg/g ch6A6 at time 0. Two hours later, the number of platelets in the plasma was determined to confirm the presence of ITP. Three hours later, mice were injected i.v. with 0.5 μg/g sFcγRIIB-G2 N297Q (arrow).

Figure 16:
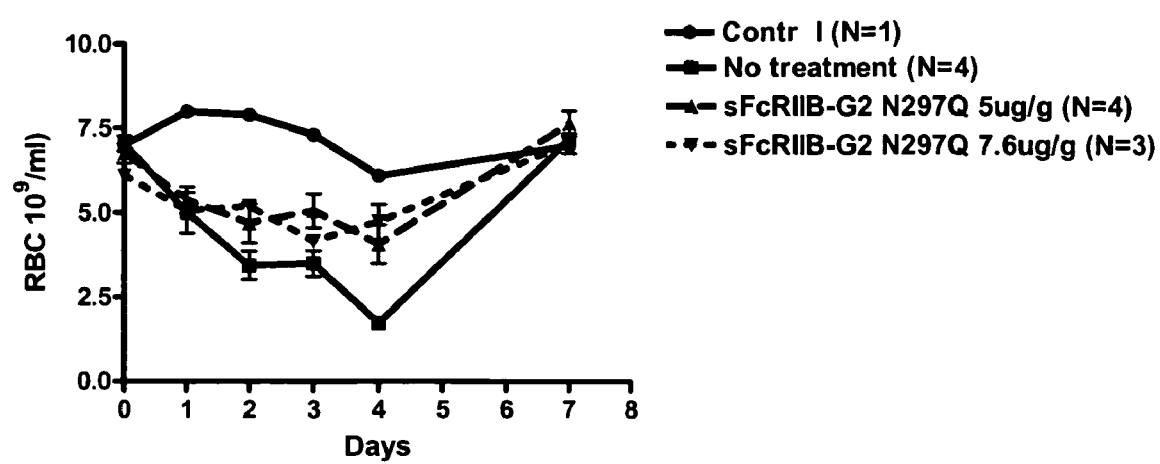

FIG. 16 AHA Prevention in muFCγRIII-/-, huFCγRIIIA Transgenic Mice using sFcγRIIB-G2-N297Q mFcγRIIIA-/- hCD16A+ transgenic mice were injected iv with 5 μg/g or 7.6 μg/g sFcγRIIB-G2-N297Q on day 0. Three hours later, AHA was induced by administering a pathogenic anti-mouse red blood cells (RBC) antibody (34-3C) ip (50 μg/mouse). RBC counts were determined at Day 0 (pre-immunization) as well as at days 1, 2, 3, 4, and 7 post-34-3C injection.

5. DETAILED DESCRIPTION OF THE INVENTION

5.1 Soluble FcγR Proteins

The present invention encompasses soluble FcγR proteins, e.g., the extracellular region of FcγR comprising an Fcγ binding site. The invention particularly relates to soluble FcγRIIIA and FcγIIB proteins. In one embodiment, the soluble protein of the invention corresponds to the extracellular region of FcγRIIIA, positions 140-715 of the cDNA encoding FcγRIIIA. In another embodiment, the soluble protein corresponds to the extracellular region of FcγRIIB, positions 137-676 of the cDNA encoding FcγRIIB. In some embodiments, the invention encompasses soluble FcγRIIIB and FcγRIIA proteins.

The invention also encompasses soluble FcγR proteins comprising any of the allelic variants known to those skilled in the art, e.g., such as those disclosed in Warmerdam et al., 1991, *Journal of Immunology*, 147: 1338-43; Kim et al., 2001, J. Mol. Evol. 53: 1-9; Fijen et al., 2000, Clin. Exp. Immunol. 120: 338-345; Fujiwara et al., 1999 Vox Sang. 77: 218-222; Petra et al., 1990, J. Exp. Med. 172: 19-25, Nagarajan et al., 1995, J. Biol. Chem. 270(43): 25762-70, Tebo et al., 2002, Clin. Exp. Immunol. 130: 300-6; Sorge et al,. 2003, Tissue Antigens, 61: 189-202; (all of which are incorporated herein by reference in their entireties). In some embodiments, the invention encompasses soluble FcγR proteins comprising amino acid substitutions at one or more positions that correspond to the polymorphic variants of FcγRs. In some embodiments, the invention encompasses any of the known polymorphic variants of FcγRIIIA, including but not limited to V158F, D105E, G130D, F134S, Y141H, and T142I. In other embodiments, the invention encompasses any of the allotypic variants of FcγRIIA, such as FcγRIIA-R131 or FcγRIIA-H131. The invention also encompasses allelic variants of FcγRIIIB termed NA1 and NA2 which may have altered phagocytic properties.

The invention encompasses engineering the soluble FcγR proteins using recombinant DNA technology known to those skilled in the art for modulating the affinity of the soluble FcγR to a molecule comprising an Fcγ region, e.g., an immune complex. The soluble FcγR proteins of the invention bind an immune complex specifically as determined by in vivo and in vitro standard assays discussed herein in Section 5.2, and known to those skilled in the art, e.g., ELISA assays or Biacore.

In one specific embodiment, molecules of the invention bind an immune complex with a dissociation constant or $K_d$ ($K_{on}/K_{off}$) in the range of 1-10 nM as determined by immunobased assays or any other assays known to one skilled in the art of measuring and quantitating dissociation constants of interacting molecules, e.g., Biacore, ELISA. In some embodiments, molecules of the invention bind an immune comples with a Kd of less than $10^{-10}M$, less than $5 \times 10^{-10}M$, less than $10^{-8}M$, less than $5 \times 10^{-8}M$, less than $10^{-7}M$, less than $5 \times 10^{-7}M$, less than $10^{-6}M$, less than $5 \times 10^{-6}M$, less than $10^{-5}M$, less than $5 \times 10^{-5}M$, less than $10^{-4}M$, less than $5 \times 10^{-4}M$, less than $10^{-3}M$, less than $5 \times 10^{-3}M$.

In some embodiments, the invention encompasses fusion proteins comprising an extracellular region of an FcγR covalently linked to any molecule that binds a FcRn (Fc Receptor neonate), wherein said fusion protein preferably does not bind an FcγR. Molecules that bind an FcRn include for example IgG molecules or portions thereof that contain and Fc region or a portion thereof, e.g., IgG1 subclass of IgGs, but may also be any other IgG subclasses of given animals. For example, in humans, the IgG class includes IgG1, IgG2, IgG3, and IgG4; and mouse IgG includes IgG1, IgG2a, IgG2b, IgG2c and IgG3. IgG molecules may comprise at elast one or more amino acid modification that alters their binding affinities for FcγRs and or FcRns. Various site-specific mutagenesis experiments in the Fc region of mouse IgGs have led to identification of certain critical amino acid residues involved in the interaction between IgG and FcRn (Kim et al., *Eur. J. Immunol.*, 240:2429-2434, 1994; Medesan et al., *Eur. J. Immunol.*, 26:2533, 1996; Medesan et al., *J. Immuno.*, 158:2211-2217, 1997; and International Publication No. WO 02/60919; all of which are incorporated herein by reference in their entireties) which are encompassed within the invention.

In certain embodiments, the dimeric fusion proteins of the invention are at least bivalent in that they comprise two soluble extracellular regions of an FcγR wherein each soluble extracellular region contains a binding site for an Fc constant region. Preferably, the soluble extracelullar regions are from the same FcγR, and, more preferably, have the same amino acid sequence. In other embodiments, the soluble extracellular regions are from different FcγRs, i.e., have different specificities, such that the dimeric fusion protein is at least bi-specific. The dimeric fusion proteins of the invention may further comprise a molecule fused to each soluble extracellular region of the FcγRs, wherein the molecule increases the stability (e.g., the serum half-life) of the dimeric fusion proteins. These molecules are preferably the Fc domain of an immunoglobulin, preferably, of an IgG, most preferably, the hinge-constant region of the immunoglobulin Fc. Such molecules may contain one or more additional binding domains, for example, a binding domain for FcRn, and, preferably, do not bind an FcγR. Thus, such molecules of the invention may be at least trivalent, in that they comprise at least three binding sites. In other specific embodiments, the invention includes monomeric fusion proteins having a soluble extracellular region of an FcγR that contains a binding site for an Fc constant region fused to a molecule that increases the stability of the soluble extracellular region. Such monomeric fusion proteins may be monovalent (i.e., have only one binding site) but may also comprise additional binding sites, for example, when the soluble extracellular region is fused to an Fc constant or hinge-constant domain, that domain may also have a binding site for, e.g. FcRn and, as such, are at least bivalent.

In one embodiment, the soluble FcγR proteins of the invention bind an immune complex with the same avidity as the wild-type FcγR binds the immune complex. In another embodiment, the soluble FcγR proteins of the invention are engineered using standard recombinant DNA technology known to those skilled in the art, to comprise at least one amino acid modification in the extracellular region, such that the variant FcγR binds an immune complex with a higher avidity relative to a molecule comprising the wild-type FcγR extracellular region. In some embodiments, the soluble FcγR proteins bind an immune complex with at least 25%, at least 35%, at least 45%, at least 55%, at least 65%, at least 75%, at least 85%, at least 90%, at least 95%, at least 99% higher avidity relative to a molecule comprising a wild type FcγR extracellular region. The soluble FcγR proteins of the invention block binding of an FcγR to an immune complex as determined by immune complex blocking assays discussed herein and known to those skilled in the art. In one embodiment, the soluble FcγR proteins of the invention reduce or inhibit immune complex binding to an Fcγ by approximately 25%, 35%, 45%, 50%, 55%, 65%, 75%, 85%, 95%, or 99%, as determined by immune complex blocking assays discussed herein and known to those skilled in the art.

In one embodiment, a polypeptide of the invention comprising an Fcγ binding site can be isolated from cells or tissue sources by an appropriate purification scheme using standard protein purification techniques. In another embodiment, a polypeptide of the invention comprising an Fcγ binding site of the invention is produced by recombinant DNA techniques. Alternative to recombinant expression, a polypeptide comprising an Fcγ binding site can be synthesized chemically using standard peptide synthesis techniques.

The present invention encompasses fusion proteins comprising a polypeptide which specifically binds the Fc region of an immunoglobulin (e.g., the extracellular soluble region of an activating FcγR, such as FcγRIIIA, or an inhibitory FcγR, such as FcγRIIB) covalently linked to a heterologous polypeptide. In preferred embodiments, the polypeptide which specifically binds the Fc region of an immunoglobulin is the extracellular region of an FcγR receptor, comprising an Fc binding site. In another preferred embodiment, the heterologous polypeptide fused to the extracellular region of an FcγR is an immunoglobulin constant region, more preferably, a hinge-constant region, such that the resulting fusion polypeptide specifically binds an immune complex. Fusion of the extracellular region of FcγR to any stable plasma protein known in the art, including but not limited to albumin, lipoproteins, apolipoproteins, and transferrin is contemplated in the methods and compositions of the invention to form the dimeric fusion proteins. In other embodiments, the invention encompasses fusion proteins comprising a polypeptide which specifically binds the Fcγ region of an immunoglobulin (e.g., the extracellular soluble region of an activating FcγR, such as FcγRIIIA, or an inhibitory FcγR, such as FcγRIIB) covalently linked to a heterologous molecule that is capable of dimerizing the extracellular region of the FcγR, such that the integrity and structure of the extracellular region of the FcγR is not compromised. In certain embodiments, the heterologous molecule fused to the extracellular region of an FcγR comprises a residue that can form a disulfide bond, e.g., cysteine. In a specific embodiment, the heterologous molecule fused to the extracellular region of an FcγR comprises a peptide of at least 5 amino acids, at least 10 amino acids, at least 20 amino acids, at least 30 amino acids, at least 40 amino acids, at least 50 amino acids, at least 100 amino acids, or at least 200 amino acids, comprising an amino acid residue that can form a disulfide bond. The invention encompasses heterologous molecules fused to the extracellular region of an FcγR comprising a residue that can form a disulfide bond, other than a cysteine residue, or other linkages, including but not limited to, Pen (Penicillamine), Mpr (mercapto propionyl), or Mvl (mercaptovaleryl).

The invention encompasses variants of the fusion proteins comprising a polypeptide which specifically binds the Fcγ region of an immunoglobulin (e.g., the extracellular soluble region of an activating FcγR, such as FcγRIIIA, or an inhibitory FcγR, such as FcγRIIB) covalently linked to a heterologous polypeptide. The variants of the invention are generated using any standard recombinant technique known to those skilled in the art. In a specific embodiment, the invention encompasses a variant of a fusion protein comprising the extracellular region of an FcγR fused to an immunoglobulin constant region, wherein the immunoglobulin constant region comprises at least one amino acid modification, which modification modulates the affinity of the immunoglobulin constant region for a soluble FcγR protein. In a specific embodiment, the invention encompasses a variant of the constant region that has been engineered to contain at least one amino acid modification to modulate its affinity for a soluble FcγR, using standard methods known in the art, or using any of the methods disclosed in U.S. Provisional Application Nos. 60/439,498; 60/456,041, filed on Jan. 9, 2003 and Mar. 19, 2003 respectively, and U.S. Provisional Application No. 60/514,549 filed on Oct. 23, 2003, and U.S. application Ser. No. 10/74,922 filed on Jan. 9, 2004, all of which are incorporated herein by reference in their entirety. In a specific embodiment, the invention encompasses a variant of a constant region comprising an amino acid modification, which modification lowers its affinity for an FcγRIIIA, e.g., a variant disclosed in U.S. Provisional Application Nos. 60/439,498; 60/456,041, filed on Jan. 9, 2003 and Mar. 19, 2003 respectively, and U.S. Provisional Application No. 60/514,549 filed on Oct. 23, 2003 and U.S. application Ser. No. 10/754,922 filed on Jan. 9, 2004. The invention encompasses a variant of a immunoglobulin constant region using any of the methods disclosed in U.S. Provisional Application Nos. 60/439,498; 60/456,041, filed on Jan. 9, 2003 and Mar. 19, 2003, respectively, and U.S. Provisional Application No. 60/514,549 filed on Oct. 23, 2003, and U.S. application Ser. No. 10/754,922 filed on Jan. 9, 2004.

In certain embodiments, the invention encompasses a variant of a fusion protein of the invention wherein the constant region of the immunoglobulin fused to the extracellular region of an FcγR, comprises at least one or more amino acid modifications, which modifications provide additional or different properties, such as altered immunogenicity or half-life of the resultant polypeptide. The changes in the constant region may range from one or more amino acid residues to the complete redesign of constant region. Changes contemplated within the present include for example, changes that affect the interaction with membrane receptors, complement fixation, persistence in circulation, and other effector functions, and such changes are well known to one skilled in the art. For example, the hinge or other regions can be modified as described in U.S. Pat. No. 6,277,375, which is incorporated herein by reference in its entirety. In some embodiments, it will often be advantageous to delete or alter amino acids of the Fcγ region. For example, in one embodiment, the fusion proteins of the invention comprising one or more amino acid substitutions or deletions (relative to the parental naturally occurring immunoglobulin constant region) result in a reduced interaction between the Fcγ region of the fusion protein and FcγRIIA and FcγRIIIA (e.g., to minimize neutrophil targeting) and/or increased binding of the Fcγ region to FcγRIIB (e.g., to increase FcγRIIB-mediated inhibition of effector cell activation; see Bolland and Ravetch, 1999, Adv. in Immunol. 72:149, which is incorporated herein by reference in its entirety). Specific mutations effecting the desired changes in binding can be identified for example, by selection using display of mutant Fcγ libraries expressed on the surface of microorganisms, viruses or mammalian cells, and screening such libraries for mutant Fcγ variants having the desired property or properties. In addition, the invention encompasses engineering the fusion proteins of the invention based on structural and biochemical data available on Fcγ-FcγR interactions (Shields et al., 2001, J Biol. Chem. 276:6591-6604; Sondermann et al.; Deisenhofer et al., 1981, Biochemistry, 20(9): 2361-70; Burmeister et al., 1994, Nature, 342: 379-383; all of which are incorporated herein by reference in their entirety). In some embodiments, the invention encompasses a mutation of any of amino acids within residues 233-239, which is the binding site on human antibodies for FcγR (Canfield et al. 1991, J Exp Med 173:1483-91; Woof et al., 1986, Mol. Imm. 23:319-30; Duncan et al., 1988, Nature 332:563; all of which are incorporated herein by reference in their entirety). Exemplary Fcγ region mutations include, for example, L235E, L234A, L235A, and D265A, which have been shown to have low affinity for all FcγR,(Clynes et al., 2000, Nat. Med. 6:443-46; Alegre et al., 1992, J Immunol 148:3461-68; Xu et al., 2000, Cell Immunol 200:16-26; all of which are incorporated herein by reference in their entirety). Additional Fcγ region modifications purported to affect FcγR binding are described in WO 00/42072 and U.S. Pat. No. 6,194,551, both of which are incorporated herein by reference in their entirety.

In other embodiments, the invention encompasses a variant of a fusion protein comprising the extracellular region of an FcγR fused to an immunoglobulin constant region, wherein the extracellular region of the FcγR comprises at least one or more amino acid modifications, which modifications modulate the affinity of the extracellular region for an Fc containing polypeptide. The invention encompasses a variant of the extracellular region of amino acids in the extracellular region crucial to the interaction between the Fcγ receptor and an Fc containing polypeptide such as those known in the art. See e.g., Hulett et al. 1993, Eur J. Immunol; Hulett et al., 1995, Journal of Biological Chem., 270(36): 21188-94; Hulett et al., 1994, Journal of Biological Chem., 269(21): 15287-93; Warmerdam et al., 1991, J. Immunology, 147: 1338-43; Warmerdam et al., 1990, Journal of Ex. Med. 172: 1925), all of which are incorporated herein by reference in their entirety. The invention encompasses variants of an FcγR extracellular region disclosed in U.S. Pat. No. 5,985,599, all of which is incorporated herein by reference in its entirety.

In other embodiments, the invention encompasses a fusion protein comprising the extracellular region of an FcγR fused to an immunoglobulin constant region, wherein the extracellular region of the FcγR comprises a chimeric extracellular region, so that the chimeric extracellular region binds an immune complex as assessed by methods known to one skilled in the art and disclosed herein. The chimeric extracellular region comprises one or more regions from an FcγR using for example gene shuffling techniques known in the art. In a specific embodiment, the chimeric extracellular region comprises a region corresponding to a region from FcγRIIA, and a region corresponding to a region from FcγRIIB. In another specific embodiment, the chimeric extracellular region comprises a region corresponding to a region from FcγRIIIA, and a region corresponding to a region from FcγRIIB.

The invention particularly relates to fusion proteins comprising the extracellular region of an Fcγ (e.g., activating FcγR such as FcγRIIIA or inhibitory FcγR such as FcγRIIB) fused to an IgG2 constant region. Although not intending to be bound by any mechanism of action, there is little or no affinity between the IgG2 constant region and the extracellular region of an FcγR, and thus the IgG2 constant region is the preferred constant region for use in accordance with the invention. Furthermore, the inclusion of the hinge region in the fusion protein will allow flexibility of the two receptor arms and covalent disulfide linkage of each monomer, comprising the extracellular region of an FcγR and the IgG2 hinge-constant region, i.e., forms dimeric fusion protein. In accordance with the invention, fusion of an FcγR extracellular region to an IgG2 constant region, comprises fusing the C-terminus of the extracellular region of an FcγR to the N-terminus of the "hinge-constant region", which is herein defined as the region encompassing the hinge region of IgG2, the CH2, and CH3 domains of the IgG2 constant region.

In a specific embodiment, the invention encompasses the fusion protein shown in SEQ ID. NO. 1, corresponding to the soluble extracellular region of FcγRIIIA fused to the IgG2 constant region. In another embodiment, the invention encompasses a variant of SEQ ID. NO. 1, wherein the protein comprises one or more amino acid modifications so that the fusion protein has an enhanced stability relative to the fusion protein of SEQ ID NO. 1. In a more specific embodiment, the invention encompasses modification of residues, preferably within residues 183 and 184 of SEQ. ID. NO. 1 so that the protein shows enhanced stability and no detectable degradation product when analyzed by SDS-PAGE. In one specific embodiment, the invention encompasses any of variants V1-V4 with SEQ ID. NOs 33, 35, 37 or 39. Although not intending to be bound by any particular mechanism of action, the fusion proteins of the invention with enhanced stability are not cleaved at any position between the FcγRIIIA and IgG2 Fc domains. A "stable fusion protein" as used herein refers to a fusion protein that undergoes minimal to no detectable level of degradation during production and/or storage as assessed using common biochemical and functional assays known to one skilled in the art, and can be stored for an extended period of time with no loss in biological activity, e.g., binding to FcγR. Assays which can be used to determine the binding of the modified fusion proteins with altered stabilities to an FcγR include for example immune complex binding assays, ELISA assays, etc. e.g., SDS-PAGE analysis Preferably, the fusion proteins of the present invention exhibit stability at the temperature ranges of 20-25° C., preferably at 25° C., for at least one month, at least 2 months, more preferably at least 4 months, as assessed by SDS-PAGE analysis or high performance size exclusion chromatography (HPSEC) or any other method known to one skilled in the art. In some embodiments, the fusion proteins of the present invention exhibit stability at the temperature ranges of 2-8° C., preferably at 4° C., for at least one month, at least 2 months, more preferably at least 4 months, as assessed by SDS-PAGE analysis or high performance size exclusion chromatography (HPSEC) or any other method known to one skilled in the art. Preferably, the fusion proteins of the present invention have low to undetectable levels of degradation after the storage for the defined periods as set forth above. Preferably, no more than 5%, no more than 4%, no more than 3%, no more than 2%, no more than 1%, and most preferably no more than 0.5%, of protein degrades as measured by SDS-PAGE analysis or HPSEC, after the storage for the defined periods as set forth above. In most preferred embodiments, the fusion proteins of the present invention will exhibit almost no loss in biological activity during a prolonged storage under the conditions described above, as assessed by standard methods known in the art. The fusion proteins of the present invention retain, after the storage for the above-defined periods, more than 80%, more than 85%, more than 90%, more than 95%, more than 98%, more than 99%, or more than 99.5% of the initial biological activity prior to the storage. Certain of the fusion proteins of the invention that have been modified to have an enhanced stability relative to the fusion protein with SEQ. ID. No. 1, but bind FcγRIII with a similar affinity as the fusion protein of SEQ. ID. No. 1, as determined using standard assays known in the art and exemplified herein (Example 6.4).

The invention encompasses modifying a fusion protein of the invention comprising the soluble extracellular region of FcγRIIIA fused to the IgG2 constant region so that the protein has an enhanced stability relative to the wild type protein. The modifications include deletions, substitutions, and insertions, and may include introduction of linkers such that the the structure and function of the fusion protein is not compromised, e.g., the fusion protein binds an FcγR or an immune complex with a similar or an improved affinity as assessed using methods known in the art for monitoring Fc-FcγR interactions such as those disclosed and exemplified herein. Linkers that may be used in the constructs of the invention preferably comprise at least one amino acid, at least 5 amino acids, at least 10 amino acids, at least 15 amino acids, or at least 20 amino acids and preferably no more than 20 amino acids. Preferably, the linkers used in the constructs of the invention comprise multiple repeats of an amino acid such as glycine, alanine, or repeats of any residue that does not affect the function or structure of the fusion protein. The linkers of the invention may comprise any amino acid, including charged, polar, and non-polar amino acids. In some embodiments, the insertions include sequences corresponding to a sequence from any FcγR, including activating and inhibitory FcγRs so that the fusion protein retains the ability to bind FcγR with a similar or an improved affinity as assessed using methods known in the art for monitoring Fc-FcγR interactions such as those disclosed and exemplified herein. In some embodiments, the insertions include sequences corresponding to a sequence from FcγRIIB, since FcγRIIB is not susceptible to degradation. In a specific embodiment, the insertion comprises a sequence corresponding to amino acids 169-181 of FcγRIIB.

In one specific embodiment, the invention encompasses a fusion protein comprising the soluble extracellular region of FcγRIIIA fused to the IgG2 constant region (SEQ ID Nos. 33 and 34) wherein amino acids 176 to 192 have been replaced with the flexible linker sequence GGGGS. In another embodiment, amino acids 176 to 192 may be replaced with any linker known in the art which is at least one amino acid, at least 5 amino acids in length, at least 10, at least 15 amino acids or at least 20 amino acids in length. In another specific embodiment, the invention encompasses a fusion protein comprising the soluble extracellular region of FcγRIIIA fused to the IgG2 constant region (SEQ ID Nos. 35 and 36) wherein amino acids 176 to 192 have been replaced with the flexible linker sequence GGGGS and residue 170 of FcR is changed from N to Q so that the fusion protein is not glycosylated.

In one specific embodiment, the invention encompasses a fusion protein comprising the soluble extracellular region of FcγRIIIA fused to the IgG2 constant region (SEQ ID Nos. 37 and 38) wherein amino acids 176 to 192 have been replaced with the amino acids 172-181 of FcγRIIB-G2. In another specific embodiment, the invention encompasses a fusion protein comprising the soluble extracellular region of FcγRIIIA fused to the IgG2 constant region (SEQ ID Nos. 39 and 40) wherein amino acids 170 to 192 have been replaced with the amino acids 169-181 of FcγRIIB-G2.

In another embodiment, the invention encompasses the fusion protein shown in SEQ. ID. No. 2, corresponding to the soluble extracellular region of FcγRIIB fused to the IgG2 constant region. In certain embodiments, the invention encompasses allelic variants of an FcγR, particularly allelic variants in the FcγR extracellular regions. In some embodiments, one or more cysteines in the hinge region of FcγRIIB may be modified so that the fusion protein has an enhanced stability relative to the wild type protein. The cysteines in the hinge region that may be modified in accordance with the invention are for example, 185, 186, 189, and 192 of sFcγRIIB-G2 (SEQ ID NO. 2).

In some embodiments, one, more preferably two, or most preferably three of the four cysteine residues in the hinge region IgG2 Fc which are at positions 196, 197, 200, and 203 of FcγRIIIA-G2 (SEQ ID No. 1), are modified, e.g., deleted or changed to another amino acid such as Ser. In other embodiments, one, more preferably two, or most preferably three of the four cysteine residues in the hinge region IgG2 Fc which are at positions and at residues 185, 186, 189 and 192 of sFcγRIIB-G2 (SEQ. ID. No. 2), are modified, e.g., deleted or changed to another amino acid such as Ser. Although not intending to be bound by any particular mechanism of action, modification of cysteine residues in the hinge region would decrease the number of disulfide bonds which need to be formed and can thus result in a higher percentage of correctly folded protein secreted into the conditioned medium. It is also likely that reducing the number of disulfides will improve the overall kinetics of folding and lead to higher levels of overall secretion of the fusion protein.

In certain embodiments, the invention encompasses fusion proteins comprising the extracellular region of FcγRIIA. In yet other embodiments, the invention encompasses allelic variants of FcγRIIA, such as those described by Warmerdam et al., 1991, Journal of Immunology, 147: 1338-43, which is incorporated herein by reference in its entirety, e.g., a variant at position 131, such as a substitution with histidine or arginine. In a specific embodiment, the invention encompasses a fusion protein comprising an allelic variant of the extracellular region of an FcγRIIA fused to the IgG2 constant region such as that disclosed in SEQ ID NO. 3. In another specific embodiment, the invention encompasses a fusion protein comprising an allelic variant of the extracellular region of an FcγRIIA fused to the IgG2 constant region such as that disclosed in SEQ ID NO. 4. The invention encompasses fusion proteins comprising the extracellular region of an FcγR allelic variants known in the art such as those disclosed in Warmerdam et al., 1991, *Journal of Immunology,* 147: 1338-43; Kim et al., 2001, J. Mol. Evol. 53: 1-9; Fijen et al., 2000, Clin. Exp. Immunol. 120: 338-345; Fujiwara et al., 1999 Vox Sang. 77: 218-222; Petra et al., 1990, J. Exp. Med. 172: 19-25, Nagarajan et al., 1995, J. Biol. Chem. 270(43): 25762-70, Tebo et al., 2002, Clin. Exp. Immunol. 130: 300-6; Sorge et al,. 2003, Tissue Antigens, 61: 189-202; all of which are incorporated herein by reference in their entireties.

In preferred embodiments, the FcγR extracellular region and/or the IgG2 constant region is from a human, e.g., has the amino acid sequence of a human FcγR extracellular region and the amino acid sequence of a human IgG2 constant region (e.g., Genbank Accession No. J00230 V00554; Germline DNA=GI:184750; Protein Accession P01859; which are incorporated by reference). The invention encompasses allotypic variants of IgG2, particularly at position 282. Alternatively, the FcγR extracellular regions and the IgG2 constant regions used in the methods and the compositions of the invention may be from any animal origin, including birds and mammals (e.g., human, non-human primate, murine, donkey, sheep, rabbit, goat, guinea pig, camel, horse, or chicken).

In a most preferred embodiment, the invention encompasses dimeric fusion protein comprising two identical polypeptide chains, such that each said chain comprises an extracellular region of FcγRIIIA comprising an Fcγ binding site, joined to a hinge-constant region of IgG2, wherein the dimeric fusion protein specifically binds an immune complex. In other embodiments, said dimeric fusion protein is univalent, i.e., has a single binding site. In yet another preferred embodiment, the invention encompasses a dimeric fusion protein comprising two identical polypeptide chains, such that each said chain comprises an extracellular region of FcγRIIB comprising an Fcγ binding site, joined to a hinge-constant region of IgG2, wherein the dimeric fusion protein specifically binds an immune complex. In yet other embodiments, said dimeric fusion protein is univalent, i.e., has a single binding site.

The fusion proteins of the invention comprising an FcγR extracellular region e.g., FcγRIIIA, joined to an immunoglobulin constant region specifically bind an immune complex as determined by assays known to those skilled in the art and discussed herein in section 5.2. In a specific embodiment, the fusion proteins of the invention comprising an FcγR extracellular region e.g., FcγRIIIA, joined to an immunoglobulin constant region bind an immune complex with an avidity comparable to the wild-type FcγR. In another specific embodiment, the soluble fusion proteins of the invention comprising an FcγR extracellular region e.g., FcγIIIA, joined to an immunoglobulin constant region, are engineered such that the FcγR extracellular region comprises at least one amino acid modification such that the fusion protein comprising the variant FcγR extracellular region binds an immune complex with a greater avidity comparable to the wild-type FcγR, lacking said at least one amino acid modification.

The dimeric fusion proteins of the invention comprising an extracellular region of FcγR have therapeutic utility as single therapeutic agents for the treatment and/or prevention of an autoimmune disease, as discussed in section 5.4. Although not intending to be bound by any mechanism of action, the utility of the fusion proteins comprising an FcγR extracellular region e.g., FcγRIIIA, joined to an immunoglobulin constant region, as single therapeutic agents, is that they inhibit or reduce the interaction of an immune complex to Fcγ as determined by in vitro and in vivo immune complex blocking assays discussed herein and known to those skilled in the art. Specifically, the molecules of the invention (e.g., fusion proteins comprising an activating FcγR extracellular region, soluble extracellular regions of an activating FcγR) modulate autoantibody-mediated activation and triggering of an autoimmune disease. In a specific embodiment, a fusion protein comprising an activating FcγR extracelluar region e.g., FcγRIIIA, joined to an immunoglobulin constant region, reduces or inhibits immune complex binding to FcγR by approximately 25%, 35%, 45%, 55%, 65%, 75%, 85%, 95%, or 99% as determined by in vitro and in vivo immune complex blocking assays discussed herein and known to those skilled in the art.

The invention encompasses engineering the molecules of the invention using standard recombinant DNA technology known to those skilled in the art. In a specific embodiment, the invention encompasses engineering the fusion proteins of the invention comprising an extracellular region of FcγR, e.g., FcγRIIIA or FcγRIIB, such that the fusion proteins comprise at least one amino acid modification in the extracellular region, which modification lowers the affinity of the soluble extracellular protein for an agent by at least 25%, at least 35%, at least 45%, at least 55%, at least 65%, at least 75%, at least 85%, at least 95%, or at least 99%, e.g., an antibody that specifically binds the extracellular region of an FcγR for the treatment and/or prevention of an autoimmune disease, so that the resulting modified fusion protein can be administered in combination with that agent. In another specific embodiment, the invention encompasses engineering the fusion proteins of the invention comprising an extracellular region of FcγR, e.g., FcγRIIIA or FcγRIIB, such that the fusion proteins comprise at least one amino acid modification in the extracellular region, which modification lowers the affinity of the soluble extracellular protein for an agent by at least 100-fold, preferably 1000-fold, e.g., an antibody that specifically binds the extracellular region of an FcγR for the treatment and/or prevention of an autoimmune disease, so that the resulting modified fusion protein can be administered in combination with that agent. The modified fusion protein comprising at least one amino acid modification in the extracellular region, specifically binds an immune complex. In one embodiment, the modified fusion protein comprising at least one amino acid modification in the extracellular region specifically binds an immune complex with a higher avidity relative to a wild-type extracellular region.

In a specific embodiment, the invention encompasses use of the fusion proteins of the invention comprising the extracellular region of an activating FcγR, e.g., FcγRIIIA, for the treatment and/or prevention of an autoimmune disease in combination with one or more FcγRIIIA binding proteins (See section 5.4.2). In one embodiment, the fusion proteins of the invention comprising the extracellular region of an activating FcγR, e.g., FcγRIIIA, are used in combination with one or more other FcγRIIIA binding proteins, excluding the extracellular region of FcγRIIIA, such that the fusion proteins have been engineered, using recombinant DNA technologies known to those skilled in the art, to reduce the affinity of the fusion protein for the one or more other FcγRIIIA binding proteins. FcγRIIIA binding proteins encompassed by the invention include, for example, antibodies that specifically bind FcγRIIIA (See Section 5.4.2).

In one specific embodiment, the invention encompasses a dimeric fusion protein comprising two identical polypeptide chains, each chain comprising a variant extracellular region of FcγIIIA joined to a hinge-constant region of IgG2, wherein said variant extracellular region comprises at least one amino acid modification relative to a wild-type extracellular region of FcγRIIIA, such that a 3G8 monoclonal antibody (e.g., a humanized 3G8 monoclonal antibody) or an antibody that competes with a 3G8 antibody for binding the extracellular region of FcγRIIIA, binds said dimeric fusion protein with a lower affinity than said monoclonal 3G8 antibody binds said wild-type extracelluar region, and wherein the dimeric fusion protein specifically binds an immune complex. In one embodiment, the invention encompasses a dimeric fusion protein comprising a variant extracelluar region of FcγRIIIA comprising at least one amino acid modification (e.g., substitution) in the 3G8 binding site of FcγRIIIA that lowers the affinity of the 3G8 antibody for the variant FcγRIIIA extracellular region. The one or more amino acid modifications in the 3G8 binding site of FcγRIIIA may be a modification of any amino acid in the binding site of the 3G8 antibody for FcγRIIIA, e.g., a modification of any amino acid residues within 109-114 and/or any amino acids within amino acids 150-160. The one or more amino acid modification in the 3G8 binding site of FcγRIIIA includes, but is not limited to, a modification in the BC loop (amino acids Trp110 to Ala 114), which is the loop between the "B" b-sheet and the "C", β-sheet as determined by a crystallographic structure of an Fcγ fragment in complex with FcγRIII (Sondermann et al., 2000, Nature, 406: 267-273) of FcγRIIIA, a modification in the FG loop of FcγRIIIA (amino acids Val 155 to Lys 158), a modification in the C strand FcγRIIIA (amino acids His 116 to Thr 119), and a modification in the C' strand of FcγRIIIA (amino acids Asp 126 to His 132). Alternatively, the one or more amino acid modifications in the extracellular region of an FcγRIIIA is in any region, excluding the 3G8 binding site. In one specific embodiment, the amino acid modification in the extracellular region of FcγRIIIA comprises a substitution at position 112 with aspartic acid, at position 113 with lysine, and at position 114 with proline. In another embodiment, the amino acid modification in the extracellular region of FcγRIIIA comprises a substitution at position 160 with phenylalanine. In yet another embodiment, the amino acid modification in the extracellular region of FcγRIIIA comprises a substitution at position 154 with asparagine and at position 155 with isoleucine. Preferably, a 3G8 antibody does not inhibit binding of a variant fusion protein of the invention as determined by immune complex blocking assays, as described for example in Example 6.

In a specific embodiment, a fusion protein comprising a variant extracellular region of FcγRIIIA, comprising a substitution at position 112 with aspartic acid, at position 113 with lysine, and at position 114 with proline, specifically binds an immune complex, e.g., ch-4-4-40/BSA-FITC, as disclosed in Example 6, with a higher avidity relative to a protein comprising a wild-type extracellular region of FcγRIIIA, as determined by an immunobased assay, e.g., ELISA. In another embodiment, a 3G8 monoclonal antibody binds a fusion protein comprising a variant extracellular region of FcγRIIIA, comprising a substitution at position 112 with aspartic acid, at position 113 with lysine, and at position 114 with proline with a lower avidity relative to a protein comprising a wild-type FcγRIIIA extracellular region, as determined by an immunobased assay, e.g., an ELISA assay. In yet another embodiment, a 3G8 monoclonal antibody does not inhibit binding of fusion protein comprising a variant extracellular region of FcγRIIIA, comprising a substitution at position 112 with aspartic acid, at position 113 with lysine, and at position 114 with proline to an immune complex, as determined by immune complex blocking assays.

In another embodiment, a fusion protein comprising a variant extracellular region of FcγRIIIA, comprising a substitution at position 160 with phenylalanine, specifically binds an immune complex, e.g., ch-4-4-40/BSA-FITC, as disclosed in Example 6, with a comparable avidity relative to a protein comprising a wild-type extracellular region of FcγRIIIA, as determined by an immunobased assay, e.g. ELISA. In another embodiment, a 3G8 monoclonal antibody binds a fusion protein comprising a variant extracellular region of FcγRIIIA, comprising a substitution at position 160 with phenylalanine with a lower avidity relative to a protein comprising a wild-type FcγRIIIA extracellular region, as determined by an immunobased assay, e.g., an ELISA assay. In yet another embodiment, a 3G8 monoclonal antibody does not inhibit binding of fusion protein comprising a variant extracellular region of FcγRIIIA, comprising a substitution at position 160 with phenylalanine to an immune complex, as determined by immune complex blocking assays.

In another embodiment, a fusion protein comprising a variant extracellular region of FcγRIIIA, comprising a substitution at position 154 with asparagine and at position 155 with isoleucine, specifically binds an immune complex, e.g., ch-4-4-40/BSA-FITC, as disclosed in Example 6, with a comparable avidity relative to a protein comprising a wild-type extracellular region of FcγRIIIA, as determined by an immunobased assay, e.g., ELISA. In another embodiment, a 3G8 monoclonal antibody binds a fusion protein comprising a variant extracellular region of FcγRIIIA, comprising a substitution at position 154 with asparagine and at position 155 with isoleucine with a lower avidity relative to a protein comprising a wild-type FcγRIIIA extracellular region, as determined by an immunobased assay, e.g., an ELISA assay. In yet another embodiment, a 3G8 monoclonal antibody does not inhibit binding of fusion protein comprising a substitution at position 154 with asparagine and at position 155 with isoleucine to an immune complex, as determined by immune complex blocking assays.

In a specific embodiment, the invention encompasses use of the fusion proteins of the invention comprising the extracellular region of an inhibitory FcγR, e.g., FcγRIIB, for the treatment and/or prevention of an autoimmune disease in combination with other FcγRIIB binding proteins (See section 5.4.2). In one embodiment, the fusion proteins of the invention comprising the extracellular region of an inhibitory FcγR, e.g., FcγRIIB, are used in combination with one or more other FcγRIIB binding proteins, excluding the extracellular region of FcγRIIB, such that the fusion proteins have been engineered, using recombinant DNA technologies known to those skilled in the art, to reduce the affinity of the fusion protein for the one or more other FcγRIIB binding proteins. FcγRIIB binding proteins encompassed by the invention include, for example, antibodies that specifically bind FcγRIIB (See Section 5.4.2). In a specific preferred embodiment, the FcγRIIB binding proteins used in combination with a fusion protein of the invention comprising the extracellular region of FcγRIIB is an antibody, preferably a monoclonal antibody specific for FcγRIIB. Any FcγRIIB specific antibody known to those skilled in the art is contemplated in the methods and compositions of the invention. In a particular embodiment, the invention encompasses use of antibodies, preferably monoclonal antibodies which specifically bind FcγRIIB with a greater affinity than said antibodies bind FcγRIIA, such as those disclosed in U.S. Provisional Application 60/403,266, filed on Aug. 14, 2002, and U.S. application Ser. No 10/643,857, filed on Aug. 14, 2003, which are incorporated herein by reference in their entirety.

The invention also provides molecules with altered oligosaccharide content. Although not intending to be bound by a particulary mechanism of action, molecules with altered oligosaccharide content have altered affinities for FcγRIIIA, e.g., do not activate FcγIIIA. Oligosaccharides as used herein refer to carbohydrates containing two or more simple sugars and the two terms may be used interchangeably herein. Carbohydrate moieties of the instant invention will be described with reference to commonly used nomenclature in the art. For a review of carbohydrate chemistry, see, e.g., Hubbard et al., 1981 *Ann. Rev. Biochem.,* 50: 555-583, which is incorporated herein by reference in its entirety. This nomenclature includes for example, Man which represents mannose; GlcNAc which represents 2-N-acetylglucosamine; Gal which represents galactose; Fuc for fucose and Glc for glucose. Sialic acids are described by the shorthand notation NeuNAc for 5-N-acetylneuraminic acid, and NeuNGc for 5-glycolneuraminic.

In general, antibodies contain contain carbohydrate moieties at conserved positions in the constant region of the heavy chain, and up to 30% of human IgGs have a glycosylated Fab region. IgG has a single N-linked biantennary carbohydrate structure at Asn 297 which resides in the CH2 domain (Jefferis et al., 1998, *Immunol. Rev.* 163: 59-76; Wright et al., 1997, *Trends Biotech* 15: 26-32). Human IgG typically has a carbohydrate of the following structure; GlcNAc(Fucose)-GlcNAc-Man-(ManGlcNAc)$_2$. However variations among IgGs in carbohydrate content does occur which leads to altered function, see, e.g., Jassal et al., 2001 *Bichem. Biophys. Res. Commun.* 288: 243-9; Groenink et al., 1996 *J. Immunol.* 26: 1404-7; Boyd et al., 1995 *Mol. Immunol.* 32: 1311-8; Kumpel et al., 1994, *Human Antibody Hybridomas,* 5: 143-51. The invention encompasses molecules comprising a variation in the carbohydrate moiety that is attached to Asn 297. In one embodiment, the carbohydrate moiety has a galactose and/or galactose-sialic acid at one or both of the terminal GlcNAc and/or a third GlcNac arm (bisecting GlcNAc).

In some embodiments, the altered carbohydrate modifications modulate one or more of the following: solubilization of the molecule, facilitation of subcellular transport and secretion, promotion of assembly, and conformational integrity. Altering carbohydrate modifications in accordance with the methods of the invention includes, for example, increasing the carbohydrate content of the antibody or decreasing the carbohydrate content of the antibody. Methods of altering carbohydrate contents are known to those skilled in the art, see, e.g., Wallick et al., 1988, *Journal of Exp. Med.* 168(3): 1099-1109; Tao et al., 1989 *Journal of Immunology,* 143(8): 2595-2601; Routledge et al., 1995 *Transplantation,* 60(8): 847-53; Elliott et al. 2003; *Nature Biotechnology,* 21: 414-21; Shields et al. 2002 *Journal of Biological Chemistry,* 277(30): 26733-40; all of which are incorporated herein by reference in their entirety.

In some embodiments, the invention encompasses molecules comprising one or more glycosylation sites, so that one or more carbohydrate moieties are covalently attached to the molecule. In other embodiments, the invention encompasses molecules comprising one or more glycosylation sites and one or more modifications in the Fc region, such as those disclosed supra and those disclosed in U.S. Provisional Application Nos. 60/439,498; 60/456,041; and 60/514,549 filed on Jan. 9, 2003; Mar. 19, 2003, and Oct. 23, 2003, and U.S. Application No. 60/514,549 filed on Jan. 9, 2004, all of which are incorporated herein by reference in their entireties. In preferred embodiments, the one or more modifications in the Fc region enhance the affinity of the molecule for an activating FcγR, e.g., FcγRIIIA, relative to the antibody comprising the wild type Fc regions.

The invention encompasses molecules that have been modified by introducing one or more glycosylation sites into one or more sites of the molecules, preferably without altering the functionality of the molecule, e.g., binding activity. As used herein, "glycosylation sites" include any specific amino acid sequence in a molecule of the invention to which an oligosaccharide (i.e., carbohydrates containing two or more simple sugars linked together) will specifically and covalently attach. Oligosaccharide side chains are typically linked to the backbone of an antibody via either N— or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. In some embodiments, the invention encompasses methods of modifying the carbohydrate content of a molecule of the invention by adding or deleting a glycosylation site. Methods for modifying the carbohydrate content of antibodies are well known in the art and encompassed within the invention, see, e.g., U.S. Pat. No. 6,218,149; EP 0 359 096 B1; U.S. Publication No. US 2002/0028486; WO 03/035835; U.S. Publication No. 2003/0115614; U.S. Pat. Nos. 6,218,149; 6,472,511; all of which are incorporated herein by reference in their entirety. In other embodiments, the invention encompasses methods of modifying the carbohydrate content of a molecule of the invention by deleting one or more endogenous carbohydrate moieties of the molecule.

The invention encompasses molecules comprising an Fc region, e.g., derived from human IgG$_1$, where the amino acids corresponding to position 297 of the C$_H$2 domains of the Fc region are aglycosyl. The terms "aglycosyl" or "aglycosylated," when referring to an Fc region in its entirety, or a specific amino acid residue in the Fc region, mean that no carbohydrate residues are attached to the specified region or residue.

Human IgG antibodies that are aglycosylated show decreased binding to Fc effector ligands such as Fc receptors and C1q (see, e.g., Jefferis et al., 1995, *Immunology Letters* 44:111-17; Tao, 1989, *J. of Immunology,* 143:2595-2601; Friend et al., 1999, *Transplantation* 68:1632-37; Radaev and Sun, 2001, *J. of Biological Chemistry* 276:16478-83; Shields et al, 2001, *J. of Biological Chemistry* 276:6591-6604, and U.S. Pat. No. 5,624,821). Without intending to be bound by a particular mechanism, it is believed that the aglycosylation of the amino acid at position 297 of the Fc domains of molecules described herein results in reduced binding to FcγRIIIA and the C1q component of complement. Such aglycosylated antibodies lack effector function.

In human IgG$_1$ constant regions, the residue at position 297 is asparagine. In one embodiment of the present invention, the residue at, or corresponding to, position 297 of the Fc region of the molecule is other than asparagine. Substitution of another amino acid residue in the place of asparagine eliminates the N-glycosylation site at position 297. Substitution of any amino acid residues which will not result in glycosylation upon expression of the molecule in a mammalian cell is appropriate for this embodiment. For instance, in some embodiments of the invention, the amino acid residue at position 297 is glutamine or alanine. In some embodiments, the amino acid residue at position 297 is cysteine, which is optionally linked to PEG.

In other embodiments of the invention, the residue at position 297 may or may not be asparagine, but is not glycosylated. This can be accomplished in a variety of ways. For example, amino acid residues other than the asparagine at position 297 are known to be important for N-linked glycosylation at position 297 (see Jefferis and Lund, 1997, *Chem. Immunol.* 65:111-28), and the substitution of residues at positions other than position 297, of the C$_H$2 domain can result in a molecule aglycosylated at residue 297. Examples of such positions are position 298 and 299.

In some embodiments, the molecules of the invention are substantially free of one or more selected sugar groups, e.g., one or more sialic acid residues, one or more galactose residues, one or more fucose residues. A moleucle that is substantially free of one or more selected sugar groups may be prepared using common methods known to one skilled in the art, including for example recombinantly producing a molecule of the invention in a host cell that is defective in the addition of the selected sugar groups(s) to the carbohydrate moiety of the antibody, such that about 90-100% of the antibody in the composition lacks the selected sugar group(s) attached to the carbohydrate moiety. Alternative methods for preparing such molecules include for example, culturing cells under conditions which prevent or reduce the addition of one or more selected sugar groups, or post-translational removal of one or more selected sugar groups, see, e.g., Shinkawa et al., 2003, J. Biol. Chem. 278(5): 3466-73, which is incorporated herein by reference in its entirety.

5.1.1 Molecules Containing FcγR, Derivatives and Analogs thereof

One aspect of the invention pertains to fusion proteins comprising a polypeptide which specifically binds the Fcγ region of an immunoglobulin that is a derivative or analog of a FcγR, particularly of the extracellular soluble region of an FcγR, covalently linked to a heterologous polypeptide such as, for example, an immunoglobulin constant region. In one embodiment, the invention encompasses an isolated polypeptide comprising an Fcγ binding site, e.g., the extracellular region of an FcγR, or a biologically active fragment thereof which retains Fcγ binding, as determined by standard assays known to those skilled in the art. In one embodiment, the polypeptide comprising an Fcγ binding site can be isolated from cells or tissue sources by an appropriate purification scheme using standard protein purification techniques. In another embodiment, a polypeptide comprising an Fcγ binding site of the invention is produced by recombinant DNA techniques. Alternative to recombinant expression, a polypeptide comprising an Fcγ binding site can be synthesized chemically using standard peptide synthesis techniques.

An "isolated" or "purified" polypeptide or biologically active fragment thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active fragment thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active fragments of a polypeptide of the invention comprising an Fcγ binding site, include polypeptides comprising amino acid sequences sufficiently identical to or derived from the amino acid sequence of the extracellular region of any FcγR including but not limited to FcγRIIIA, FcγRIIIB, FcγRIIA, FcγRIIB (e.g., the amino acid sequences encoded by the cDNA with Genbank Accession No.'s X52645, M31934, M31935, M31933, M31932), which include fewer amino acids than the amino acids of the protein they are derived from, and yet exhibit Fcγ binding activity of the corresponding full-length extracellular region, as determined by standard assays disclosed herein and known to those skilled in the art. A biologically active fragment of a polypeptide of the invention comprising an Fcγ binding site can be a polypeptide which is, for example, at least 25 amino acids or more amino acids in length. The invention encompasses a biologically active fragment of a polypeptide of the invention comprising an amino acid sequence of at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues. Preferably, a biologically active fragment of a polypeptide of the invention comprising an Fcγ binding site is at least 80-100 amino acids in length. In certain embodiments, the invention encompasses the membrane proximal domain of the extracellular region of an FcγR, such as those disclosed in SEQ. ID. NOs. 21-23.

Preferred polypeptides comprising an Fcγ binding site comprise the amino acid sequence of any of SEQ ID NOs. 21-23. Other useful polypeptides encompassed by the invention are substantially identical (e.g., at least about 45%, preferably 55%, 65%, 75%, 85%, 95%, or 99%) to any of the amino acid sequences encoded by the cDNA with Genbank Accession No.'s X52645; M31934, M31935, M31933, and retain the functional activity of the protein of the corresponding naturally-occurring polypeptide, e.g., Fcγ binding, yet differ in amino acid sequence due to natural allelic variation or mutagenesis.

The invention encompsses polypeptides comprising amino acid sequences from any of SEQ ID Nos. 1-4, 33, 35, 37, 39 or 41. In some embodiments, the polypeptides of the invention comprise an amino acid sequence that exhibits at least about 70% sequence identity to any of the SEQ ID Nos mentioned supra, at least 75%, at least about 85%, more preferably at least about 90%, most preferably at least about 90%.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (, % identity=# of identical positions/total # of positions (e.g., overlapping positions)×100). In one embodiment, the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the NBLAST and XBLAST programs of Altschul, et al. (1990) J. Mol. Biol. 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA.

The percent identity between two sequences can be determined using techniques similar to those described above, with or without allowing gaps. In calculating percent identity, typically exact matches are counted.

The present invention also pertains to variants of the polypeptides of the invention comprising an Fcγ binding site which specifically bind an Fcγ region of an immunoglobulin. Variants of a polypeptide of the invention comprising an Fcγ binding site, which retain Fcγ binding, can be identified by screening combinatorial libraries of mutants, e.g., site-directed mutants, random mutants, truncation mutants, of the protein of the invention for Fcγ binding activity. In some embodiments, the variants of a polypeptide of the invention can be screened for enhanced binding to FcγR as described by assays disclosed herein or known to those skilled in the art. The invention also encompasses screening the variants of a polypeptide of the invention comprising the extracellular region of an FcγR comprising an Fcγ binding site fused to an immunoglobulin constant region, for a lower affinity of the immunoglobulin constant region to the FcγR extracellular region. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

In addition, libraries of fragments of the coding sequence of a polypeptide of the invention comprising an Fcγ binding site, can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with SI nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) Proc. Natl. Acad. Sci. USA 89:7811-7815; Delgrave et al. (1993) Protein Engineering 6(3):327-331).

Molecules of the invention, including the fusion proteins as well as the soluble FcγR proteins, may be modified by attaching polymer molecules such as high molecular weight polyethyleneglycol (PEG). In a specific embodiment, molecules of the invention that have been modified with PEG have increased in vivo half lives, e.g., serum half-lives. PEG can be attached to said molecules with or without a multifunctional linker either through site-specific conjugation of the PEG to the N— or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography. Methods for modifying polypeptides with PEG are known to those skilled in the art. See, e.g., Leong et. al., 2001 Cytokine, 16:106-19; Koumenis et al., 2000, Int. J. Pharm, 198: 83,95; U.S. Pat. No. 6,025,158, all of which are incorporated herein by reference in their entirety. Included within the scope of the invention are derivatives or analogs of the molecules of the invention, which are differentially modified during or after translation, e.g., by amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, NaBH₄, or acetylation, formylation, oxidation, or reduction, or metabolic synthesis in the presence of tunicamycin, etc.

In addition, analogs and derivatives of the molecules of the invention can be chemically synthesized. For example, a peptide corresponding to the extracellular region of an FcγR, which mediates the desired functional activity (i. e. Fcγ binding) in vitro, for use in the compositions of the invention can be synthesized by use of a peptide synthesizer. Furthermore, if desired, one or more non-classical amino acids or chemical amino acid analogs can be introduced as a substitution or addition into FcγR sequence. Non-classical amino acids include but are not limited to the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary). A polypeptide of the invention comprising an Fcγ binding site may also be modified post-translationally using any of the methods known to those skilled in the art. Post translational modifications include but are not limited to glycosylations (e.g., N-linked or O-linked glycosylations), myristylations, palmitylations, fucosylation, acetylations, phosphorylations (e.g., serine/threonine or tyrosine).

The methods of the present invention also encompass the use of molecules of the invention that have half-lives (e.g., serum half-lives) in a mammal, preferably a human, of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the molecules of the present invention or biologically active fragments thereof in a mammal, preferably a human, results in a higher serum titer of said molecules in the mammal, and thus, reduces the frequency of the administration of said molecules and/or reduces the concentration of said molecules to be administered. Molecules of the invention having increased in vivo half-lives can be generated by techniques known to those of skill in the art.

The extracellular region of an FcγR is preferably linked to an immunoglobulin constant region. Typically an immunoglobulin constant region comprises at least a functionally operative CH2 and CH3 domain of the constant region of an immunoglobulin heavy chain. The fusion proteins of the invention, may preferably further comprise the hinge region N-terminal to the constant region. In some embodiments, an immunoglobulin constant region for use in the methods and compositions of the invention comprises the hinge-CH1 domain. In other embodiments, an immunoglobulin constant region for use in the methods and compositions of the invention comprises the hinge-CH2 domain (e.g., amino acids 216-340). In yet other embodiments, an immunoglobulin constant region for use in the methods and compositions of the invention comprises hinge-CH3 region (e.g., amino acids 216-230 and amino acids 341-446). In a most preferred embodiment, the immunoglobulin constant region has reduced or no affinity for the extracellular region of an FcγR to which it is fused. The invention encompasses any immunoglobulin isotype including, but not limited to, IgM, IgG, IgD, IgE, and IgA. Additionally subclasses of IgG, IgG-1, -2, -3, -4 and subclasses of IgA, -1 and -2, are encompassed within the invention. The invention encompasses isolated immunoglobulin constant regions, as well as biologically active fragments thereof. A biologically active fragment of an immunoglobulin constant region for use in the methods and compositions of the invention refers to a peptide or polypeptide comprising an amino acid sequence of at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of the Fcγ domain of an antibody, preferably an IgG molecule. Preferably a biologically active fragment of an immunoglobulin constant region comprises an amino acid sequence of at lease 90-100 amino acids. A fragment of an Fcγ domain may comprise the CH2 region, CH3 region, Fcγ hinge region, or a combination thereof.

The present invention also pertains to variants, derivatives, or analogs of an immunoglobulin constant region for use in the methods and compositions of the invention. Variants of an immunoglobulin constant region can be produced using any of the methods disclosed herein or known to those skilled in the art. Modifications of Fcγ regions are well known in the art, whereby one or more amino acid alterations (e.g., substitutions) are introduced in an Fcγ region of an immunoglobulin (See e.g., U.S. Pat. No. 6,194,551, WO 00/42072 which is incorporated herein by reference in its entirety). Variants of an immunoglobulin constant region may also be alternatively produced using any of the methods disclosed in U.S. Provisional Application Nos. 60/439,498; 60/456,041, filed on Jan. 9, 2003, Mar. 19, 2003 and U.S. Provisional Application No. 60/514,549 filed on Oct. 23, 2003, and U.S. application Ser. No. 10/754,922 filed on Jan. 9, 2004, all of which are incorporated herein by reference in their entireties.

Immunoglobulin constant regions for use in the methods and compositions of the invention may be modified using any of the methods described supra, or known to those skilled in the art. In certain embodiments, the immunoglobulin constant regions are modified by attaching polymer molecules such as polyethylene glycol. The invention also encompasses post-translational modifications of the immunoglobulin constant regions. Post translational modifications include but are not limited to glycosylations (e.g., N-linked or O-linked glycosylations), myristylations, palmitylations, acetylations, phosphorylations (e.g., serine/threonine or tyrosine).

Included within the scope of the invention are derivatives or analogs of the immunoglobulin constant regions, which are differentially modified during or after translation, e.g., by amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, NaBH₄, or acetylation, formylation, oxidation, or reduction, or metabolic synthesis in the presence of tunicamycin, etc.

An immunoglobulin constant region for use in the invention includes for example, polypeptides comprising amino acid sequences sufficiently identical to or derived from the amino acid sequence of the constant region encoded by cDNA's corresponding to the following GENBANK accession numbers J00230 V00554 GI: 184750, J00228 GI:184739; J00231 GI:185041; K01316 GI:184751. Alternatively, an immunoglobulin constant region includes fewer amino acids than the full length immunoglobulin constant region. In a preferred embodiment, the immunoglobulin constant region further comprises the hinge region. A biologically active fragment of an immunoglobulin constant region which can be used in accordance with the invention can be a polypeptide which is for example 80-100 amino acids in length which retains binding to FcγR as determined by standard assays known to those skilled in the art.

Preferred immunoglobulin constant regions have the amino acid sequence encoded by cDNA with GENBANK Accession No. JOO230 V00554 GI: 184750. Other useful immunoglobulin constant regions are substantially identical (e.g., at least about 45%, preferably 55%, 65%, 75%, 85%, 95%, or 99%) to any of the sequences encoded by cDNA's corresponding to the following GENBANK accession numbers JOO230 V00554 GI: 184750, J00228 GI: 184739; J00231 GI: 185041; K01316 GI: 184751, and retain binding to an FcγR yet differ in amino acid sequence from the corresponding naturally occurring immunoglobulin constant region due to natural allelic variation or mutagenesis. The determination of percent identity was described above.

The present invention also encompasses variants of an immunoglobulin constant region. Any of the variants identified and disclosed in U.S. Provisional Application Nos. 60/439,498; 60/456,041, filed on Jan. 9, 2003, Mar. 19, 2003 and U.S. Provisional Application No. 60/514,549 filed on Oct. 23, 2003, and U.S. application Ser. No. 10/754,922 filed on Jan. 9, 2004, all of which are incorporated herein by reference in their entireties, is within the scope of the present invention. Additionally, any variant of an immunoglobulin constant region, identified and generated using the methods disclosed in U.S. Provisional Application Nos. 60/439,498; 60/456,041, filed on Jan. 9, 2003, Mar. 19, 2003 and U.S. Provisional Application No. 60/514,549 filed on Oct. 23, 2003, and U.S. application Ser. No. 10/754,922 filed on Jan. 9, 2004, all of which are incorporated herein by reference in their entireties.

The invention encompasses polypeptides comprising an Fcγ binding site that is the extracellular region of an FcγR, having an amino acid sequence that is at least 25%, preferably 30%, 35%, 40%, 45%, 50%, 55%, 65%, 75%, 85%, 95% or 98% identical to the amino acid sequences encoded by any of the cDNA's with Genbank Accession No.'s X52645; M31934, M31935, M31933, M31932, wherein the protein or polypeptides retains Fcγ binding activity.

The invention further encompasses fusion polypeptides comprising the extracellular region of an FcγR fused to an immunoglobulin constant region, such that the immunoglobulin constant region has an amino acid sequence that is at least 25%, preferably 30%, 35%, 40%, 45%, 50%, 55%, 65%, 75%, 85%, 95% or 98% identical to the amino acid sequences encoded by any of the cDNA's corresponding to the following GENBANK accession numbers JOO230 V00554 GI: 184750, J00228 GI: 184739; J00231 GI: 185041; K01316 GI: 184751.

Also within the invention are isolated polypeptides or proteins comprising an Fcγ binding site that is the extracellular region of an FcγR, which are encoded by a nucleic acid molecule having a nucleotide sequence that is at least about 30%, preferably 35%, 40%, 45%, 50%, 55%, 60%, 65%, 75%, 85%, 95% or 98% identical to the nucleic acid sequence of any of the sequences with Genbank Accession No.'s X52645; M31934, M31935, M31933, M31932, and isolated polypeptides or proteins which are encoded by a nucleic acid molecule having a nucleotide sequence which hybridizes under stringent hybridization conditions to a nucleic acid molecule having the nucleotide sequence of, any of the sequences with Genbank Accession No.'s X52645; M31934, M31935, M31933, M31932 or a complement thereof.

Also within the invention are isolated polypeptides or proteins comprising an Fcγ binding site that is the extracellular region of an Fcγ fused to an immunoglobulin constant region, such that the immunoglobulin constant region is encoded by a nucleic acid molecule having a nucleotide sequence that is at least about 30%, preferably 35%, 40%, 45%, 50%, 55%, 60%, 65%, 75%, 85%, 95% or 98% identical to the nucleic acid sequence with GENBANK accession numbers JOO230 V00554 GI: 184750, J00228 GI: 184739; J00231 GI: 185041; K01316 GI: 184751, and isolated polypeptides or proteins which are encoded by a nucleic acid molecule having a nucleotide sequence which hybridizes under stringent hybridization conditions to a nucleic acid molecule having the nucleotide sequence of any of the sequences with GENBANK accession numbers JOO230 V00554 GI: 184750, J00228 GI: 184739; J00231 GI: 185041; K01316 GI: 184751, or a complement thereof.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

5.1.2 Soluble FcγR Conjugates

The polypeptides of the invention, e.g., soluble FcγR proteins, fusion proteins thereof, and analogs thereof may be recombinantly fused or chemically conjugated (including both covalently and non-covalently conjugations) to heterologous polypeptides (i.e., an unrelated polypeptide; or portion thereof, preferably at least 10, at least 20, at least 30, at least 40, at least 50, at least 60, at least 70, at least 80, at least 90 or at least 100 amino acids of the polypeptide) to generate hybrid fusion proteins. The fusion does not necessarily need to be direct, but may occur through linker sequences. In some embodiments, the invention encompasses a dimeric fusion protein of the invention comprising the extracellular region of an FcγR fused to an immunoglobulin constant region, further fused to another heterologous polypeptide, as disclosed herein.

The polypeptides of the invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA, 86:821-824, 1989, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., Cell, 37:767 1984) and the "flag" tag (Knappik et al., Biotechniques, 17(4):754-761, 1994).

The present invention also encompasses polypeptides of the invention conjugated to a diagnostic or therapeutic agent or any other molecule for which serum half-life is desired to be increased. The polypeptides of the invention, e.g., soluble FcγRIIIA, or soluble FcγRIIB, can be used diagnostically to, for example, monitor the development or progression of a disease, disorder or infection as part of a clinical testing procedure to, e.g., determine the efficacy of a given treatment regimen. Activation and inhibitory Fcγ receptors, e.g., FcγRIIIA, and FcγRIIB, are critical for the balanced function of these receptors and proper cellular immune responses. Thus, the polypeptides of the invention fused to a detectable label may be used to monitor the progression of any disease related to loss of the balance of the immune response achieved by the activating and inhibitory receptors. Detection can be facilitated by coupling the antibody to a detectable substance. Examples of detectable substances include various enzymes, prosthetic groups, fluorescent materials, luminescent materials, bioluminescent materials, radioactive materials, positron emitting metals, and nonradioactive paramagnetic metal ions. The detectable substance may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Such diagnosis and detection can be accomplished by coupling the antibody to detectable substances including, but not limited to, various enzymes, enzymes including, but not limited to, horseradish peroxidase, alkaline phosphatase, beta-galactosidase, or acetylcholinesterase; prosthetic group complexes such as, but not limited to, streptavidin/biotin and avidin/biotin; fluorescent materials such as, but not limited to, umbelliferone, fluorescein, fluorescein isothiocyanate, rhodamine, dichlorotriazinylamine fluorescein, dansyl chloride or phycoerythrin; luminescent material such as, but not limited to, luminol; bioluminescent materials such as, but not limited to, luciferase, luciferin, and aequorin; radioactive material such as, but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, 112I, $^{111}$In), iodine ($^{131}$I, $^{125}$I, $^{123}$I, $^{121}$I) lanthaum ($^{140}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{105}$Rh), ruthenium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb), yttrium ($^{90}$Y), zinc ($^{65}$Zn); positron emitting metals using various positron emission tomographies, and nonradioactive paramagnetic metal ions.

A polypeptide of the invention may be conjugated to a therapeutic moiety such as a cytotoxin (e.g., a cytostatic or cytocidal agent), a therapeutic agent or a radioactive element (e.g., alpha-emitters, gamma-emitters, etc.). Cytotoxins or cytotoxic agents include any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Moreover, a polypeptide of the invention can be conjugated to therapeutic moieties such as a radioactive materials or macrocyclic chelators useful for conjugating radiometal ions (see above for examples of radioactive materials). In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4:2483-90; Peterson et al., 1999, Bioconjug. Chem. 10:553; and Zimmerman et al., 1999, Nucl. Med. Biol. 26:943-50 each incorporated by reference in their entireties.

Techniques for conjugating such therapeutic moieties to polypeptides are well known; see, e.g., Arnon et al., "Monoclonal Antibodies For Immunotargeting Of Drugs In Cancer Therapy", in Monoclonal Antibodies And Cancer Therapy, Reisfeld et al. (eds.), 1985, pp. 243-56, Alan R. Liss, Inc.); Hellstrom et al., "Antibodies For Drug Delivery", in Controlled Drug Delivery (2nd Ed.), Robinson et al. (eds.), 1987, pp. 623-53, Marcel Dekker, Inc.); Thorpe, "Antibody Carriers Of Cytotoxic Agents In Cancer Therapy: A Review", in Monoclonal Antibodies '84: Biological And Clinical Applications, Pinchera et al. (eds.), 1985, pp. 475-506); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), 1985, pp. 303-16, Academic Press; and Thorpe et al., Immunol. Rev., 62:119-58, 1982.

5.2 Characterization of Soluble FcγR Proteins

The invention encompasses methods for characterizing soluble FcγR proteins of the invention, fusion proteins comprising same, and derivatives and analogs thereof. The invention encompasses characterizing the molecules of the invention (e.g., soluble FcγR proteins, fusion proteins comprising the extracellular region of FcγR) in cell based and/or cell-free assays. In particular, molecules of the invention comprising the extracellular region of an Fcγ may be assayed for the ability to immunospecifically bind to a ligand, e.g., a molecule comprising an Fcγ region, such as an immune complex. Immunoassays which can be used to analyze immunospecific binding of the molecules of the invention include, but are not limited to, FACS analysis, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well-known in the art (see, e.g., Ausubel et al., eds, 1994, Current Protocols in Molecular Biology, Vol. 1, John Wiley & Sons, Inc., New York, which is incorporated by reference herein in its entirety).

One exemplary assay for determining the binding of the molecules of the invention, e.g., soluble FcγR proteins, fusion proteins comprising soluble FcγR extracellular regions, to an immune complex is an ELISA based assay and comprises the following (this assay is further exemplified in Example 6): forming an immune complex comprising a chimeric 4-4-20 antibody (which is a mouse anti-fluorescein monoclonal antibody) and bovine serum albumin which has been conjugated to FITC; titrating in increasing concentrations of a molecule of the invention; detecting and measuring the binding of a molecule of the invention to the immune complex. As a negative control, increasing concentration of either the native FcγR protein, or a fusion protein comprising the wild-type FcγR extracellular region is also titrated in and allowed to interact with the immune complex, and the binding to the immune complex is detected and measured. The binding of a molecule of the invention to the immune complex is compared to the binding of the negative control to the immune complex, and the molecule of the invention possesses a comparable binding parameter (e.g., Kd; the concentration of the molecule that results in 50% apparent binding) as the negative control. In some embodiments, a molecule of the invention has a higher affinity relative to the negative control as measured in the assay. Other immune complexes can be formed using standard techniques known in the art.

Binding of the molecules of the invention to a ligand, e.g., an immune complex, a molecule comprising an Fcγ region, can also be detected using a surface plasmon based resonance assay, which also provides information on the kinetic and equilibrium properties of the binding partners, i.e., a molecule of the invention and an immune complex.

The molecules of the invention may be assayed using any surface plasmon resonance based assays known in the art for characterizing the kinetic parameters of a molecule of the invention to a ligand, e.g., an immune complex, a molecule comprising an Fcγ region. Any SPR instrument commercially available including, but not limited to, BIAcore Instruments, available from Biacore AB (Uppsala, Sweden); IAsys instruments available from Affinity Sensors (Franklin, Mass.); IBIS system available from Windsor Scientific Limited (Berks, UK), SPR-CELLIA systems available from Nippon Laser and Electronics Lab (Hokkaido, Japan), and SPR Detector Spreeta available from Texas Instruments (Dallas, Tex.) can be used in the instant invention. For a review of SPR-based technology see Mullet et al., 2000, *Methods* 22: 77-91; Dong et al., 2002, *Review in Mol. Biotech.*, 82: 303-23; Fivash et al., 1998, *Current Opinion in Biotechnology* 9: 97-101; Rich et al., 2000, *Current Opinion in Biotechnology* 11: 54-61; all of which are incorporated herein by reference in their entirety. Additionally, any of the SPR instruments and SPR based methods for measuring protein-protein interactions described in U.S. Pat. Nos. 6,373,577; 6,289,286; 5,322,798; 5,341, 215; 6,268,125 are contemplated in the methods of the invention, all of which are incorporated herein by reference in their entirety.

Briefly, SPR based assays involve immobilizing a member of a binding pair on a surface, and monitoring its interaction with the other member of the binding pair in solution in real time. SPR is based on measuring the change in refractive-index of the solvent near the surface that occurs upon complex formation or dissociation. The surface onto which the immobilization occur is the sensor chip, which is at the heart of the SPR technology; it consists of a glass surface coated with a thin layer of gold and forms the basis for a range of specialized surfaces designed to optimize the binding of a molecule to the surface. A variety of sensor chips are commercially available especially from the companies listed supra, all of which may be used in the methods of the invention. Examples of sensor chips include those available from BIAcore AB, Inc., e.g., Sensor Chip CM5, SA, NTA, and HPA. A molecule of the invention may be immobilized onto the surface of a sensor chip using any of the immobilization methods and chemistries known in the art, including but not limited to, direct covalent coupling via amine groups, direct covalent coupling via sulfhydryl groups, biotin attachment to avidin coated surface, aldehyde coupling to carbohydrate groups, and attachment through the histidine tag with NTA chips.

In some embodiments, the kinetic parameters of the binding of molecules of the invention, to an ligand may be determined using a BIAcore instrument (e.g., BIAcore instrument 1000, BIAcore Inc., Piscataway, N.J.).

Once an entire data set is collected, the resulting binding curves are globally fitted using computer algorithms supplied by the SPR instrument manufacturer, e.g., BIAcore, Inc. (Piscataway, N.J.). These algorithms calculate both the $K_{on}$ and $K_{off}$, from which the apparent equilibrium binding constant, $K_d$ is deduced as the ratio of the two rate constants (i.e., $K_{off}/K_{on}$). More detailed treatments of how the individual rate constants are derived can be found in the BIAevaluaion Software Handbook (BIAcore, Inc., Piscataway, N.J.). The analysis of the generated data may be done using any method known in the art. For a review of the various methods of interpretation of the kinetic data generated see Myszka, 1997, *Current Opinion in Biotechnology* 8: 50-7; Fisher et al., 1994, *Current Opinion in Biotechnology* 5: 389-95; O'Shannessy, 1994, *Current Opinion in Biotechnology*, 5:65-71; Chaiken et al., 1992, *Analytical Biochemistry*, 201: 197-210; Morton et al., 1995, *Analytical Biochemistry* 227: 176-85; O'Shannessy et al., 1996, *Analytical Biochemistry* 236: 275-83; all of which are incorporated herein by reference in their entirety.

The invention further encompasses characterizing the molecules of the invention by an immune complex blocking assay, whereby the ability of an FcγRIIIA binding protein, e.g., an antibody that specifically binds FcγRIIIA such as the 3G8 monoclonal antibody to block, i.e., inhibit, the binding of a molecule of the invention to an immune complex is measured (this assay is further exemplified in Example 6). These immune complex blocking assays are known in the art and can be either done in a cell free assay, e.g., an ELISA format assay, or as a cell-based assay using for e.g., radioimmunoassay or FACS analysis.

One exemplary assay for determining the immune complex blocking activity of the molecules of the invention, e.g., soluble FcγR proteins, fusion proteins comprising soluble Fcγ extracellular regions, to an immune complex is an ELISA based assay and comprises the following (this assay is further exemplified in Example 6): forming an immune complex comprising a 4-4-20 antibody (which is a mouse anti-fluorescein monoclonal antibody) and bovine serum albumin which has been conjugated to FITC; pre-incubating serial dilutions of a 3G8 monoclonal antibody with a biotinylated molecule of the invention under conditions to allow the 3G8 monoclonal antibody and the molecule of the invention to interact; titrating in increasing concentrations of the molecule of the invention bound to the 3G8 monoclonal antibody; detecting and measuring the binding of the molecule of the invention-3G8 complex to the immune complex. As a negative control, (1) increasing concentrations of either the native FcγR protein, or a fusion protein comprising the wild-type FcγR extracellular region which has also been pre-incubated with the 3G8 monoclonal antibody is titrated and allowed to interact with the immune complex and the binding is measured; (2) the molecule of the invention is not pre-incubated; or (3) the molecule of the invention is pre-incubated with an irrelevant immunoglobulin that does not have any affinity for FcγRIIIA. The binding of the molecule of the invention-3G8 complex and the binding of any of the negative controls is compared, wherein the ability of 3G8 monoclonal antibody to block immune complex binding to a molecule of the invention is measured as the percent decrease in the detected signal.

Another exemplary assay for measuring the immune complex blocking activity of the molecules of the invention is a cell based using e.g., radioimmunoassay (RIA). Alternatively a FACS based analysis can be used. In this assay the ability of an FcγRIIIA binding protein, e.g., a 3G8 monoclonal antibody, to block the binding of a molecule of the invention to IgG complexes formed on FcγRIIIA bearing cells is measured. Suitable cells that can be used include but are not limited to: (1) NK cells or macrophages derived from normal human peripheral blood lymphocytes; (2) Cells obtained from huCD16A transgenic mice (Li, 1996 J. Exp. Med. 183: 1259-63); (3) mammalian cell lines expressing the extracellular portion of CD16A fused to the transmembrane and intracellular domain of RII or another receptor (such as CD8 or LFA-3); (4) mammalian cell lines (e.g., CHO, HEK-293, COS mouse myeloma cells (NSO)) transfected transiently or stably with CD16A expression vectors (and optionally coexpressing gamma chain for optimal expression receptor expression). In an exemplary RIA cell-based assay, the binding of a molecule of the invention to an immune complex can be measured. A molecule of the invention is $^{125}$I labeled and the specific radioactivity of the molecule can be determined by standard methods known to those skilled in the art. The labeled molecule of the invention and the FcγRIIIA bearing cells, which have been pre-incubated with IgG to form immune complex coated cells, are mixed for several hours; the cells and bound material are separated from the unbound material by centrifugation, and the radioactivity in both compartments is determined. A direct binding format is used to determine the Kd of the molecules of the invention to the FcγRIIIA-IgG coated cells. The number of binding sites for, the iodinated molecule of the invention can be determined using Scatchard analysis of the binding data as determined by one skilled in the art. Controls containing an excess of cold (unlabeled) molecule competitor can be included to ensure the results reflect specific interactions. A competitive format assay RIA-cell based assay can then be used to measure the ability of an FcγRIIIA binding molecules, e.g., a 3G8 monoclonal antibody, to inhibit the binding of a molecules of the invention to the FcγRIIIA-IgG coated cells.

The invention encompasses other assays for measuring the Fcγ binding of the molecules of the invention. In one embodiment, the ability of a molecule of the invention to preferentially remove FcγRIIA from solution by an immunosorbent column comprising human IgG is determined using standard methods known to those skilled in the art. In another embodiment, the invention encompasses measuring rosette formation between IgG coated red blood cells and cells known to have FcγRIIIA. Rosette assays are standard in the art, e.g., Winchester et al., Chapter 31, in Rose et al., eds., Manual of Clinical Laboratory Immunology, 3$^{rd}$ Ed., American Society for Microbiology, Washington DC., 1986; Savelkoul et al., 1988, Journal of Immunological Methods, 111: 31-37; Kofler et al., 1977, Journal of Immunological Methods, 16: 201-209; Lopez et al., 1999, Immunology, 98: 450-455; all of which are incorporated herein by reference in its entirety)

The invention also encompasses determining the ability of the molecules of the invention, particularly molecules comprising the extracellular regions of an FcγRIIB, to modulate the activation of human mast cells, by monitoring the amount of b-hexaminidase released upon degranulation of mast cells. Although not intending to be bound by any particular mode of action the amount of b-hexaminidase released is proportional to the activation of the receptor. Other assays known in the art for measuring the activation of mast cells are also within the scope of the invention, e.g. assays to measure serotonine release, assays to measure histamine release.

The invention also encompasses methods for characterizing the ability of the molecules of the invention to block the effector cell-mediated functions of FcγR. Examples of effector cell functions that can be assayed in accordance with the invention, include but are not limited to, antibody-dependent cell mediated cytotoxicity, phagocytosis, opsonization, opsonophagocytosis, C1q binding, and complement dependent cell mediated cytotoxicity. Any cell-based or cell free assay known to those skilled in the art for determining effector cell function activity can be used (For effector cell assays, see Perussia et al., 2000, Methods Mol. Biol. 121: 179-92; Baggiolini et al., 1998 Experientia, 44(10): 841-8; Lehmann et al., 2000 J. Immunol. Methods, 243(1-2): 229-42; Brown E J. 1994, Methods Cell Biol., 45: 147-64; Munn et al., 1990 J. Exp. Med., 172: 231-237, Abdul-Majid et al., 2002 Scand. J. Immunol. 55: 70-81; Ding et al., 1998, Immunity 8:403-411, each of which is incorporated by reference herein in its entirety).

5.3 Methods of Recombinatly Producing Soluble FcγR Proteins 5.3.1 Polynucleotides Encoding Soluble FcγR Proteins The present invention also encompasses polynucleotides that encode the molecules, including the polypeptides consisting of FcγR extracellular regions, fusion proteins comprising the extracellular regions of FcγR, derivatives and analogs thereof, and any other molecule identified by the methods of the invention. The polynucleotides encoding the molecules of the invention may be obtained, and the nucleotide sequence of the polynucleotides determined, by any method known in the art.

In one embodiment, the invention provides an isolated nucleic acid sequence encoding the extracellular region of FcγRIIIA, preferably human. In another embodiment, the invention provides an isolated nucleic acid sequence encoding the extracellular region of FcγRIIB, preferably human. In one embodiment the invention encompasses an isolated nucleic acid sequence encoding the extracellular region of an FcγR fused to an immunoglobulin constant region, e.g., IgG2 constant region. In a specific preferred embodiment, the invention provides an isolated nucleic acid sequence encoding the extracellular region of FcγIIIA, preferably human, fused to the hinge-constant region of IgG2. In another preferred embodiment, embodiment the invention provides an isolated nucleic acid sequence encoding the extracellular region of FcγRIIB, preferably human, fused to the hinge-constant region of IgG2.

In certain embodiments, the invention encompasses nucleic acid sequences of any of SEQ ID Nos. 5-8. In other embodiments, the invention encompasses nucleic acid sequences comprising a sequence hybridizable to SEQ ID NOs. 1-8, 33, 35, 37, 39 or 41 or its complement under conditions of high stringency. In other embodiments the invention encompasses a nucleic acid sequence at least 70%, 80%, or 90% homologous to SEQ ID NOs. 33, 35, 37, 39 or 41 or its complement as determined using algorithms known to one skilled in the art, such as NBLAST.

One aspect of the invention pertains to isolated nucleic acid molecules that encode a polypeptide of the invention, e.g., a soluble extracellular region of an FcγR, or a fusion protein comprising an extracellular region of an FcγR fused to an immunoglobulin region, such as those disclosed in section 5.1, or a biologically active fragment thereof, as well as nucleic acid molecules sufficient for use as hybridization probes to identify nucleic acid molecules encoding a polypeptide of the invention and fragments of such nucleic acid molecules suitable for use as PCR primers for the amplification or mutation of nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. As used herein, the term "isolated" when referring to a nucleic acid molecule does not include an isolated chromosome.

A nucleic acid molecule of the present invention, e.g., a nucleic acid molecule having the nucleotide sequence of any of the extracellular regions of FcγR, including but not limited to FcγRIIIA, FcγRIIIB, FcγRIIB, FcγRIIA, as well as nucleic acid molecules having the nucleotide sequence of an immunoglobulin constant region, for example, nucleic acid sequence with GENBANK Accession No. J00230 V00554 or a complement thereof, can be isolated using standard molecular biology techniques and the sequence information provided herein. Using all or a portion of the nucleic acid sequences of IgG constant regions, for example a portion of the nucleic acid sequence with GENBANK Accession No. J00230 V00554 as a hybridization probe, nucleic acid molecules of the invention can be isolated using standard hybridization and cloning techniques (e.g., as described in Sambrook et al., eds., Molecular Cloning: A Laboratory Manual, 2nd ed., Cold Spring Harbor Laboratory, Cold Spring Harbor Laboratory Press, Cold Spring Harbor, N.Y., 1989).

A nucleic acid molecule of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

The invention further encompasses nucleic acid molecules that differ from the nucleotide sequence of known FcγR's (e.g., nucleic acid sequences with GENBANK Accession No.'s X52645, M31932, M31934, M31935) and known immunoglobulin constant regions (e.g., nucleic acid sequences with GENBANK accession No.'s JOO230 V00554, J00228 GI: 184739; J00231 GI: 185041; K01316 GI: 184751) due to degeneracy of the genetic code and thus encode the same protein as that encoded by the nucleic acid sequence with GENBANK Accession No.'s X52645, M31932, M31934, M31935, or GENBANK accession No.'s JOO230 V00554, J00228 GI: 184739; J00231 GI: 185041; K01316 GI: 184751.

Moreover, nucleic acid molecules encoding proteins of the invention from other species (homologues) other than human, which have a nucleotide sequence which differs from that of the human protein described herein are intended to be within the scope of the invention. Nucleic acid molecules corresponding to natural allelic variants and homologues of the FcγR sequences and IgG sequences used in the molecules of the invention can be isolated based on their identity to the human nucleic acid molecule disclosed herein using the human sequences, or a portion thereof, as a hybridization probe according to standard hybridization techniques under stringent hybridization conditions.

In addition to naturally-occurring allelic variants of a nucleic acid molecule of the invention sequence that may exist in the population, the skilled artisan will further appreciate that changes can be introduced by mutation thereby leading to changes in the amino acid sequence of the encoded protein, without altering the biological activity of the protein. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologues of various species may be non-essential for activity and thus would be likely targets for alteration. Alternatively, amino acid residues that are conserved among the homologues of various species (e.g., mouse and human) may be essential for activity and thus would not be likely targets for alteration.

An isolated nucleic acid molecule encoding a variant protein can be created by introducing one or more nucleotide substitutions, additions or deletions into the nucleotide sequence of nucleic acid sequences with GENBANK Accession No.'s X52645, M31932, M31934, M31935, JOO230 V00554, J00228 GI: 184739; J00231 GI: 185041; K01316 GI: 184751 such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

Once the nucleotide sequence of the molecules of the invention or other molecules that are identified by the methods of the invention is determined, the nucleotide sequence may be manipulated using methods well known in the art, e.g., recombinant DNA techniques, site directed mutagenesis, PCR, etc. (see, for example, the techniques described in Sambrook et al., 2001, Molecular Cloning, A Laboratory Manual, 3rd Ed., Cold Spring Harbor Laboratory, Cold Spring Harbor, N.Y.; and Ausubel et al., eds., 1998, Current Protocols in Molecular Biology, John Wiley & Sons, NY, which are both incorporated by reference herein in their entireties), to generate, for example, molecules having a different amino acid sequence, for example by generating amino acid substitutions, deletions, and/or insertions.

In another embodiment, human libraries or any other libraries available in the art, can be screened by standard techniques known in the art, to clone the nucleic acids encoding the molecules of the invention.

As discussed in Section 5.1 above, molecules of the invention comprising an extracellular region of FcγR may be engineered using methods known to those skilled in the art. An exemplary method for introducing the mutation is using a commercially available kit, Stratagene's Quick change kit, as exemplified in Example 6. Briefly, this mutagenesis approach takes advantage of the selectivity of the DpnI endonuclease for methylated DNA. The product of a mutagenesis reaction (e.g., PCR based mutagenesis) is digested with DpnI, which digests only methylated DNA. Thus the parental, non-mutated methylated DNA will be cut, leaving the newly synthesized non-methylated product containing the mutation of interest as the predominant species. It will be appreciated by one of skill in the art that amino acid sequence variants of the molecules of the invention may be obtained by any mutagenesis technique known to those skilled in the art. Some of these techniques are briefly described herein, however, it will be recognized that alternative procedures may produce an equivalent result. In a preferred embodiment molecules of the invention comprising variant extracellular regions of FcγR are prepared by error-prone PCR (See Leung et al., 1989, Technique, 1:11).

Mutagenesis may be performed in accordance with any of the techniques known in the art including, but not limited to, synthesizing an oligonucleotide having one or more modifications within the sequence of the extracellular region of FcγR, e.g., FcγRIIIA, to be modified. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered. A number of such primers introducing a variety of different mutations at one or more positions may be used to generated a library of mutants.

The technique of site-specific mutagenesis is well known in the art, as exemplified by various publications (see, e.g., Kunkel et al., Methods Enzymol., 154:367-82, 1987, which is hereby incorporated by reference in its entirety). In general, site-directed mutagenesis is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as T7 DNA polymerase, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as E. coli cells, and clones are selected which include recombinant vectors bearing the mutated sequence arrangement. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

Alternatively, the use of PCR with commercially available thermostable enzymes such as Taq DNA polymerase may be used to incorporate a mutagenic oligonucleotide primer into an amplified DNA fragment that can then be cloned into an appropriate cloning or expression vector. See, e.g., Tomic et al., Nucleic Acids Res., 18(6):1656, 1987, and Upender et al., Biotechniques, 18(l):29-30, 32, 1995, for PCR™-mediated mutagenesis procedures, which are hereby incorporated in their entireties. PCR™ employing a thermostable ligase in addition to a thermostable polymerase may also be used to incorporate a phosphorylated mutagenic oligonucleotide into an amplified DNA fragment that may then be cloned into an appropriate cloning or expression vector (see e.g., Michael, Biotechniques, 16(3):410-2, 1994, which is hereby incorporated by reference in its entirety)

Another method for preparing variants for use in the invention, is cassette mutagenesis based on the technique described by Wells et al. (1985, Gene, 34: 315). The starting material is the plasmid comprising the desired DNA encoding the protein to be mutated (e.g., the DNA encoding a polypeptide comprising an Fcγ region). The codon(s) in the DNA sequence to be mutated are identified; there must be a unique restriction endonuclease site on each side of the identified mutations site(s). If no such restriction site exits, it may be generated by oligonucleotide directed mutagenesis. After the restriction sites have been introduced into the plasmid, the plasmid is cut at these sites and linearized. A double-stranded oligonucleotide encoding the sequence of the DNA between the restriction sites but containing the mutation is synthesized using standard procedures known to those skilled in the art. The double stranded oligonucleotide is referred to as the cassette. This cassette is designed to have 3' and 5' ends that are compatible with the ends of the linearized plasmid, such that it can be directly ligated to the plasmid.

Other methods known to those of skill in the art for producing sequence variants of the molecules of the invention can be used. For example, recombinant vectors encoding the amino acid sequence of a molecule of the invention may be treated with mutagenic agents, such as hydroxylamine, to obtain sequence variants.

Any of a variety of sequencing reactions known in the art can be used to directly sequence the molecules of the invention comprising variant regions, e.g., variant extracellular regions. Examples of sequencing reactions include those based on techniques developed by Maxim and Gilbert (Proc. Natl. Acad. Sci. USA, 74:560, 1977) or Sanger (Proc. Natl. Acad. Sci. USA, 74:5463, 1977). It is also contemplated that any of a variety of automated sequencing procedures can be utilized (Bio/Techniques, 19:448, 1995), including sequencing by mass spectrometry (see, e.g., PCT Publication No. WO 94/16101, Cohen et al., Adv. Chromatogr., 36:127-162, 1996, and Griffin et al., Appl. Biochem. Biotechnol., 38:147-159, 1993).

5.3.2 Recombinant Expression of Soluble FcγR Proteins

Once a nucleic acid sequence encoding a molecule of the invention (e.g., a fusion protein comprising the extracellular region of FcγRIIIA) has been obtained, the vector for the production of the molecule may be produced by recombinant DNA technology using techniques well known in the art.

Methods which are well known to those skilled in the art can be used to construct expression vectors containing the coding sequences for the molecules of the invention and appropriate transcriptional and translational control signals. These methods include, for example, in vitro recombinant DNA techniques, synthetic techniques, and in vivo genetic recombination. (See, for example, the techniques described in Sambrook et al., 1990, Molecular Cloning, A Laboratory Manual, 2d Ed., Cold Spring Harbor Laboratory, Cold Spring Harbor, N.Y. and Ausubel et al. eds., 1998, Current Protocols in Molecular Biology, John Wiley & Sons, NY).

The invention includes recombinantly engineered nucleic acid molecules including molecules in which a coding region for a molecule of the invention is operably linked to a heterologous promoter. The invention includes recombinantly engineered nucleic acid molecules that have been generated in vitro or in vivo using methods known to the skilled artisan. For example, the invention includes nucleic acid molecules present in a cell, e.g., episomal or integrated into one or more chromosomes of a cell. In some embodiments, such nucleic acid molecules are generated in vitro and transfected into a cell. In other embodiments, the nucleic acid molecules of the invention are generated by gene activation technologies known in the art, for example, by introducing at least a heterologous promoter operably linked to an endogenous coding region.

An expression vector comprising the nucleotide sequence of a molecule of the invention or any other molecule identified by the methods of the invention can be transferred to a host cell by conventional techniques (e.g., electroporation, liposomal transfection, and calcium phosphate precipitation) and the transfected cells are then cultured by conventional techniques to produce the molecules of the invention. In specific embodiments, the expression of the molecules of the invention is regulated by a constitutive, an inducible or a tissue, specific promoter.

The host cells used to express the molecules of the invention and other molecules identified by the methods of the invention may be either bacterial cells such as *Escherichia coli*, or, preferably, eukaryotic cells, especially for the expression of whole recombinant immunoglobulin molecule. In particular, mammalian cells such as Chinese hamster ovary cells (CHO), in conjunction with a vector such as the major intermediate early gene promoter element from human cytomegalovirus is an effective expression system for immunoglobulins (Foecking et al., 1998, Gene 45:101; Cockett et al., 1990, Bio/Technology 8:2). Other cells for use in the methods of the invention include, for example, NSO (mouse myeloma cells) and Per.C6 cells (human retinal cells).

A variety of host-expression vector systems may be utilized to express the molecules of the invention. Such host-expression systems represent vehicles by which the coding sequences of the molecules of the invention may be produced and subsequently purified, but also represent cells which may, when transformed or transfected with the appropriate nucleotide coding sequences, express the molecules of the invention in situ. These include, but are not limited to, microorganisms such as bacteria (e.g., *E. coli* and *B. subtilis*) transformed with recombinant bacteriophage DNA, plasmid DNA or cosmid DNA expression vectors containing coding sequences for the molecules; yeast (e.g., *Saccharomyces Pichia*) transformed with recombinant yeast expression vectors containing sequences encoding the molecules of the invention; insect cell systems infected with recombinant virus expression vectors (e.g., baculovirus) containing sequences encoding the molecules of the invention; plant cell systems infected with recombinant virus expression vectors (e.g., cauliflower mosaic virus (CaMV) and tobacco mosaic virus (TMV) or transformed with recombinant plasmid expression vectors (e.g., Ti plasmid) containing sequences encoding the molecules of the invention; or mammalian cell systems (e.g., COS, CHO, BHK, 293, 293T, 3T3 cells, lymphotic cells (see U.S. Pat. No. 5,807,715), Per C.6 cells (human retinal cells developed by Crucell) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the molecule being expressed. For example, when a large quantity of such a protein is to be produced, for the generation of pharmaceutical compositions of a molecule of the invention, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free gluta-thione. The pGEX vectors are designed to include thrombin or factor Xa protease cleavage sites so that the cloned target gene product can be released from the GST moiety. Other preferred vectors for use in the methods of the present invention are those disclosed in U.S. Provisional Application Nos. 60/439,498; 60/456,041; and 60/514,549 filed on Jan. 9, 2003; Mar. 19, 2003, and Oct. 23, 2003, respectively, U.S. application Ser. No. 10/754,922 filed on Jan. 9, 2004, which are incorporated herein by reference in their entireties.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the immunoglobulin molecule in infected hosts (e.g., see Logan & Shenk, 1984, Proc. Natl. Acad. Sci. USA 81:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 293T, 3T3, WI38, BT483, Hs578T, HTB2, BT20 and T47D, CRL7030 and Hs578Bst, NSO, Per.C6.

For long-term, high-yield production of recombinant proteins, stable expression is preferred. For example, cell lines which stably express a molecule of the invention may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibodies of the invention. Such engineered cell lines may be particularly useful in screening and evaluation of compounds that interact directly or indirectly with the antibodies of the invention.

A number of selection systems may be used, including but not limited to the herpes simplex virus thymidine kinase (Wigler et al., 1977, Cell 11: 223), hypoxanthine-guanine phosphoribosyltransferase (Szybalska & Szybalski, 1992, Proc. Natl. Acad. Sci. USA 48: 202), and adenine phosphoribosyltransferase (Lowy et al., 1980, *Cell* 22: 817) genes can be employed in tk-, hgprt- or aprt-cells, respectively. Also, antimetabolite resistance can be used as the basis of selection for the following genes: dhfr, which confers resistance to methotrexate (Wigler et al., 1980, *Proc. Natl. Acad. Sci. USA* 77:357; O'Hare et al., 1981, Proc. Natl. Acad. Sci. USA 78: 1527); gpt, which confers resistance to mycophenolic acid (Mulligan & Berg, 1981, *Proc. Natl. Acad. Sci. USA* 78: 2072); neo, which confers resistance to the aminoglycoside G-418 *Clinical Pharmacy* 12: 488-505; Wu and Wu, 1991, 3:87-95; Tolstoshev, 1993, *Ann. Rev. Pharmacol. Toxicol.* 32:573-596; Mulligan, 1993, *Science* 260:926-932; and Morgan and Anderson, 1993, *Ann. Rev. Biochem.* 62:191-217; May, 1993, TIB TECH 11(5):155-215). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al., 1981, J. Mol. Biol. 150:1; and hygro, which confers resistance to hygromycin (Santerre et al., 1984, Gene 30:147).

The expression levels of a molecule of the invention can be increased by vector amplification (for a review, see Bebbington and Hentschel, The use of vectors based on gene amplification for the expression of cloned genes in mammalian cells in DNA cloning, Vol. 3 (Academic Press, New York, 1987). When a marker in the vector system expressing a molecule of the invnetion is amplifiable, increase in the level of inhibitor present in culture of host cell will increase the number of copies of the marker gene. Since the amplified region is associated with the nucleotide sequence of the molecule, production of the molecules will also increase (Crouse et al., 1983, Mol. Cell. Biol. 3:257).

Once a molecule of the invention has been recombinantly expressed, it may be purified by any method known in the art for purification of polypeptides for example, by chromatography (e.g., ion exchange, affinity, particularly by affinity for the specific antigen after Protein A, and sizing column chromatography), centrifugation, differential solubility, or by any other standard technique for the purification of polypeptides.

The invention encompasses an isolated polypeptide comprising an amino acid sequence selected from any of SEQ ID Nos. 1-4, 33, 35, 37, 39 and 41. In some embodiments, position 418 in SEQ ID No. is a serine. In other embodiments, position 418 is a proline. In some embodiments, position 407 in SEQ ID No. 2 is a serine or proline. In a specific embodiment, position of 410 SEQ ID No. 3 is a seine or a proline and the first N-terminal three amino acids are either Thr-Pro-Ala or are absent. In another specific embodiment, position 410 in SEQ ID NO. 4 is a serine or a proline and the first three N-terminal amino acids are either Thr-Pro-Ala or are absent.

5.4 Prophylatic and Therapeutic Methods

The present invention encompasses treating, preventing, managing, or ameliorating one or more symptoms of an autoimmune disorder or an inflammatory disorder, by administering a molecule of the invention to an animal, preferably a mammal, and most preferably a human. Therapeutic and prophylactic compounds of the invention include, but are not limited to, soluble FcγR polypeptides, fusion polypeptides comprising the extracellular region of FcγR, e.g., FcγRIIIA, FcγRIIB, analogs, derivatives of these molecules and nucleic acids encoding same. Molecules of the invention may be provided in pharmaceutically acceptable compositions as known in the art or as described herein.

5.4.1 Autoimmune Disorders and Inflammatory Disorders

The invention encompasses treating and/or preventing an autoimmune disorder or an inflammatory disorder using the molecules and compositions of the invention. Although not intending to be bound by any mechanism of action, the pathogenic IgG antibodies observed in autoimmune disorders are the pathogenic triggers of the disease and/or contribute to disease progression by the inappropriate activation of FcγR receptors. The aggregated autoantibodies and/or autoantibodies complexed with self antigens (immune complexes) bind to activating FcγR and trigger the pathogenic manifestations of an autoimmune disorder. Although not intending to be limited by any particular mechanism, the molecules of the invention described herein have therapeutic utility for an autoimmune disorder since they interfere with the interaction of autoantibodies and FcγR receptors.

The invention also encompasses treatment and/or prevention of diseases susceptible to treatment with intravenous immunoglobulin therapy, including but not limited to allergic asthma, rheumatoid arthritis, systemic lupus erythrematosus, autoimmune hemolytic anemia (AHA), idiopathic thrombocytopenic purpura (ITP), scleroderma, autoantibody triggered urticaria, pemphigus, vasculitis syndromes, autoimmune cytopenias, Guillain-Barre syndrome, anti-Factor VIII autoimmune disease, uveitis, dermatomyositis.

The invention encompasses the use of the soluble FcγR polypeptides, fusion proteins comprising same, and derivatives thereof as single therapeutic agents or in combination with other therapeutic agents for the treatment and/or prevention of an autoimmune disease or an inflammatory disease. The invention encompasses administering a molecule of the invention, including but not limited to soluble FcγR polypeptides, fusion polypeptides comprising the extraceullular region of FcγR, and analogs and derivatives thereof, to a subject in a therapeutically or prophylcatically effective dose for the treatment or prevention of an autoimmune disease or an inflammatory disease. In one embodiment, a subject is administered one or more doses of a molecule of the invention at a dose of at least 0.1 μg/g, at least 0.2 μg/g, at least 0.3 μg/g, at least 0.4 μg/g, at least 0.5 μg/g, at least 1 μg/g, or at least 5 μg/g.

In a specific embodiment, the invention encompasses a method for treating, preventing or ameliorating one or more symptoms of an autoimmune disease or an inflammatory disease, comprising administering a therapeutically or prophylactically effective amount of a fusion protein comprising the extracellular region of an FcgR joined to an IgG2 hinge constant region. In one embodiment, a subject is administered one or more doses of a fusion protein of the invention at a dose of of at least 0.1 μg/g, at least 0.2 μg/g, at least 0.3 μg/g, at least 0.4 μg/g, at least 0.5 μg/g, at least 1 μg/g, or at least 5 μg/g.

The present invention provides methods of preventing, treating, or managing one or more symptoms associated with an autoimmune or inflammatory disorder in a subject, comprising administering to said subject a therapeutically effective amount of a molecule of the invention. The invention also provides methods for preventing, treating, or managing one or more symptoms associated with an inflammatory disorder in a subject further comprising, administering to said subject a therapeutically effective amount of one or more anti-inflammatory agents. The invention also provides methods for preventing, treating, or managing one or more symptoms associated with an autoimmune disease further comprising, administering to said subject a therapeutically effective amount of one or more immunomodulatory agents. Section 5.4.3 provides non-limiting examples of anti-inflammatory agents and immunomodulatory agents.

The molecules of the invention can also be used in combination with any of the therapeutic agents including antibodies known in the art for the treatment and/or prevention of autoimmune disease or inflammatory disease. A non-limiting example of the therapeutic agents that are used for the treatment or prevention of inflammatory disorders and/or autoimmune disorders are 5G1.1 (Alexion Pharm Inc.), 5G1.1-SC, ABX-CBL (Abgenix Inc.), ABX-IL8 (Abgenics Inc.), Antegren (Athena, Elan), Anti-CD11a (Genentech), Anti-CD18 (Genentech Inc.), Anti-LFAI (Pasteur-Merieux, Immunotech), Antora (Biogen), BTI-322 (Medimmune), CDP571 (Celltech), CDP850 (Celltech), Correvin M (Centocor), D2E7 (CAT/BASF), Hu23F2G (ICOS Pharm Inc.) IC14 (ICOS Pharm Inc.), ICM3 (ICOS Pharm, Inc.), IDEC-114 (IDEC); IDEC131, IDEC-151, IDE-152, Infliximab (Centocor), LDP-01 (Millennium), LDP-02 (Millennium), MDX-33 (Medarex), MDX-CD4, MEDI-507 (Medimmune), OKT4A (Ortho Biotech), rhuMab-E25 (Genentech), SB-240563 (GlaxoSmithKline), 5B-240683, SCH55700 (CellTech, Schering), SMART A-CD3 (Protein Design Lab), Zenapax (Protein Design Lab/Hoffinan LaRoche), ABX-RB2, 5c8 (anti CD-40), SMART Anti-gamma interferon antibody, Verteportin, Enbrel, anti-CD20 antibodies, e.g., Rituximab (McClaughlin et al., 1998, *J Clin. Oncol.* 16(8): 2825-33), Adalimumab (Humira®, Abbott Laboratories), Alefacept (Amevive®, Biogen Inc.), Alemtuzumab (Campath®, ILEX Pharmaceuticals L.P.), Basiliximab (Simulect®, Novartix Pharmaceuticals Corp.), Abciximab (Reopro®, Centocor B.V), Daclizumab (Zenapax®, Hoffmnan-LaRoche Inc.), Etanercept (Enbrel®, Immunex Corp.), Ibritumab tiuxetan (Zevalin®, IDEC Pharmaceutical Corp), Infliximab (Remicade®, Centocor, Inc.), Interferon beta-1a (Avonex®, Biogen, Inc.), Interferon beta-1a (Rebif®, Serono, Inc.), Interferon beta-1b (Betaseron®, Chiron Corp.), Muromonab-CD3 (Orthoclone OKT3®, Ortho Biotech Products LP), Omalizumab (Xolair®, Genentech, Inc.), Rituximab (Rituxan, Genentech Inc.), Tositumomab and Iodine I 131 Tositumomab (Bexxar®, Corixa Corp.), and Pavlizumab (Synagis®, MedImmune Inc.). The molecules of the invention can for example, enhance the efficacy of treatment of the therapeutic antibodies listed above.

Examples of autoimmune disorders that may be treated by administering the molecules of the present invention include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), systemic vasculitis, IgA neuropathy, juvenile arthritis, lichen planus, lupus erthematosus, Ménière's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, and chronic inflammation resulting from chronic viral or bacteria infections. As described herein, some autoimmune disorders are associated with an inflammatory condition. Thus, there is overlap between what is considered an autoimmune disorder and an inflammatory disorder. Therefore, some autoimmune disorders may also be characterized as inflammatory disorders. Examples of inflammatory disorders which can be prevented, treated or managed in accordance with the methods of the invention include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, and chronic inflammation resulting from chronic viral or bacteria infections.

Molecules of the invention can also be used to reduce the inflammation experienced by animals, particularly mammals, with inflammatory disorders. In a specific embodiment, a molecule of the invention reduces the inflammation in an animal by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the inflammation in an animal which is the not administered said molecule. Molecules of the invention can also be used to prevent the rejection of transplants.

5.4.1.1 Idiopathic Thrombocytopenic Purpura

The methods and compositions of the invention are particularly useful for treating, preventing, or ameliorating one or more symptoms of idiopathic thrombocytopenic purpura (ITP), a platelet disorder, in which the subject's immune system attacks and destroys platelets. The platelet count in a subject with ITP is characteristically less than 50,000/mm$^3$. Standard ITP therapy includes for example, intravenous immunoglobulin therapy (IVIG), anti-D (anti-rhesus globulin) therapy which is typically via injection, corticosteroid therapy, splenectomy, steroid therapy, administration of immunosuppressive agents (e.g., steroids, azathioprine, cyclosporin), or plasmaphereis.

The invention encompasses administering a molecule of the invention, including but not limited to soluble FcγR polypeptides, fusion polypeptides comprising the extraceullular region of FcγR, and analogs and derivatives thereof, to a subject in a therapeutically or prophylcatically effective dose for the treatment or prevention of ITP. In one embodiment, a subject is administered one or more doses of a molecule of the invention at a dose of at least 0.1 µg/g, at least 0.2 µg/g, at least 0.3 µg/g, at least 0.4 µg/g, at least 0.5 µg/g, at least 1 µg/g, or at least 5 µg/g.

In a specific embodiment, the invention encompasses a method for treating, preventing or ameliorating one or more symptoms-of ITP, comprising administering a therapeutically or prophylactically effective amount of a fusion protein comprising the extracellular region of an FcgR joined to an IgG2 hinge constant region. In one embodiment, a subject is administered one or more doses of a fusion protein of the invention at a dose of at least 0.1 µg/g, at least 0.2 µg/g, at least 0.3 µg/g, at least 0.4 µg/g, at least 0.5 µg/g, at least 1 µg/g, or at least 5 µg/g.

In one embodiment, the methods and compositions of the invention provide better therapeutic profiles than standard ITP therapy, e.g., IVIG therapy. The invention also encompasses methods for treating, preventing or ameliorating one or more symptoms of ITP, by administering a molecule of the invention in combination with a standard ITP therapy, e.g., IVIG. The protocols for standard ITP therapy are known to those skilled in the art and are contemplated in combination with the methods and compositions of the present invention. For standard ITP therapy regimens, see e.g., Soubrane et al, 1993, Blood, 81(1): 15-19; Clarkson et al., 1986, New England Journal of Med., 314: 1236-1239; Olsson et al., 2002, Thrombosis Research, 107: 135-9; Bussel et al., 1983 Blood, 62: 480-6; Imbach et al., 1981, Lancet, 1: 1228-31; all of which are incorporated herein by reference in their entireties. In another embodiment, the invention further comprises administering a molecule which specifically binds FcγRIIIA, e.g., a 3G8 monoclonal antibody. The methods and compositions of the invention are useful particularly in a subject refractory to standard ITP therapy.

In a specific embodiment, the methods and compositions of the invention enhance the rate of clearance of autologous, osponized red cells in a subject with ITP, as determined by standard assays known to those skilled in the art. An exemplary assay for determining the rate of clearance of opsonized red cells has been established for example by Frank et al. (1979, New England Journal of Med, 300: 518-23; all of which is incorporated herein by reference in its entirety). Briefly, blood is drawn from the subject; the cells are sedimented at 2000 rpm, for five minutes at 4° C.; the erythrocytes are washed in saline buffer; ten micorcuries of $^{51}$Cr is added for each mL of erythrocytes and incubated for 30 minutes at 37° C.; an aliquot of cells is hen sensitized with addition of IgG anti-Rh(D); these IgG sensitized-$^{51}$C labeled erythrocytes are injected through an antecubital vein; and erythrocyte survival is determined by time serial bleeding. Survival is calculated by determining the half life of the cells; the time in which 50% of the cells are removed by circulation.

The methods and compositions of the invention are particularly useful in a subject with a platelet count of at least 5000/mm$^3$, 10,000/mm$^3$, 15,000/mm$^3$, 20,000/mm$^3$, as determined by standard assays known to those skilled in the art. In a specific embodiment, the compositions and methods of the invention, lead to a rise in platelet count to at least 50,000/mm$^3$, at least 100,000/mm$^3$, at least 200,000/mm$^3$, at least 400,000/mm$^3$. In a specific embodiment, the platelet count in the patient rises within 5 days, 6 days, 7 days, 8, days, 9 days, 10 days. In yet another specific embodiment, the platelet count in the patient is maintained for at least 5 days, 6 days, 7 days, 8, days, 9 days, 10 days, 30 days, 1 year, 2 years.

In one embodiment, the methods and compositions of the invention are used in an immunocompromised patient, e.g., a cancer patient or an AIDS patient, susceptible to ITP.

In one embodiment, the compositions of the invention as single therapeutic agents have enhanced therapeutic efficacy in a subject with ITP, relative to standard ITP therapy.

The methods and compositions of the invention preferably do not result in any of the undesirable side effects typically associated with standard IVIG therapy. Undesirable side effects associated with standard IVIG therapy, include for example, HAMA response, neutropenia, cytokine release syndrome.

The invention further encompasses treating and/or preventing ITP using a molecule of the invention in combination with any of the antibodies disclosed by Song et al., Blood 2002 Dec. 27; electronic publication ahead of print, which is disclosed herein by reference in its entirety, e.g., anti-CD24 antibodies; antibodies reactive with other circulating cell types. In preferred embodiments, the molecules of the invention in combination with an antibody disclosed in Song et al., have an enhanced therapeutic efficacy in preventing ITP than the therapeutic efficacy achieved with the antibodies alone. In preferred embodiments, the molecules of the invention in combination with an antibody disclosed in Song et al., significantly prevent thrombocytopenia up to 2-log fold, or 3-log fold lower does as compared to standard IVIG treatment (2 g/Kg).

In some embodiments, the invention encompasses treating and/or preventing ITP using a molecule of the invention in combination with an anti-D antibody or WinRho SDF (Nabi Biopharmaceuticals, Boca Rotan, Fla.). Anti-D antibody is a blood product used to achieve a temporary and occasionally long-term elevation of the platelet counts. It is a sterile freeze dried gamma globulin fraction containing antibodies to Rh (D). Within a few minutes of an intravenous infuision, WinRho SDF coats the recipient's (normal) red cells with purified IgG, which resembles the coating of platelets by the (abnormal autoimmune) ITP immunoglobulin. After D(Rh)-positive red cells are coated with anti-D, they compete with the recipient's IgG(ITP)-coated platelets for phagocytosis (destruction) by macrophages in the spleen. Usually, IgG(WinRho)-coated red cells succeed in blocking the spleen's destruction of IgG(ITP)-coated platelets, thus increasing platelet counts. Significant increases in platelet counts occur within 1-3 days with peak counts observed 8 days after infusion. The effects last approximately one month (See, e.g., George, 2002, *Blood Rev.* 16(1): 37-8; Freiberg et al., 1998, *Semin. Hematol.* 35 (1 Suppl. 1): 23-7; both of which are incorporated herein by reference in their entireties).

The combination treatments of the instant invention comprising administering a therpeutically effective molecule of the invention in combination with WinRho, however provides a more effective therapeutic profile than the use of WinRho alone. Combination treatments of the invention do not result in any of the adverse side effects observed with the use of WinRho alone including but not limited to headaches, chills, fever, body aches, pain and swelling at the injection site, a risk of anaphylaxis (shock response) for patients with hypersensitivity to blood products, and anemia caused by hemolysis (destruction of red blood cells).

5.4.2 Combination Therapy

In certain preferred embodiments, the therapeutic methods of the invention comprises delivering a molecule of the invention in combination with a standard therapy for an autoimmune disease or an inflammatory disorder, e.g., by administering one more additional therapeutic agents disclosed in section 5.4.3 for the treatment and/or prevention of an autoimmune disease or an inflammatory disorder.

The present invention encompasses methods for treating, preventing, or managing an automimmune disorder or an inflammatory disorder in a subject comprising administering a molecule of the invention in combination with one or more other therapeutic agents useful in the treatment, prevention or management of an automimmune disorder or an inflammatory disorder. In some embodiments, the invention encompasses administering a molecule of the invention including but not limited to soluble FcγR polypeptides, fusion polypeptides comprising the extraceullular region of FcγR, and analogs and derivatives thereof in combination with other therapeutic antibodies as disclosed herein. In some embodiments, the invention encompasses adminsitering a soluble FcγR polypeptide of the invention in combination with an antibody specific for FcγRIIIA, or FcγRIIA. Preferably, the anti-FcγRIIIA, and anti-FcγRIIA antibodies used in the methods of the invention are human or humanized. A number of monoclonal antibodies specific for human FcγRIIIA and FcγRIIA are known in the art and disclosed herein and encompassed within the methods and compositions of the invention. Examples of anti FcγR antibodies that may be used in the methods of the invention include KB61 (Schlossman et al., Leucocyte Typing V. Oxford: Oxford University Press, 1985), AT10 (Schlossman et al., Leucocyte Typing V. Oxford: Oxford University Press, 1985), KU79 (Schlossman et al., Leucocyte Typing V. Oxford: Oxford University Press, 1985), FL18.2 (Schlossman et al., Leucocyte Typing V. Oxford: Oxford University Press, 1985), FL18.26 (Schlossman et al., Leucocyte Typing V. Oxford: Oxford University Press, 1985), 2E1 (Knapp et al., Leucocyte Typing IV. Oxford: Oxford University Press, 1989), 41H16 2E1 (Knapp et al., Leucocyte Typing IV. Oxford: Oxford University Press, 1989), K22-2G8 (McInns et al., 1997, Leucocyte Typing, New York: Garland Publishing: 491-4), Il1A5 (Weinrich et al,. 1996, Hybridoma, 15(2): 109-16), Il8D2 (Weinrich et al,. 1996, Hybridoma, 15(2): 109-16), IV.3 (Knapp et al., Leucocyte Typing IV. Oxford: Oxford University Press, 1989), CIKM3 (Knapp et al., Leucocyte Typing IV. Oxford: Oxford University Press, 1989) and CIKM5 (Schlossman et al., Leucocyte Typing V. Oxford: Oxford University Press, 1985). See also, Zola et al., 2000, *J. Biol. Regul. Homeost Agents,* 14: 311-6. All of the above-cited references are incorporated herein by reference in their entirety.

In some embodiments, the invention encompasses administering a molecule of the invention including but not limited to soluble FcγR polypeptides, fusion polypeptides comprising the extraceullular region of FcγR, and analogs and derivatives thereof in combination with a molecule or an agent that activates the inhibitory activity of FcγRIIB, such as anti-FcγRIIB antibodies, IVIG, immune complexes, or constructs comprising Fc regions such as those dislcosed in U.S. 2003/061826 which is incorporated herein by reference in its entirety. Any agent that can mimic aggregated IgG and immune complex function with respect to interaction with FcγR may be used in combination with the molecule of the invention. Anti-FcγRIIB antibodies that can be used in combination with the molecules of the invention are any anti-FcγRIIB antibodies known in the art or disclosed in U.S. Provisional Application No. 10/643,857 filed on Aug. 14, 2002, and U.S. application Ser. No. 10/643,857 filed on Aug. 14, 2003, both of which are incorporated herein by reference in their entireties. Preferably, the anti-FcγRIIB antibodies used in combination with the molecules of the invention activate the inhibitory activity of the FcγRIIB receptor. Examples of anti-FcγRIIB antibodies that may be used in accordance with the methods of the invention are 2B6 monoclonal antibody having ATCC accession number PTA-4591 and 3H7 having ATCC accession number PTA-4592 (deposited at ATCC, 10801 University Boulevard, Manassas, Va. 02209-2011, which are incorporated herein by reference).

In certain embodiments, a molecule of the invention is administered to a mammal, preferably a human, concurrently with one or more other therapeutic agents useful for the treatment of automimmune disorder or an inflammatory disorder. The term "concurrently" is not limited to the administration of prophylactic or therapeutic agents at exactly the same time, but rather it is meant that a molecule of the invention and the other agent are administered to a mammal in a-sequence and within a time interval such that the molecule of the invention can act together with the other agent to provide an increased benefit than if they were administered otherwise. For example, each prophylactic or therapeutic agent (e.g., an immunomodulatory agent, a molecule of the invention including but not limited to a fusion protein comprising the FcγRIIIA extracellular region) may be administered at the same time or sequentially in any order at different points in time; however, if not administered at the same time, they should be administered sufficiently close in time so as to provide the desired therapeutic or prophylactic effect. Each therapeutic agent can be administered separately, in any appropriate form and by any suitable route. In various embodiments, the prophylactic or therapeutic agents are administered less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In preferred embodiments, two or more components are administered within the same patient visit. In other embodiments, the prophylactic or therapeutic agents are administered at about 2 to 4 days apart, at about 4 to 6 days apart, at about 1 week part, at about 1 to 2 weeks apart, or more than 2 weeks apart. In preferred embodiments, the prophylactic or therapeutic agents are administered in a time frame where both agents are still active. One skilled in the art would be able to determine such a time frame by determining the half life of the administered agents.

In certain embodiments, the prophylactic or therapeutic agents of the invention are cyclically administered to a subject. Cycling therapy involves the administration of a first agent for a period of time, followed by the administration of a second agent and/or third agent for a period of time and repeating this sequential administration. Cycling therapy can reduce the development of resistance to one or more of the therapies, avoid or reduce the side effects of one of the therapies, and/or improves the efficacy of the treatment.

In certain embodiments, prophylactic or therapeutic agents are administered in a cycle of less than about 3 weeks, about once every two weeks, about once every 10 days or about once every week. One cycle can comprise the administration of a therapeutic or prophylactic agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In yet other embodiments, the therapeutic and prophylactic agents of the invention are administered in metronomic dosing regimens, either by continuous infusion or frequent administration without extended rest periods. Such metronomic administration can involve dosing at constant intervals without rest periods. Typically the therapeutic agents, in particular cytotoxic agents, are used at lower doses. Such dosing regimens encompass the chronic daily administration of relatively low doses for extended periods of time. In preferred embodiments, the use of lower doses can minimize toxic side effects and eliminate rest periods. In certain embodiments, the therapeutic and prophylactic agents are delivered by chronic low-dose or continuous infusion ranging from about 24 hours to about 2 days, to about 1 week, to about 2 weeks, to about 3 weeks to about 1 month to about 2 months, to about 3 months, to about 4 months, to about 5 months, to about 6 months.

When used in combination with other prophylactic and/or therapeutic agents, a molecule of the invention and the prophylactic and/or therapeutic agent can act additively or, more preferably, synergistically. In one embodiment, a molecule of the invention is administered concurrently with one or more therapeutic agents in the same pharmaceutical composition. In another embodiment, a molecule of the invention is administered concurrently with one or more other therapeutic agents in separate pharmaceutical compositions. In still another embodiment, a molecule of the invention is administered prior to or subsequent to administration of another prophylactic or therapeutic agent. The invention contemplates administration of a molecule of the invention in combination with other prophylactic or therapeutic agents by the same or different routes of administration, e.g., oral and parenteral. In certain embodiments, when a molecule of the invention is administered concurrently with another prophylactic or therapeutic agent that potentially produces adverse side effects including, but not limited to, toxicity, the prophylactic or therapeutic agent can advantageously be administered at a dose that falls below the threshold that the adverse side effect is elicited.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity and type of cancer, the route of administration, as well as age, body weight, response, and the past medical history of the patient. Suitable regimens can be selected by one skilled in the art by considering such factors and by following, for example, dosages reported in the literature and recommended in the Physician's Desk Reference ($56^{th}$ ed., 2002).

In a specific embodiment, the invention encompasses a method for treating, preventing, or ameliorating one or more symptoms of an autoimmune disorder (examples of autoimmune disorders is disclosed herein in Section 5.4.1), comprising administering a therapeutically effective amount of a soluble FcγR polypeptide, e.g., soluble FcγRIIIA, soluble FcγRIIB, in combination with a therapeutically effective amount of one or more therapeutic agents used for the treatment of an autoimmune disease known to those skilled in the art. Therapeutic agents that can be used in combination with the molecules of the invention are disclosed herein in Section 5.4.3.

In one specific embodiment, the invention encompasses a method for treating, preventing, or ameliorating one or more symptoms of an autoimmune disorder, comprising administering a therapeutically effective amount of a soluble FcγRIIIA polypeptide, in combination with a 3G8 antibody, preferably a 3G8 monoclonal antibody. Any variant, derivative or analog of a,3G8 antibody is contemplated in the methods and compositions of the invention. Specifically any variant, derivative or analog of a 3G8 antibody disclosed in U.S. Provisional Application No. 60/384,689, filed on May 30, 2002, and U.S. application Ser. No. 10/449,566 filed on May 29, 2003, and International Publication No. WO 03/101485, published on Dec. 11, 2003, all of which are incorporated herein by reference in their entireties, is contemplated by the methods and compositions of the present invention. In another embodiment, the invention encompasses administering a therapeutically effective amount of a soluble FcγRIIIA polypeptide with any FcγRIIIA binding protein, e.g., antibody, known in the art. In another specific embodiment, the invention encompasses a combination therapy comprising administering a therapeutically effective amount of a fusion protein comprising the extracellular region of an FcγR, e.g., FcγRIIIA, FcγRIIB, joined to an IgG2 hinge constant region, in combination with one or more additional therapeutic agents known to those skilled in the art for the treatment and/or prevention of an autoimmune disease.

In a certain embodiment, the invention encompasses a method for treating, preventing or ameliorating one or more symptoms of an autoimmune disorder, said method comprising administering to a subject, preferably human, in need thereof, a therapeutically effective amount of a molecule which specifically binds a wild-type extracellular region of FcγRIIIA comprising an Fcγ binding site, preferably an antibody, and a therapeutically effective amount of a dimeric fusion protein comprising two identical polypeptide chains, each said chain comprising a variant extracellular region of FcγRIIIA, wherein said variant extracellular region comprises at least one amino acid modification relative to said wild-type extracellular region, such that said molecule binds said dimeric fusion protein with a lower affinity than said molecule binds said wild-type extracellular region, and wherein said dimeric fusion protein specifically binds an immune complex. Such molecules which specifically bind a wild-type extracellular region of FcγRIIIA comprising an Fcγ binding site encompassed by the invention include, but are not limited to, antibodies known in the art that bind FcγRIIIA, e.g., CLB-GRAN1, BW2-9/2, GRM1, CLB-Gran1, DJ130c, LNK16, MEM-154, B88-9, PENI, 1D3, B73.1, BL-LGL/1, BL-LGL/2, VEP13, YFCF120.5, MG38 (See Tamm et al., 1996, Journal of Immunology, 157(4): 1566-1581, which is incorporated herein by reference in its entirety).

A number of monoclonal antibodies specific for the human FcγRIIIA are known in the art and have been used for treating autoimmune diseases, all of which can be used in combination with the molecules of the invention (see, e.g., Tamm and Schmidt, 1996, J. Imm. 157:1576-81, which is incorporated herein by reference in its entirety). One example is the mouse monoclonal antibody mAb 3G8, an $IgG_1$ antibody that recognizes the Fcγ-binding domain of human FcγRIIIA and B (Fleit et al., 1982, Proc. Natl. Acad. Sci. U.S.A 79:3275-79, which is incorporated herein by reference in its entirety). 3G8 has a Ka of $1\times10^9$ $M^{-1}$ for the receptor, and blocks the binding of human $IgG_1$ immune complexes to isolated human NK cells, monocytes and neutrophils, as well as to FcγRIIIA-transfected 293 cells. Other antibodies, for example, human or hunanized, polyclonal or monoclonal antibodies specific for FcγRIIIA can (see, e.g., Tamm and Schmidt, 1996, J. Imm. 157:1576-81; Fleit et al., 1989, p. 159 Leukocyte Typing IV: White Cell Differentiation Antigens, Kapp et al., eds. Oxford Univ. Press, Oxford; which are incorporated herein by reference in their entirety), be used in the treatment methods of the invention in combination with the molecules of the invention.

Preferably the anti-FcγRIIIA antibodies are human antibodies or humanized antibodies. Human antibodies against FcγRIIIA can be produced using transgenic animals having elements of a human immune system (see, e.g., U.S. Pat. Nos. 5,569,825 and 5,545,806, all of which are incorporated herein by reference in their entirety) or using human peripheral blood cells (Casali et al., 1986, Science 234:476, which is incorporated by reference herein in its entirety). In an alternative embodiment, human antibodies to FcγRIIIA can be produced by screening a DNA library from human B cells according to the general protocol outlined by Huse et al., 1989, Science 246:1275, which is incorporated herein by reference in its entirety. Antibodies binding to FcγRIIIA are selected and sequenced, and cloned. Alternatively, humanized antibodies can be made using techniques of antibody humanization known to those skilled in the art. In some embodiments the human or humanized antibodies are selected by competitive binding experiments or epitope mapping or other methods to have the same epitope specificity as 3G8.

In another embodiment, the invention encompasses a method for treating, preventing or ameliorating one or more symptoms of an autoimmune disorder, said method comprising administering to a subject in need thereof a therapeutically effective amount of the dimeric fusion protein comprising two identical polypeptide chains, i.e., identical polypeptide chains as used herein also refers to polypeptide chains having almost identical amino acid sequence, for example, including chains having one or more amino acid differences, preferably conservative amino acid substitutions, such that the activity of the two polypeptide chains is not significantly different, each said chain comprising a variant extracellular region of FcγRIIIA joined to a hinge-constant region of IgG2, wherein said variant extracellular region comprises at least one amino acid modification relative to a wild-type extracellular region of FcγRIIIA such that a 3G8 monoclonal antibody binds said dimeric fusion protein with a lower affinity than said monoclonal 3G8 antibody binds said wild-type extracellular region, and wherein the dimeric fusion protein specifically binds an immune complex, and a therapeutically effective amount of a 3G8 monoclonal antibody. In a most preferred embodiment, said 3G8 monoclonal antibody is humanized, as disclosed in U.S. Provisional application 60/384,689, filed on May 30, 2002, which is incorporated herein by reference in its entirety. In one embodiment, the one or more amino acid modification in the extracellular region of FcγRIIIA comprises a substitution in the 3G8 binding site. In a specific embodiment, the amino acid modification in the extracellular region of FcγRIIIA comprises a substitution at position 112 with aspartic acid, at position 113 with lysine, and at position 114 with proline. In yet another embodiment, the amino acid modification in the extracellular region of FcγRIIIA comprises a substitution at position 160 with phenylalanine. In another embodiment, the amino acid modification in the extracellular region of FcγRIIIA comprises a substitution at position 154 with asparagine and at position 155 with isoleucine.

In another embodiment, the invention encompasses a method for treating, preventing or ameliorating one or more symptoms of an autoimmune disorder, said method comprising administering to a subject in need thereof, a therapeutically effective amount of an antibody which specifically binds a wild-type extracellular region of FcγRIIB comprising an Fcγ binding site, e.g., an antibody produced from clone 2B6 or clone 3H7 having ATCC accession numbers PTA-4591, PTS-4592, respectively; and a therapeutically effective amount of a dimeric fusion protein comprising two identical polypeptide chains, each said chain comprising a variant extracellular region of FcγRIIB, wherein said variant extracellular region comprises at least one amino acid modification relative to said wild-type extracellular region, such that said antibody binds said dimeric fusion protein with a lower affinity than said antibody binds said wild-type extracellular region, and wherein said dimeric fusion protein specifically binds an immune complex.

5.4.3 Immunomodulatory Agents and Anti-Inflammatory Agents

The method of the present invention provides methods of treatment for autoimmune diseases and inflammatory diseases comprising administration of the molecules of the present invention in conjunction with other treatment agents. Examples of immunomodulatory agents include, but are not limited to, methothrexate, ENBREL, REMICADE™, leflunomide, cyclophosphamide, cyclosporine A, and macrolide antibiotics (e.g., FK506 (tacrolimus)), methylprednisolone (MP), corticosteroids, steriods (e.g., cortisol, cortison, Fludrocortisone, Prednisone, Prednisolone, Triamcinolone, Betamethasone, Dexamethasone), mycophenolate mofetil, rapamycin (sirolimus), mizoribine, deoxyspergualin, brequinar, malononitriloamindes (e.g., leflunamide), T cell receptor modulators, and cytokine receptor modulators.

Steroids that may be used in the methods and compositions of the invention include but are not limited to, aldlometasone diproprionate, amcinonide, beclomethasone dipropionate, betametasone, betamethasone benzoate, betamethasone diproprionate, betamethasone sodium phosphate, betamethasone valerate, clobetasol proprionate, clocortolone pivalate, hydrocortisone, hydrocortisone derivatives, desonide, desoximatasone, dexamethasone, flunisolide, flucoxinolide, flurandrenolide, halcinocide, medrysone, methylprednisolone, methprednisolone acetate, methylprednisolone sodium succinate, mometasone furoate, paramethasone acetate, prednisolone, prednisolone acetate, prednisolone sodium phosphate, prednisolone tebuatate, prednisone, triamcinolone, triamcinolone acetonide, triamcinolone diacetate, and triamcinolone hexacetonide.

Anti-inflammatory agents have exhibited success in treatment of inflammatory and autoimmune disorders and are now a common and a standard treatment for such disorders. Any anti-inflammatory agent well-known to one of skill in the art can be used in the methods of the invention. Non-limiting examples of anti-inflammatory agents include non-steroidal anti-inflammatory drugs (NSAIDs), steroidal anti-inflammatory drugs, beta-agonists, anticholingeric agents, and methyl xanthines. Examples of NSAIDs include, but are not limited to, aspirin, ibuprofen, celecoxib (CELEBREX™), diclofenac (VOLTAREN™), etodolac (LODINE™), fenoprofen (NALFON™), indomethacin (INDOCIN™), ketoralac (TORADOL™, oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxgenase enzyme (e.g., COX-1 and/or COX-2). Examples of steroidal anti-inflammatory drugs include, but are not limited to, glucocorticoids, dexamethasone (DECADRON™), cortisone, hydrocortisone, prednisone (DELTASONE™), prednisolone, triamcinolone, azulfidine, and eicosanoids such as prostaglandins, thromboxanes, and leukotrienes.

5.5 Compositions and Methods of Administering

The invention provides methods and pharmaceutical compositions comprising molecules of the invention. The invention also provides methods of treatment, prophylaxis, and amelioration of one or more symptoms associated with a disease or disorder by administering to a subject a therapeutically effective amount of molecule of the invention, e.g., a soluble polypeptide, a soluble fusion polypeptide, derivatives, and analogs of these molecules, and nucleic acids encoding same, or a pharmaceutical composition comprising a a molecule of the invention. In a preferred aspect, a molecule of the invention, is substantially purified (i.e., substantially free from substances that limit its effect or produce undesired side-effects). In a specific embodiment, the subject is an animal, preferably a mammal such as non-primate (e.g., cows, pigs, horses, cats, dogs, rats etc.) and a primate (e.g., monkey such as, a cynomolgous monkey and a human). In a preferred embodiment, the subject is a human.

Various delivery systems are known and can be used to administer a composition comprising a molecule of the invention and pharmaceutically acceptable salts thereof, e.g., encapsulation in liposomes, microparticles, microcapsules, recombinant cells capable of expressing the molecule of the invention, construction of a nucleic acid as part of a retroviral or other vector, etc.

Methods of administering a molecule of the invention include, but are not limited to, parenteral administration (e.g., intradermal, intramuscular, intraperitoneal, intravenous and subcutaneous), epidural, and mucosal (e.g., intranasal and oral routes). In a specific embodiment, the molecules of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety. In most preferred embodiments, the compositions of the invention are self-administered thus providing enhanced patient compliance.

In some preferred embodiments, the compositions of the invention are prepared using a batch process method as crystalline suspensions such as those disclosed in WO 02/072636, which is incorporated herein by reference in its entirety. The purity and integrity of the preparations are determined using standard methods known to one skilled in the art such as SDS-PAGE, capillary isoelectric focusing, size exclusion chromatography-HPLC, dynamic light scattering, MS, peptide mapping, etc. Preferably, the crystalline compositions of the invention are administered s.c. in a small volume and highly concentrated using methods described by Yang et al. (2003, *PNAS*, 100(12): 6934-9, which is incorporated herein by reference in its entirety). Administration of compositions using this technology results in a long pharmacokinetic serum profile and higher bioavailability relative to conventional modes of administration.

The invention also provides that the molecules of the invention are packaged in a hermetically sealed container such as an ampoule or sachette indicating the quantity of antibody. In one embodiment, the molecules of the invention are supplied as a dry sterilized lyophilized powder or water free concentrate in a hermetically sealed container and can be reconstituted, e.g., with water or saline to the appropriate concentration for administration to a subject. Preferably, the molecules of the invention are supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. The lyophilized molecules of the invention should be stored at between 2 and 8° C. in their original container and the molecules should be administered within 12 hours, preferably within 6 hours, within 5 hours, within 3 hours, or within 1 hour after being reconstituted. In an alternative embodiment, molecules of the invention are supplied in liquid form in a hermetically sealed container indicating the quantity and concentration of the antibody, fusion protein, or conjugated molecule. Preferably, the liquid form of the molecules are supplied in a hermetically sealed container at least 1 mg/mL, more preferably at least 2.5 mg/mL, at least 5 mg/mL, at least 8 mg/mL, at least 10 mg/mL, at least 15 mg/mL, at least 25 mg/mL, at least 50 mg/mL, at least 100 mg/mL, at least 150 mg/mL, at least 200 mg/mL of the antibodies.

The amount of the composition of the invention which will be effective in the treatment, prevention or amelioration of one or more symptoms associated with a disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

For molecules encompassed by the invention, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight.

In one embodiment, the dosage of a molecules of the invention administered to a patient are 0.01 mg to 1000 mg/day, when used as single agent therapy. In another embodiment a molecules of the invention is used in combination with other therapeutic compositions and the dosage administered to a patient is lower than when said molecules is used as a single agent therapy.

In a specific embodiment, it may be desirable to administer the pharmaceutical compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering a molecules of the invention, care must be taken to use materials to which the molecule does not absorb.

In another embodiment, the compositions can be delivered in a vesicle, in particular a liposome (See Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the compositions can be delivered in a controlled release or sustained release system. Any technique known to one of skill in the art can be used to produce sustained release formulations comprising a molecule of the invention. See, e.g., U.S. Pat. No. 4,526,938; PCT publication WO 91/05548; PCT publication WO 96/20698; Ning et al., 1996, "Intratumoral Radioimmunotheraphy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397; Cleek et al., 1997, "Biodegradable Polymeric Carriers for a bFGF Antibody for Cardiovascular Application," Pro. Int'l. Symp. Control. Rel. Bioact. Mater. 24:853-854; and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in its entirety.

In one embodiment, a pump may be used in a controlled release system (See Langer, supra; Sefton, 1987, CRC Crit. Ref. Biomed. Eng. 14:20; Buchwald et al., 1980, Surgery 88:507; and Saudek et al., 1989, N. Engl. J. Med. 321:574). In another embodiment, polymeric materials can be used to achieve controlled release of a molecule of the invention (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; See also Levy et al., 1985, Science 228:190; During et al., 1989, Ann. Neurol. 25:351; Howard et al., 1989, J. Neurosurg. 71:105); U.S. Pat. Nos. 5,679,377; 5,916,597; 5,912,015; 5,989,463; 5,128,326; PCT Publication No. WO 99/15154; and PCT Publication No. WO 99/20253). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In yet another embodiment, a controlled release system can be placed in proximity of the therapeutic target (e.g., the lungs), thus requiring only a fraction of the systemic dose (see, e.g., Goodson, in Medical Applications of Controlled Release, supra, vol. 2, pp. 115-138 (1984)). In another embodiment, polymeric compositions useful as controlled release implants are used according to Dunn et al. (See U.S. Pat. No. 5,945,155). This particular method is based upon the therapeutic effect of the in situ controlled release of the bioactive material from the polymer system. The implantation can generally occur anywhere within the body of the patient in need of therapeutic treatment. In another embodiment, a non-polymeric sustained delivery system is used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (See U.S. Pat. No. 5,888,533).

Controlled release systems are discussed in the review by Langer (1990, Science 249:1527-1533). Any technique known to one of skill in the art can be used to produce sustained release formulations comprising one or more therapeutic agents of the invention. See, e.g., U.S. Pat. No. 4,526,938; International Publication Nos. WO 91/05548 and WO 96/20698; Ning et al., 1996, Radiotherapy & Oncology 39:179-189; Song et al., 1995, PDA Journal of Pharmaceutical Science & Technology 50:372-397; Cleek et al., 1997, Pro. Int'l. Symp. Control. Rel. Bioact. Mater. 24:853-854; and Lam et al., 1997, Proc. Int'l. Symp. Control Rel. Bioact. Mater. 24:759-760, each of which is incorporated herein by reference in its entirety.

In a specific embodiment where the composition of the invention is a nucleic acid encoding a molecule of the invention, the nucleic acid can be administered in vivo to promote expression of its encoded molecule, by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al., 1991, Proc. Natl. Acad. Sci. USA 88:1864-1868), etc. Alternatively, a nucleic acid can be introduced intracellularly and incorporated within host cell DNA for expression by homologous recombination.

Compositions comprising a molecule of the invention or a pharmaceutically acceptable salt thereof can additionally comprise a suitable amount of a pharmaceutically acceptable vehicle so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, mammals, and more particularly in humans. The term "vehicle" refers to a diluent, adjuvant, excipient, or carrier with which a molecule of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Compound compositions, if desired, can also contain minor amounts of wetting or emulsifying agents, or pH buffering agents.

Compositions of the invention can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in Remington's Pharmaceutical Sciences, Alfonso R. Gennaro, ed., Mack Publishing Co. Easton, Pa., 19th ed., 1995, pp. 1447 to 1676, incorporated herein by reference.

In a preferred embodiment, the molecule of the invention or a pharmaceutically acceptable salt thereof is formulated in accordance with routine procedures as a pharmaceutical composition adapted for oral administration to human beings. Compositions for oral delivery may be in the form of tablets, lozenges, aqueous or oily suspensions, granules, powders, emulsions, capsules, syrups, or elixirs, for example. Orally administered compositions may contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, and the like. Such vehicles are preferably of pharmaceutical grade. Typically, compositions for intravenous administration comprise sterile isotonic aqueous buffer. Where necessary, the compositions may also include a solubilizing agent.

In another embodiment, the molecule of the invention or a pharmaceutically acceptable salt thereof can be formulated for intravenous administration. Compositions for intravenous administration may optionally include a local anesthetic such as lignocaine to lessen pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the compound or a pharmaceutically acceptable salt thereof is to be administered by infusion, it can be dispensed, for example, with an infusion bottle containing sterile pharmaceutical grade water or saline. Where the compound or a pharmaceutically acceptable salt thereof is administered by injection, an ampoule of sterile water for injection or saline can be provided so that the ingredients may be mixed prior to administration.

The amount of a molecule of the invention or a pharmaceutically acceptable salt thereof that will be effective in the treatment of a particular disease will depend on the nature of the disease, and can be determined by standard clinical techniques. In addition, in vitro or in vivo assays may optionally be employed to help identify optimal dosage ranges. The precise dose to be employed will also depend on the route of administration, and the seriousness of the disease, and should be decided according to the judgment of the practitioner and each patient's circumstances. However, suitable dosage ranges for oral administration are generally about 0.001 milligram to about 200 milligrams of a compound or a pharmaceutically acceptable salt thereof per kilogram body weight per day. In specific preferred embodiments of the invention, the oral dose is about 0.01 milligram to about 100 milligrams per kilogram body weight per day, more preferably about 0.1 milligram to about 75 milligrams per kilogram body weight per day, more preferably about 0.5 milligram to 5 milligrams per kilogram body weight per day. The dosage amounts described herein refer to total amounts administered; that is, if more than one compound is administered, or if a compound is administered with a therapeutic agent, then the preferred dosages correspond to the total amount administered. Oral compositions preferably contain about 10% to about 95% active ingredient by weight.

Suitable dosage ranges for intravenous (i.v.) administration are about 0.01 milligram to about 100 milligrams per kilogram body weight per day, about 0.1 milligram to about 35 milligrams per kilogram body weight per day, and about 1 milligram to about 10 milligrams per kilogram body weight per day. Suitable dosage ranges for intranasal administration are generally about 0.01 pg/kg body weight per day to about 1 mg/kg body weight per day. Suppositories generally contain about 0.01 milligram to about 50 milligrams of a compound of the invention per kilogram body weight per day and comprise active ingredient in the range of about 0.5% to about 10% by weight.

Recommended dosages for intradermal, intramuscular, intraperitoneal, subcutaneous, epidural, sublingual, intracerebral, intravaginal, transdermal administration or administration by inhalation are in the range of about 0.001 milligram to about 200 milligrams per kilogram of body weight per day. Suitable doses for topical administration are in the range of about 0.001 milligram to about 1 milligram, depending on the area of administration. Effective doses may be extrapolated from dose-response curves derived from in vitro or animal model test systems. Such animal models and systems are well known in the art.

The molecule of the invention and pharmaceutically acceptable salts thereof are preferably assayed in vitro and in vivo, for the desired therapeutic or prophylactic activity, prior to use in humans. For example, in vitro assays can be used to determine whether it is preferable to administer the molecule, a pharmaceutically acceptable salt thereof, and/or another therapeutic agent. Animal model systems can be used to demonstrate safety and efficacy.

5.6 Characterization and Demonstration of Therapeutic Utility

Several aspects of the pharmaceutical compositions, prophylactic, or therapeutic agents of the invention are preferably tested in vitro, in a cell culture system, and in an animal model organism, such as a rodent animal model system, for the desired therapeutic activity prior to use in humans. For example, assays which can be used to determine whether administration of a specific pharmaceutical composition is desired, include cell culture assays in which a patient tissue sample is grown in culture, and exposed to or otherwise contacted with a pharmaceutical composition of the invention, and the effect of such composition upon the tissue sample is observed. The tissue sample can be obtained by biopsy from the patient. This test allows the identification of the therapeutically most effective prophylactic or therapeutic molecule(s) for each individual patient. In various specific embodiments, in vitro assays can be carried out with representative cells of cell types involved in an autoimmune or inflammatory disorder (e.g., T cells), to determine if a pharmaceutical composition of the invention has a desired effect upon such cell types.

Preferred animal models for use in the methods of the invention are, for example, transgenic mice expressing human FcγRs on mouse effector cells, e.g., any mouse model described in U.S. Pat. No. 5,877,396 (which is incorporated herein by reference in its entirety) can be used in the present invention. Transgenic mice for use in the methods of the invention include, but are not limited to, mice carrying human FcγRIIIA; mice carrying human FcγRIIA; mice carrying human FcγRIIB and human FcγRIIIA; mice carrying human FcγIIB and human FcγRIIA.

The invention encompasses any animal model for lupus, AHA, EAE, glomerulonephritis that are known to those skilled in the art. The invention encompasses animal models for glomerulonephritis such as those developed by Clynes et al. (1998, *Science*, 279: 1052-4, which is incorporated herein by reference in its entirety). Breifly, New Zealand back (NZB) mice develop autoantibodies and autoimmune hemolytic anemica but show no signs of glomerular disease until crossed to the New Zealand White(NZW) background mice to generate NZB/NZW (B/W $F_1$) mice. A minimum of three distinct genetic loci are needed for the manifestation of autoimmune glomerulonephritis in the BIW $F_1$, two derived from NZB and one from NZW mice (See, e.g., Theofilopoulos and Dixon, 1985, *Adv. Immunol.* 37: 269; Morel et al., 1994, *Immunity*, 1: 219; Vyse et al., 1996, *Curr. Opin. Immunol.* 8: 843; all of which is incorporated herein by reference in its entirety). Several features of this model are consistent with lupus in humans. Clynes and colleagues backcrossed NZB and NZW mice for eight generation to the mouse strain γ–/– which is deficient in FcγR receptor g chains and does not express activation receptors FcγRI and FcγRIII but still contains FcγRIIB. Animals homozygous or heterozygous for disruption of g chain were identified. These mice generated and deposited immune complexes but were protected from severe nephritis.

In some embodiments, the invention encompasses animal models for systemic lupus erythemastosus (SLE) such as those developed by Bolland et al. (2002, *J. Exp. Med.* 195(9): 1167-1174; which is incorporated herein by reference in its entirety). Briefly, hybrids were generated between B6.RIB–/– and the Sle susceptibility locus or the SLE modifiers yaa and 1 pr.

The invention provides FcγRIIB-deficient mice known in the art as animal models for autoimmune disease, such as FcγRIIB-deficient mice of the H-2b haplotype which is susceptible to type II collagen induced arthritis, a model for rheumatoid arthritis in humans, see, e.g., Yuasa et al., 1999, *J. Exp. Med.* 189: 187-194; which is incorporated herein by reference in its entirety. Additionally the invention encompasses FcγRIIB-deficient murine models that develop Goodpasture's Syndrome (GPS) upon immunization with Type IV collagen, see, e.g., Nakamura et al., 2000, *J. Exp. Med.* 191 (5): 899-905, which is incorporated herein by reference in its entirety. GPS is an autoimmune dieseas resulting from the interation of pathogenic anti-collagen type IV antibodies with alveolar and glomular basement membranes.

In some embodiments, the invention encompasses K/BxN T cell receptor transgenic mice (KRN mice), a model of inflammatory arthritis that is critically dependent on both T and B cells. This mouse model exhibits many of the features of human rheumatoid arthritis which is mainly initiated by T cells but is almost entirely sustained by antibodies to the self-antigen glucose 6 phosphate isomerase. Spontaneous arthritis in these KRN transgenic mice is due to autoreactivity of the transgenic T cell receptor against Ag7 MHC molecules which leads to strong but incomplete clonal deletion. For a review of KRN mice technology see, e.g., Ji et al., 2001, J. Exp. Med. 194(3): 321-30; Schaller et al., 2001, Nat. Immunol. 2(8): 746-53; Wipke et al., 2001, J. Immunol. 167(3): 1601-8; Korganow wt al., 1999, Immunity, 10(4): 451-61; Basu et al., 2001, J. Immunol. 166(6): 4005-11; Kyburz et al., 2000, Arthritis Rheum. 43(11): 2571-7; de Bandt et al., 2000, Arthritis Rheum. 43(9): 2056-63; Basu et al., 2000, J. Immunol. 164(11): 5788-96, Mangialaio et al., 1999, Arthritis Rheum. 42(12): 2517-23; Ji et al., 1999, Immunol. Rev. 169: 139-46, Ji et al., 2002, Immunity, 16: 157-68, Basu et al., 2001, J. Immunol. 166: 4005-11; all of which are incorporated herein by reference in their entireties.

An exemplary model system for use in the invention is a mouse model for idiopathic thrombocytopenic purpura (ITP) (see, Oyaizu et al., 1988, J Exp. Med. 167:2017-22; Mizutani et al., 1993, *Blood* 82:837-44). See Example 6, infra. Other suitable models are known in the art. Other animal models include rodent models of inflammatory diseases described in, for example, Current Protocols in Immunology (in some cases modified by using animals transgenic for human FcγRIIIA).

Another exemplary animal model for testing the therapeutic efficacy of the molecules of the invention is a mouse FcγRIIIA$^{-/-}$, human FcγRIIIB transgenic mouse for measuring neutropenia after administering the molecules of the invention to the mice. Preferably the molecules of the invention bind FcγRIIIA and have a protective effect against autoimmune diseases. Additionally, the molecules of the invention can bind FcγRIIIB on the surface of neutrophils and mediate neutrophil depletion (neutropenia) which is the basis of the neutropenia assay. Briefly, the molecules of the invention or controls such as irrelevant human IgG1 (negative control) or murine RB6-8C5 (positive control) are administered to groups of muFcγRIII–/–, huFcγRIIIB transgenic mice at a concentration of 5 mg/g in phosphate buffer saline (PBS). Another negative control administered can be PBS alone. Twenty four hours later, mice are euthanized and blood, spleen and bone marrow are collected. Neutrophils are analyzed by FACS. Staining experiments are performed in RPMI containing 3% FCrS. Murine cells are stained using FITC-conjugated 3G8 (PharMingen) and R-PE-conjugated RB6-8C5 (PharMingen). Samples are analyzed by flow-cytometry using a FACSCalibur (Becton Dickinson). Neutrophil shedding is thus quantitated.

Other assays which can be used to determine whether administration of a specific pharmaceutical composition is desired, include cell culture assays in which a patient tissue sample is grown in culture, and exposed to or otherwise contacted with a pharmaceutical composition of the invention, and the effect of such composition upon the tissue sample is observed. The tissue sample can be obtained by biopsy from the patient. This test allows the identification of the therapeutically most effective prophylactic or therapeutic molecule(s) for each individual patient. In various specific embodiments, in vitro assays can be carried out with representative cells of cell types involved in an autoimmune or inflammatory disorder (e.g., T cells), to determine if a pharmaceutical composition of the invention has a desired effect upon such cell types.

Combinations of prophylactic and/or therapeutic agents can be tested in suitable animal model systems prior to use in humans. Such animal model systems include, but are not limited to, rats, mice, chicken, cows, monkeys, pigs, dogs, rabbits, etc. Any animal system well-known in the art may be used. In a specific embodiment of the invention, combinations of prophylactic and/or therapeutic agents are tested in a mouse model system. Such model systems are widely used and well-known to the skilled artisan. Prophylactic and/or therapeutic agents can be administered repeatedly. Several aspects of the procedure may vary. Said aspects include the temporal regime of administering the prophylactic and/or therapeutic agents, and whether such agents are administered separately or as an admixture.

The anti-inflammatory activity of the combination therapies of invention can be determined by using various experimental animal models of inflammatory arthritis known in the art and described in Crofford L. J. and Wilder R. L., "Arthritis and Autoimmunity in Animals", in Arthritis and Allied Conditions: A Textbook of Rheumatology, McCarty et al.(eds.), Chapter 30 (Lee and Febiger, 1993). Experimental and spontaneous animal models of inflammatory arthritis and autoimmune rheumatic diseases can also be used to assess the anti-inflammatory activity of the combination therapies of invention. The following are some assays provided as examples, and not by limitation.

The principle animal models for arthritis or inflammatory disease known in the art and widely used include: adjuvant-induced arthritis rat models, collagen-induced arthritis rat and mouse models and antigen-induced arthritis rat, rabbit and hamster models, all described in Crofford L. J. and Wilder R. L., "Arthritis and Autoimmunity in Animals", in Arthritis and Allied Conditions: A Textbook of Rheumatology, McCarty et al.(eds.), Chapter 30 (Lee and Febiger, 1993), incorporated herein by reference in its entirety.

The anti-inflammatory activity of the combination therapies of invention can be assessed using a carrageenan-induced arthritis rat model. Carrageenan-induced arthritis has also been used in rabbit, dog and pig in studies of chronic arthritis or inflammation. Quantitative histomorphometric assessment is used to determine therapeutic efficacy. The methods for using such a carrageenan-induced arthritis model is described in Hansra P. et al., "Carrageenan-Induced Arthritis in the Rat," Inflammation, 24(2): 141-155, (2000). Also commonly used are zymosan-induced inflammation animal models as known and described in the art.

The anti-inflammatory activity of the combination therapies of invention can also be assessed by measuring the inhibition of carrageenan-induced paw edema in the rat, using a modification of the method described in Winter C. A. et al., "Carrageenan-Induced Edema in Hind Paw of the Rat as an Assay for Anti-inflammatory Drugs" Proc. Soc. Exp. Biol Med. 111, 544-547, (1962). This assay has been used as a primary in vivo screen for the anti-inflammatory activity of most NSAIDs, and is considered predictive of human efficacy. The anti-inflammatory activity of the test prophylactic or therapeutic agents is expressed as the percent inhibition of the increase in hind paw weight of the test group relative to the vehicle dosed control group.

Additionally, animal models for inflammatory bowel disease can also be used to assess the efficacy of the combination therapies of invention (Kim et al., 1992, Scand. J. Gastroentrol. 27:529-537; Strober, 1985, Dig. Dis. Sci. 30(12 Suppl): 3S-10S). Ulcerative cholitis and Crohn's disease are human inflammatory bowel diseases that can be induced in animals. Sulfated polysaccharides including, but not limited to amylopectin, carrageen, amylopectin sulfate, and dextran sulfate or chemical irritants including but not limited to trinitrobenzenesulphonic acid (TNBS) and acetic acid can be administered to animals orally to induce inflammatory bowel diseases.

Animal models for autoimmune disorders can also be used to assess the efficacy of the combination therapies of invention. Animal models for autoimmune disorders such as type 1 diabetes, thyroid autoimmunity, sytemic lupus eruthematosus, and glomerulonephritis have been developed (Flanders et al., 1999, Autoimmunity 29:235-246; Krogh et al., 1999, Biochimie 81:511-515; Foster, 1999, Semin. Nephrol. 19:12-24).

Further, any assay known to those skilled in the art can be used to evaluate the prophylactic and/or therapeutic utility of the therapies disclosed herein for autoimmune and/or inflammatory diseases. The therapeutic utility of the molecules and compositions of the invention in combination with standard ITP therapies, e.g., IVIG, can be evaluated for using assays known to those skilled in the art, including but not limited to, determining platelet levels, determining the levels of murine immunoglobulin and antimurine immunoglobulin, determining the levels of anti-idiotypes, determining natural killer cell function, measuring clearance of immune complexes, measuring clearance of opsonized red cells in subjects who have undergone splenectomy (See e.g., Hunter, 1978, Handbook of Experimental Immunology, $3^{rd}$ ed. Oxford: Blackwell, 14:01-14.37; Shawler et al., 1985, Journal of Immunology, 135: 1530-5; West et al., 1977 Journal of Immunolgoy, 355-61; McDougal et al., 1979, Journal of Clinical Invest. 63: 627-36; Hosea et al., 1981 N. England Journal of Med., 304: 245-50; Frank et al., 1979, N. England Journal of Med., 300: 518-23, all of which is incorporated herein, by reference in its entirety).

Toxicity and efficacy of the prophylactic and/or therapeutic protocols of the instant invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

Molecules of the invention for use in therapy can be tested in suitable animal model systems prior to testing in humans, including but not limited to in rats, mice, chicken, cows, monkeys, rabbits, hamsters, etc., for example, the animal models described above. The compounds can then be used in the appropriate clinical trials.

Further, any assays known to those skilled in the art can be used to evaluate the prophylactic and/or therapeutic utility of the combinatorial therapies disclosed herein for treatment or prevention of inflammatory disorder or autoimmune disease.

6. EXAMPLES

6.1 Engineering of Soluble FcγR Fusion Proteins

Soluble FcγRIIIA and FcγRIIIB fusion proteins were generated by fusing the extracellular regions of each receptor to the constant region of IgG2. The extracellular domain of human FcγRIIIA was fused to the hinge-CH2-CH3 (i.e., hinge-constant region) region of human IgG2 (this construct will be referred to as "sFcγRIIIA-G2"; SEQ. ID. NO. 6). The IgG2 constant region was chosen because the FcγR does not bind to this constant region. The extracellular region of FcγRIIIA was amplified using a full length cDNA clone as template (gift from Dr. Jeffrey Ravetch, Rockefeller University) using the following primers: SJ45f (CTC TCC ACA GGT GTC CAC TCC ATG CGG ACT GAA GAT CTC CCC; SEQ ID NO: 10); and SJ48r (GCG CTC GAC TTG GTA CCC AGG TGG; SEQ ID NO: 11). This amplified fragment was then joined to a signal sequence coding segment (source of signal sequence: Synthetic construct made at MacroGenics based on mouse genomic segment coding for a VH signal sequence and intron, GENBANK Accession No. M12880; Primers: H009 (CGA GCT AGC TGA GAT CAC AGT TCT CTC TAC; SEQ ID NO: 12); SJ27r (GGA GTG GAC ACC TGT GGA GAG; SEQ ID NO: 13))and to the IgG hinge-CH2-CH3 (amino acids 216-446) segment by an overlapping PCR procedure. Source of the IgG2 constant region was PMGX101: cDNA clone made at MacroGenics, and the primers were SJ47f (CCT GGG TAC CAA GTC GAG CGC AAA TGT TGT GTC GAG TGC CC; SEQ ID NO: 14) and SJ20r (GGC GAA TTC GCG GCC GCA CTC ATT TAC CCG GAG ACA GG; SEQ ID NO: 15). The resulting fragment was digested with NheI and EcoRI and cloned into the mammalian expression vector pCI-neo. The inclusion of the hinge region allows flexibility of the two receptor arms and covalent disulfide linkage of the each monomer.

The soluble FcγRIIIB was also fused to the IgG2 constant region to generate the "sFcγRIIB-G2" construct, SEQ. ID. No. 5. The extracellular region of FcγRIIB (amino acids 137-676) including its own signal sequence (amino acids 11-136) was amplified from a cDNA clone (Source of FcγRIIB cDNA; gift from Dr. Jeffrey Ravetch, Rockefeller University Primers for amplification were SJ84f (GGC GGC TAG CCA CCA TGG GAA TCC TGT CAT TCT TAC C; SEQ ID NO: 16); and SJ82r (CAT TTG CGC TCC CCC ATG GGT GAA GAG CTG GGA GC; SEQ ID NO: 17) and joined to the hinge-CH2-CH3 cDNA of human IgG2 constant region by overlapping PCR. The resulting fragment was digested with NheI and EcoRI and cloned into the mammalian expression vector pCI-neo.

6.2 Generation of Stably-Transfected HEK-293 Cell Lines that Secrete the FcγRIIIA-G2 and FcγRIIB-G2 Soluble Receptor—IgG Fusion Proteins Cell Culture: The 293H cell line was obtained from GIBCO (Grand Island, N.Y.) and maintained as adherent cells in Dulbecco's MEM (D-MEM, high glucose (4,500 mg/L D-glucose), with L-glutamine, and phenol red) supplemented with 0.1 mM non-essential amino acids (NEAA) and 10% Fetal Bovine Serum (FBS). Cell cultures were maintained at 37° C. with 5% $CO_2$.

Transfection: The day before transfection, 293H cells were plated in 6-well, poly-lysine coated plates at a seeding density of $1\times10^6$ cells/well in 2 mL of culture medium. Plasmid DNA constructs that express the modified heavy and light chains and a G418-resistance cassette (5 μg total DNA per well) were transfected into the cells with 10 mL per well of Lipofectamine 2000 cationic lipid reagent (Invitrogen, Carlsbad, Calif.). At 48 hours post-transfection cells were subcultured into 10 cm dishes at varying dilutions. The following day, culture medium was replaced with selection medium containing 800 μg/mL of active G418. Stable, single, isolated colonies were collected and transferred to 96-well plates.

Protein Expression: Culture supernatants from each well were screened by an ELISA assay to determine expression of FcγRIIIA-G2 and FcγRIIBG2 soluble fusion proteins. Briefly, Nunc F96 MaxiSorp Immunoplate plates were coated with 2 μg/mL goat anti-human IgG antibody in carbonate buffer and incubated overnight at 4° C. The plates were blocked with PBS-0.1% Tween-0.5% BSA and incubated for 30' at RT. Human IgG2 was used as reference standard. 50 mL of each standard and samples were added to duplicate cells on plate; include a minimum of 2 wells with PBS/T-BSA as plate blanks and incubate at RT for 1 hour and then washed 3× with PBS-T. Goat anti-mouse antibody conjugated with HRP (1:1000) was added to the plate and incubated at room temperature for 1 hr and then the plate was washed 3× with PBS-T. The plate was developed by adding 100 μL/well of TMB reagent, incubated for 5 min at RT in the dark; 50 μL/well of stop solution (0.18 M sulfuric acid) was added to stop the reaction. The plate was read at 450 nM.

One clone from each transfection was selected and expanded for subsequent protein expression. Clones were expanded and maintained in growth medium with 300 μg/ml G418. Expression levels were stable for at least three months in the expanded clones. Expression of soluble receptor fusion protein was up to 16.4 mg/L and 15.0 mg/L for FcγRIIBG2 and FcγRIIIA-G2 respectively, after 9 days of culture.

Purification: Purification was accomplished by Protein G chromatography followed by affinity chromatography on a human IgG-sepharose column with a yield of approximately 60 percent and a purity of approximately 95 percent. Concentration was determined by $OD_{280}$ measurement and purity was evaluated by SDS-PAGE (data not shown) The ability of the fusion proteins to bind the IgG column indicates that the fusion proteins are correctly folded and retain IgG binding.

6.3 Generation of Mutants of FcγRIIIA-G2 Fusion Proteins sFcγRIIIA-G2 Mutants which Lack Binding to an FcγRIIIA Monoclonal Antibody, the 3G8 Monoclonal Antibody, but Retain their Fcγ Binding Capability The construct sFcγRIIIA-G2 was mutagenized in order to generate soluble FcγRIIIA fusion proteins, which lack binding to an FcγRIIIA monoclonal antibody, the 3G8 monoclonal antibody, but retain their Fcγ binding capability. These mutant fusion proteins could, either alone, or in combination with humanized 3G8 monoclonal antibody, interfere with immune complex binding to FcγRs in vivo, and thus have therapeutic utility when immune complex clearance is desired.

Human soluble FcγRIIIA was fused with human IgG2 Fcγ portion and is defined as sFcγRIIIA-G2, as described supra. The sFcγRIIIA-G2 amino acid residues which interact with human IgG1 Fcγ were selected for mutagenesis in order to generate mutants that lacked 3G8 binding while maintaining Fcγ binding.

FcγRIIIA binds human Fcγ region with the B/C loop (Trp 110 to Ala 114), F/G loop (Val 155 to Lys 158), the C strand (His 116 to Thr 119), and the C' strand (Asp 126 to His 132). Additionally, Arg 152 and the connector between the N-terminal domain 1 and domain 2 (Ile 85 to Trp 87) is involved in binding (Sondermann et al.; Tamm et al.). Previous studies have suggested that 3G8 monoclonal antibody binds to FcγRIIIA at residues 109-114 and 156-160.

Based on sequence alignments between FcγRIIIA and FcγRIIB, the binding site of FcγRIIIA on Fcγ deduced from the crystallographic analysis, as well as the available data on the 3G8 binding site on FcγRIIIA, the following mutants were generated in the fusion protein comprising the soluble region of FcγRIIIA fused to IgG2 constant region by the Stratagene Quick Change Method.

Table 2: lists of the mutations that were introduced into the FcγRIIIA-IgG2 fusion protein.

TABLE 2

MUTATIONS IN FcγRIIIA-IgG2

| STRUCTURAL MOTIF IN FcγRIIIA | PLASMID | MUTATION |
|---|---|---|
| B/C loop (Trp 110 to Ala 114) | pMGX330 | 112NTA1 14 --> IIB (DKP) |
| | pMGX338 | N112D |
| | pMGX339 | T113K |
| | pMGX340 | A114P |
| C strand | pMGX331 | H116V |
| C' strand | pMGX337 | G126D |
| F/G loop | pMGX327 | 156GSKNV160 --> IIB (GYTLF) |
| | pMGX328 | V160F |
| | pMGX329 | 154LV155 --> IIB (NI) |

Stability Studies

The sFcγRIIIAG2 fusion protein was unstable when stored at 4° C. and formulated in PBS. The pronounced appearance of smaller molecular weight degradation products was evident by SDS-PAGE analysis within 2 months of storage. In order to characterize the cause of the instability, the degradation fragments were functionally and biochemically analyzed. Four variants were generated as shown in FIG. 1A. The degraded product was subjected to chromatography on either a protein G or a human IgG matrix and the bound and unbound fractions were analyzed by SDS-PAGE and western blot. A distinct binding pattern was observed in which one degradation fragment (28 kd) bound to protein G Sepharose and the other fragment bound to the IgG Sepharose (38 kd). This data implied that the fusion protein was being cleaved between the FcγR3A and IgG2 Fc domains. In order to confirm the cleavage site, the IgG Sepharose binding protein fragment was isolated by SDS-PAGE and subjected to N-terminal sequencing. The sequencing data strongly suggested a cleavage site around residues 183 and 184 of the fusion protein and that the protein is in fact cleaved between its FcγR3A and FcG2 domains.

6.4 Characterization of Mutant Proteins Materials and Methods

I. Assay for FcγRIII Binding with BSA-FITC ch-44-20 Immune Complex

A. Generation and Characterization of ch-4-4-20/BSA-FITC Immune Complex:

A chimeric version of the mouse anti-fluorescein monoclonal antibody 4-4-20 (ch-4-4-20) was generated by combining the respective $V_H$ and $V_L$ regions with human IgG1 constant region or human Igk constant regions. The resulting genes were cloned into the expression vector, pCI-neo. The resulting vector was subsequently transfected into HEK293 cells for transient expression of the chimeric antibody which typically accumulated to approximately 5 mg/L in the culture medium. The ch-4-4-20 protein was purified using protein G chromatography followed by size exclusion chromatography. This protein was then used to form an immune complex with FITC-BSA.

The binding of ch-4-4-20 (or a mutant harboring the D265A mutation) to FITC-BSA was performed in ELISA plates; and the same format was used to assess the binding of the chimeric monoclonal antibody to FITC-BSA. FITC-BSA (1 mg/mL-50 ng/well) was coated onto Nunc maxisorb plates in carbonate buffer and allowed to bind for about 16 hours at room temperature. Following blocking with BSA, dilutions of ch 4-4-20 were added to the wells and allowed to bind for an additional hour at room temperature. The unbound monoclonal antibody was removed, and an HRP-conjugated goat anti-human IgG secondary antibody was added. One hour later, the secondary antibody was removed, and the plates were washed and developed with TMB substrate. Following the addition of an acidic stop solution the plate was read at 450 nm. Both ch 4-4-20 and ch-4-4-20 (D265A) bound to the FITC-BSA immune complex with high affinity (data not shown).

B. Assay of Soluble FcγR Binding to ch-4-4-20/FITC-BSA Immune Complexes

FITC-labeled BSA is coated onto MaxiSorp plates. Immune complex is formed by incubating the coated plate with ch 4-4-20. sFcγRIIIA-G2 or mutants thereof bind to the immune complex human IgG1 Fcγ portion. The bound sFcγRIIIA-G2 or mutants thereof are detected with mouse anti-human IgG2 monoclonal antibody.

Nunc F96 MaxiSorp Immunoplate plates were coated with 10 μg/mL BSA-FITC in carbonate buffer and incubated at 4° C. overnight. The plates were blocked with PBS-0.1% Tween-0.5% BSA and incubated for 30' at RT. 1 μg/mLch4-4-20 in PBS/BSA was added to the plates and incubated at room temperature for 1 hr and washed 3× with PBS-T. sFcγRIIIA-G2 or mutants thereof were added at concentrations as indicated in FIG. 2; incubated for 2 hrs at room temperature and washed 3× with PBS-T. anti-huIgG2-Biotin (1:1000) was added and incubated at room temperature for 1 hr, and washed 3× with PBS-T. 50 μL/well of 1:5,000 Streptavidin-HRP in PBS-T/BSA was added to each plate and incubated for 30 min at room temperature and washed 3× with PBS-T. The plate was developed by adding 100 μL/well of TMB reagent and incubated for 5 min at RT in the dark; 50 μL/well of stop solution (0.18 M sulfuric acid) was added to stop the reaction. The plate was read at 450 nM. This assay is schematically represented in FIG. 1 and data for wild type sFcγRIIIA-G2 is provided.

II. Assay for Immune Complex/FcγRIIIA Binding Inhibition by 3G8

FITC labeled BSA was coated on MaxiSorp plate. Immune complex was formed by incubating coated plate with ch4-4-20. 3G8 monoclonal antibody was mixed with sFcγRIIIA-G2 or mutants thereof and the mixture was added to the plate. 3G8 blocks the sFcγRIIIA-G2 or mutants thereof from binding to the human IgG1 Fcγ region in the immune complex. The remaining bound sFcγRIIIA-G2 or mutants thereof are detected by mouse anti-human IgG2 monoclonal antibody. This assay is conducted as described supra, and is exemplified in FIG. 3.

III. Assay for Binding of 3G8 and FcγRIIIA Fusion Proteins

Goat anti human IgG antibody was coated on MaxiSorp plate. sFcγRIIIA-G2 or mutants were captured through their IgG2 Fcγ portion. The captured sFcγRIIIA-G2 or mutants thereof were incubated with the 3G8 monoclonal antibody. The amount of attached 3G8 was detected by goat anti-mouse antibody conjugated with HRP.

Nunc F96 MaxiSorp Immunoplate plates were coated with 2 μg/mL goat anti-human IgG antibody in carbonate buffer and incubated overnight at 4° C. The plates were blocked with PBS-0.1% Tween-0.5% BSA and incubated for 30' at RT. sFcγRIIIA-G2 or mutants thereof in condition medium diluted in PBS/BSA were added to the plates and incubated at room temperature for 1 hr. and washed 3x with PBS-T. 3G8 monoclonal antibody was added to the plate at the indicated concentrations as shown in FIG. 4; Incubated for 1 hr. at room temperature and then washed 3x with PBS-T. Goat anti-mouse antibody conjugated with HRP (1:1000) was added to the plate and incubated at room temperature for 1 hr and then the plate was washed 3x with PBS-T. The plate was developed by adding 100 μL/well of TMB reagent, incubated for 5 min at RT in the dark; 50 μl/well of stop solution (0.18 M sulfuric acid) was added to stop the reaction. The plate was read at 450 nM.

RESULTS

B/C Loop (Trp 110 to Ala 114)

Figure 5:
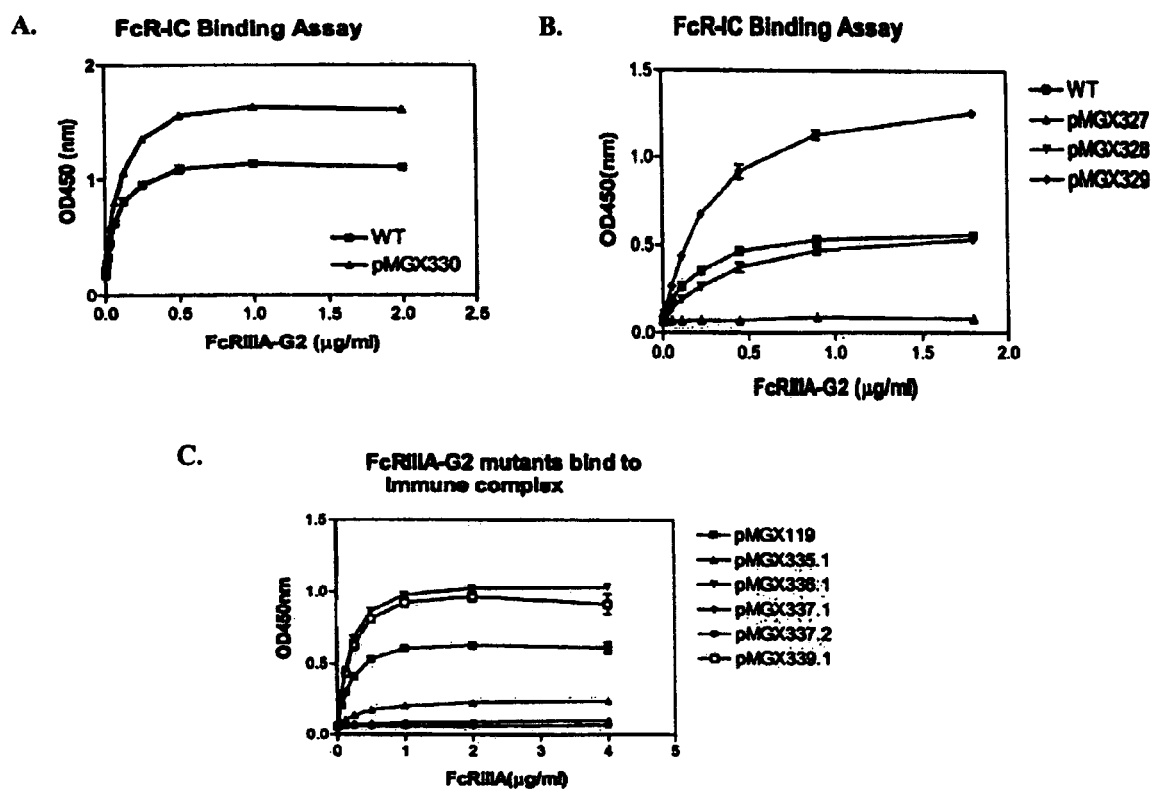
Figure 6:
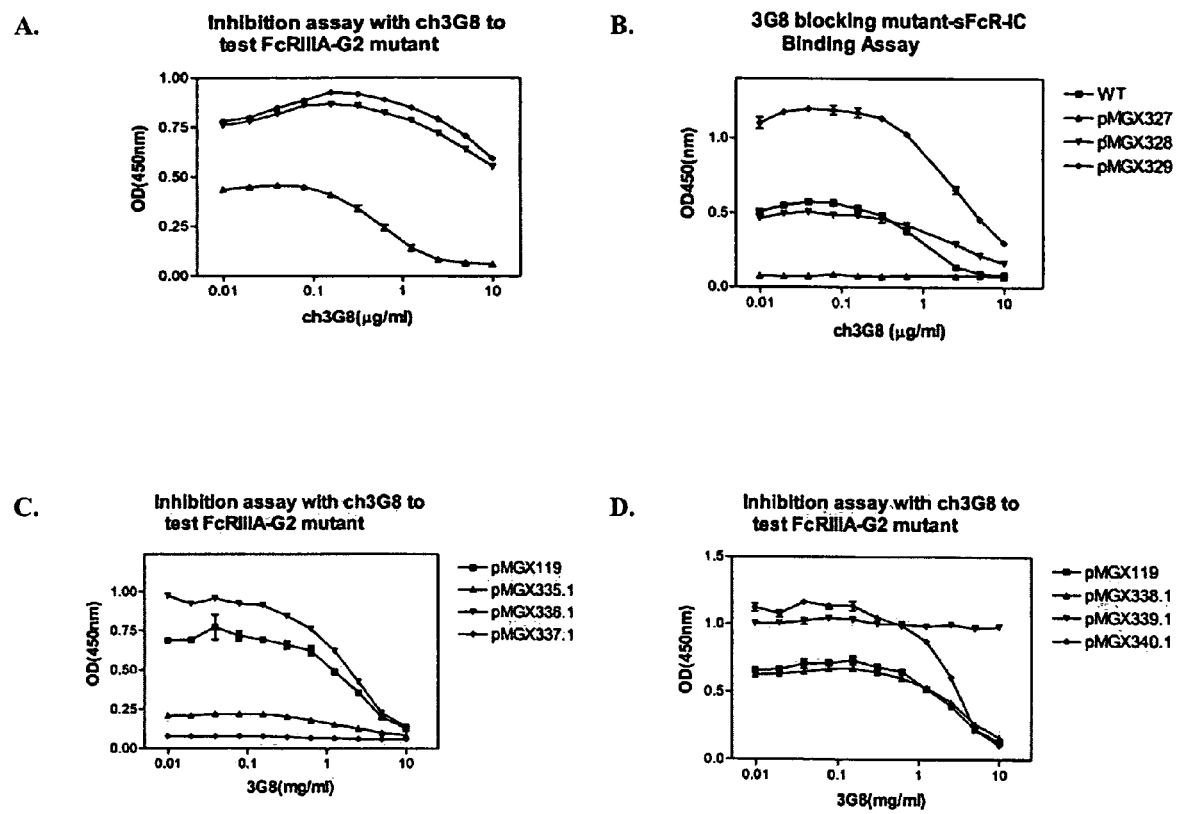
Figure 7:
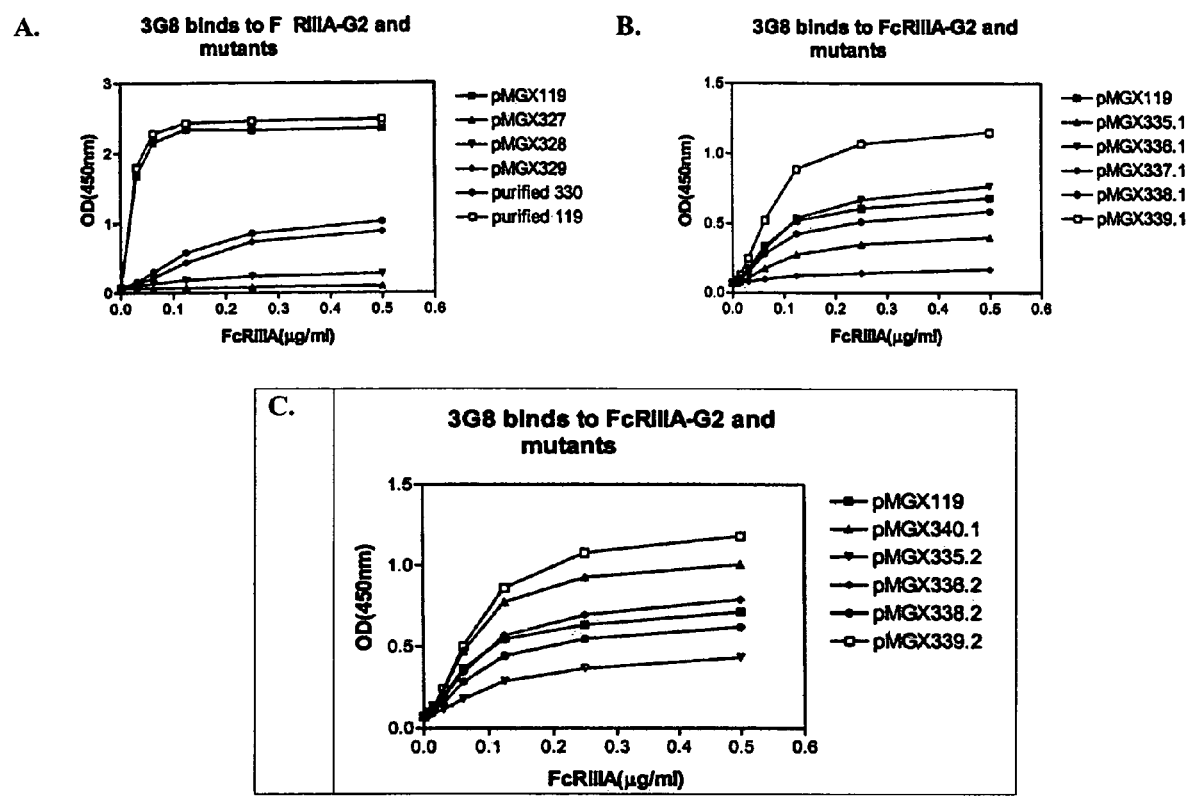

Based on literature, one of the potential 3G8 binding sites is the BC loop (109-114) (Tamm et al.) of FcγRIIIA. Mutant 112NTA114→DKP (pMGX330) retained immune complex binding, as shown in FIG. 5A, however, this mutant had a dramatically decreased 3G8 binding, as shown in FIG. 5B and 5C. However FcγRIIIA mutants with each individual amino acid change (N112D, T113K, A114P) could bind the 3G8 monoclonal antibody as well as FcγRIIIA wild type (FIGS. 5, 6 and 7). These results suggest that the B/C loop (Trp 110 to Ala 114) may not be the 3G8 contact site, but this loop as a whole contributes to 3G8 binding to FcγRIIIA.

C Strand

Mutant H116V lost immune complex binding and retained 3G8 binding (data not shown). This result agrees with the literature in that the C strand is one of the contact sites between Fcγ and FcγRIII.

F/G Loop

Several mutants in this region were constructed, 156GSKNV160 (SEQ ID NO: 43) →GYTLF (SEQ ID NO: 44), V160F, and 154LV155→NI.

156GSKNV160→GYTLF mutant lost both immune complex binding and 3G8 binding. V160F and 154LV155→NI retained immune complex binding but lost 3G8 binding, as shown in FIGS. 5, 6, and 7. V160F was selected as one of the desired candidate for animal study since it has almost no 3G8 binding.

FcγRIIIA and B Variants

V155F mutant dramatically decreased IC binding as well as 3G8 binding (FIGS. 5C, 7B, and 7C).

Y137H has a similar profile as wild type. Mutant G126D abolished receptor function and 3G8 binding. In summary breaking FcγRIIIA G126-Y137-V/F155 pattern at position 126 will cripple FcγRIII's functionality.

In summary, two sFcγRIIIA-G2 mutants were generated (V160F and 112NTA 114→DKP) which lacked 3G8 binding but retained Fcγ binding capacity. They were pursued further for animal studies. Mutant 156GSKNV16043 GYTLF which lacked both immune complex binding and 3G8 binding was also expressed for using in assay development as a negative control.

Table 3 summarizes the mutants that were characterized for immune complex binding as well as 3G8 binding.

TABLE 3

BINDING CHARACTERISTICS AND IMMUNE COMPLEX BINDING OF MUTANTS

|  |  | IC Binding | FcγR inhibited by 3G8 | 3G8 Binding |
|---|---|---|---|---|
| WT | Mutants | +++ | +++ | +++ |
| pMGX327 | 156GSKNV160 --> GYTLF | − | − | − |
| pMGX328 | V160F | +++ | + | − |
| pMGX329 | 154LV155 --> NI | +++++ | ++ | +/− |
| pMGX330 | 112NTA114 --> DKP | +++++ | + | +/− |
| pMGX331 | H116V | − | − | +++ |
| pMGX335 | V155F | + | + | + |
| pMGX336 | Y137H | +++++ | +++ | +++ |
| pMGX337 | G126D | − | − | − |
| pMGX338 | N112D | +++ | +++ | +++ |
| pMGX339 | T113K | +++++ | − | +++++ |
| pMGX340 | A114P | +++++ | ++++ | ++++ |

Stability Results

The construct sFcγRIIIA-G2 was mutagenized in order to generate soluble FcγRIIIA fusion proteins with enhanced stability. The wild type sFcγRIIIA-G2 had limited stability as assessed by SDS-PAGE analysis. In order to improve the stability of the FcγRIIIA-G2 fusion protein, four variants were generated (FIG. 1A). Analytical results suggested that the source of the instability was proteolysis at or near the junction of the FcγR and the Fc segments, which corresponds to amino acids S183-S184. In humans, proteolysis near the C-terminus of the extracellular domain, at residues V196-S197, (Galon et al. 1998, *Eur. J. Immunol.* 28: 2101-7; numbering is in accordance to SEQ ID. NO. 1) has been demonstrated to result in the release of the naturally occuring receptor from cells into a soluble form, see, e.g., Galon et al. 1998, *Eur. J. Immunol.* 28: 2101-7; Fleit et al, 1992, *Blood*, 79: 2721-8; Masuda et al., 2003, *J. Rhematol.* 30(9): 1911-7; Masuda et al., 2003, *Clin. Exp. Immunol.* 132(3): 477-84, all of which are incorporated herein by reference in their entireties. Cell bound FcγRIIB, however, is not subject to such naturally occurring proteolysis in vivo. In two variants of FcγRIIIA-G2, V1 and V2, the C-terminus of the extracellular domain, LAVSTISSFFPPGYQV (SEQ ID NO: 45), was replaced by a flexible GGGGS (SEQ ID NO: 46) linker sequence. In two other variants, V3 and V4, the C-terminus of FcγRIIIA residues ITQGLAVSTISSFFPPGYQV (SEQ ID NO: 47) was replaced by the equivalent segment of FcγRIIB, VQAPSSSPME (SEQ ID NO: 48). An additional difference between FcγRIIIA and FcγRIIB in this region is the presence of an N-linked glycosylation site in FcγRIIIA which is not present in FcγRIIB. Thus, in V1 and V3 the FcγRIIIA sequence at this position was retained while in V2 and V4 the non-glycosylated FcγRIIB sequence was utilized. These subsequences are depicted in FIG. 1A (FcγRIIIA-G2 wild type, SEQ ID NO. 49; V1, SEQ ID NO: 50; V2, SEQ ID NO: 51; V3, SEQ ID NO: 52; V4, SEQ ID NO: 53; and FcγRIIB-G2, SEQ ID NO: 54. These molecules were constructed by an overlapping PCR method and expressed transiently in HEK-293 cells.

The stability of the variant fusion proteins and the original "Wt" FcγRIIIA-G2 molecule was analyzed via SDS-PAGE. Samples were incubated at 25° C. for two months and analyzed by reducing SDS-PAGE at the time zero, one month and two month time points (FIG. 1B). The Wt molecule showed significant breakdown at one month with almost no full length fusion protein remaining at two months. In contrast, all four variants exhibited only a small degree of breakdown after two months at 25° C. with V3 and V4 which are chimeric receptors between RIIIA and RIIB showing the least breakdown.

At time zero, the proteins were for tested their ability to inhibit the binding of labeled monomeric FcgRIIIA to immune complexes in an ELISA assay (FIG. 1C). Each of these variants exhibited increased potency in this assay compared to the original "Wt" fusion protein. The chimeric receptors V3 and V4 were the most potent molecules in this assay, i.e., markedly better at inhibiting monomeric receptor binding compared the the original "Wt" construct. This result was unexpected, since none of the proteins were significantly degraded at this time point.

6.5 Pharmacominetics of Monomeric SFCγRIIB and Dimeric SFCγRIIB-G2-N297Q in BALB/C Mice sFcγRIIB-G2-N297Q (Lot PO 54-069), or sFcγRIIB (Lot PO 54-034) were administered by IV injection into groups of five mice each at a dose of 1 mg/kg (20 µg/mouse). At times 2, 7, 24, 48, and 72 hrs later animals were bled and the level of soluble receptor in the resulting serum determined by a sandwich ELISA assay. The results, shown in Table 4 and FIG. 8, indicate that the dimeric Fc-fusion protein is present in the serum dramatically longer and at much higher concentrations than the monomeric soluble FcγRIIB.

TABLE 4

| | PK Studies | | | | |
|---|---|---|---|---|---|
| | 2 Hr (µg/mL) | 7 Hr (µg/mL) | 24 Hr (µg/mL) | 48 Hr (µg/mL) | 72 Hr (µg/L) |
| sFγcRIIB-G2 N297Q | 12.5 | 10.2 | 7.2 | 3.7 | 3.3 |
| sFcγRIIB-G2 N297Q | 7.2 | 7.2 | 5.0 | 2.9 | 2.2 |
| sFcγRIIB-G2 N297Q | 10.7 | 8.7 | 4.3 | 3.0 | 2.3 |
| sFcγRIIB-G2 N297Q | 11.3 | 8.8 | 3.9 | 3.2 | 2.5 |
| sFcγRIIB-G2 N297Q | 2.1 | 2.4 | 1.7 | 1.4 | 0.9 |
| sFcγRIIB | 0.068 | 0.008 | 0 | 0 | 0 |
| sFcγRIIB | 0.071 | 0.028 | 0 | 0 | 0 |
| sFcγRIIB | 0.142 | 0.030 | 0 | 0 | 0 |
| sFcγRIIB | 0.055 | 0.004 | 0 | 0 | 0 |

6.6 ITP Studies

Materials and Methods

Mice were bled on day 0 and platelet levels were determined. On day one animals were then injected intravenously with either mouse anti-FcγRIIIA monoclonal antibody 3G8 (0.5 mg/kg) or soluble receptor molecules (0.5 mg/kg or 3 mg/kg). One mouse did not receive any compound. One hour later, ITP was induced by administering chimeric 6A6 (ch6A6) to each animal intraperitoneally (i.p.) (0.1 µg/g). Animals were bled 2 hrs, 5 hrs, 24 hrs and 48 hrs after administration of ch6A6 and plasma platelet counts were determined using a particle count and size analyzer Z2 (Coulter) equipped with a 70 µm aperture. Particles between 1.5 and 4 µm in size, corresponding to platelets were counted. Data were analyzed by plotting the relative platelet level (the actual platelet count divided by the time 0 platelet count) versus time for each concentration.

Results

The platelet levels measured in this experiment are shown in FIG. 9. As shown in FIG. 9, all of the animals treated with soluble FcγRIIB-IgG2 constant region fusion proteins (sFcγRIIB-G2) were protected from Ch6A6-mediated platelet depletion. Surprisingly, three of four animals treated with sFcγRIIb-IgG2 exhibited a marked increase in platelet levels two hours after ch6A6 administration and showed no signs of platelet depletion. The fourth animal treated with FcγRIIb-IgG2 exhibited modest depletion which returned to normal at 24 hr. One of the two animals treated with FcγRIIIa-IgG2 was also unaffected by 6A6 administration, while the animal which receive the higher dose of soluble receptor did have reduced platelet counts at 2 hr and 5 hr but was back to normal (d0) levels at 24 hr. In fact, all animals treated with either dimeric soluble FcγR-G2 molecule had normal platelet levels at the 24 hour time point. The platelet levels of the animal treated with the anti-FcγRIII Mab 3G8 also had returned to nearly normal levels 24 hours after injection of the anti-platelet Mab.

Dosing of sFcγRIIIA-G2 in an ITP FcγRIII Knockout Human FcγRIIIA Transgenic Model A group of transgenic mice (FcγRIII knockout human FcγRIIIA transgenic) were treated with ch6A6 to induce ITP. The reduction of platelet depletion resulting from the administration of various doses of sFcγRIIIA-G2 fusion protein was then measured and the protective effect was quantitated graphically as shown in FIG. 10. As shown in FIG. 10, sFcγRIIIA-G2 at 0.75 mg/g and 0.5 ug/g provided the greatest protective effect, and thus the optimal dosing is chosen as 0.5 ug/g.

Use of sFγcRIIIA-G2 in ITP Prevention in mFcγRIIIA−/− hCD32A+ Mice.

Groups of single transgenic (mFcγRIIIA−/− hCD16A+ or mFcγRIIIA−/− hCD32A+) or double transgenic (mFcγRIIIA−/− hCD16A+ hCD32A+) mice were injected i.v. with 0.5 µg/g sFcγRIIIA-G2 on day 0. One hour later, ITP was induced by administering ch6A6 ip (0.1 µg/g). Platelet counts were determined at Day 0 (pre-immunization) as well as 2, 5, 24 and 48 hours post-ch6A6 injection. As shown in FIG. 11, data indicate that both single and double transgenic mice are susceptible to ch6A6-induced ITP. Pre-injection with 0.5 µg/g sFcRγIIIA-G2 prevents the development of ITP in all 3 mice.

Use of sFcγRIIB-G2-N297Q in Therapy Against ITP.

ITP was induced in mFcγRIIIA−/−, hCD16A+ mice by i.p. injection of 0.1 µg/g ch6A6 at time 0. Two hours later, the number of platelets in the plasma was determined to confirm the presence of ITP. Three hours after i.p. injection of ch6A6, mice were injected i.v. with sFcγRIIB-G2-N297Q at different concentrations (arrow). As shown in FIG. 12, data indicate that the number of platelets rapidly returns to normal after sFcγRIIB-G2-N297Q injection whereas the number of platelets remains low in non-treated mice. Treatment of ITP was thus achieved when 0.3 µg/g sFcγRIIB-G2-N297Q was injected 3 hours after ch6A6. Data indicate that sFγcRIIB-G2-N297Q can be used to cure ITP in transgenic mice.

sFγcRIIA-G2-N297Q Does Not Cure mFcγRIIIA−/−, hCD16A+ Mice from ITP.

ITP was induced in mFcγRIIIA−/−, hCD16A+ mice by i.p. injection of 0.1 ug/g ch6A6 at time 0. Two hours later, the number of platelets in the plasma was determined to confirm the presence of ITP. Three hours after i.p. injection of ch6A6, mice were injected i.v. with sFcγRIIA 131H-G2-N297Q or sFcγRIIA131R-G2-N297Q at different concentrations (arrow). Data indicate that the number of platelets remained low after sFcγRIIA-G2-N297Q injection similarly to non-treated mice. As shown in FIG. 13, data indicate that sFcγRIIA-G2-N297Q cannot be used to cure ITP in transgenic mice in the experimental conditions tested.

Use of Combination of sFγcRIIB-G2 N297Q and Anti-hFcγRIIIA Antibodies in Therapy Against ITP.

ITP was induced in mFcγRIIIA−/−, hCD16A+ mice by i.p. injection of 0.1 ug/g ch6A6 at time 0. Two hours later, the number of platelets in the plasma was determined to confirm the presence of ITP. Three hours after i.p. injection of ch6A6, mice were injected i.v. with sFcγRIIB-G2-N297Q or anti-hFcγRIIIA 5.1 N297Q and 22.1 N297Q antibodies at different concentrations (arrow). The "low" concentration does not cure ITP in these experimental conditions whereas the "high" concentration does.

In the same experiment, additional mice were injected 3 hours after ch6A6 with combination of sFcγRIIB-G2 N297Q and either 5.1 N297Q or 22.1 N297Q at low concentrations. Data indicate that although low concentration (0.2 ug/g) of sFcγRIIB-G2 N297Q does not cure mFcγRIIIA−/−, hCD16A+ mice from ITP. Combination of low concentration (0.2 ug/g) of sFcγRIIB-G2 N297Q and low concentration (0.125 ug/g) of anti-FcγRIIIA antibodies cures mice from ITP. Data indicate that sFcγRIIB-G2 N297Q and 5.1 N297Q or 22.1 N297Q can be used in combination therapy of ITP. (FIGS. 14A-C)

Use of sFcγRIIIA-G2 in ITP Prevention in mFcγRIIIA−/− hCD32A+ Mice.

ITP was induced groups of single transgenic (mFcγRIIIA−/− hCD32A+, FIG. 15) or double transgenic (mFcγRIIIA−/− hCD16A+ hCD32A+, FIG. 14) mice by i.p. injection of 0.1 ug/g ch6A6 at time 0. Two hours later, the number of platelets in the plasma was determined to confirm the presence of ITP. Three hours later, mice were injected i.v. with 0.5 µg/g sFcγRIIB-G2 N297Q (arrow). Data indicate that 0.5 µg/g sFcγRIIB-G2 N297Q cures mice expressing the human CD32A transgene.

6.7 Autoimmune Hemolytic Anemia (AHA)

AHA Prevention in muFcγRIII−/−, huFcγRIIIA Transgenic Mice using sFcγRIIB-G2-N297Q mFcγRIIIA−/− hCD16A+ transgenic mice were injected i.v. with 5 µg/g or 7.6 µg/g sFcγRIIB-G2-N297Q on day 0. Three hours later, AHA was induced by administering a pathogenic anti-mouse red blood cells (RBC) antibody (34-3C, see, e.g., Pottier et al., 1996, *Clin. Exp. Immunol.* 106(1): 103-7, which is incorporated herein by reference in its entirety) ip (50 µg/mouse). RBC counts were determined at Day 0 (pre-immunization) as well as at days 1, 2, 3, 4, and 7 post-34-3C injection. As shown in FIG. 16, data indicate that mFcγRIIA−/− hCD16A+ transgenic mice are susceptible to 34-3C-induced AHA. Data also indicate that the number of RBC remains stable in mice injected with sFcγRIIB-G2-N297Q whereas the number of RBC drops in non-treated mice. In this model, the number of RBC returns to normal in all mice at day 7. Control mice are bled every day but not injected in order to determine the effect of repeated bleedings on the number of RBC. Pre-injection with sFcγRIIB-G2-N297Q prevents the development of AHA muFcγRIII−/−, huFcγRIIIA transgenic mice.

What is claimed is:

1. An isolated polypeptide, comprising the amino acid sequence of SEQ ID No 42.

2. A dimeric fusion protein comprising two identical polypeptide chains, each chain comprising the amino acid sequence of SEQ ID No. 42.

3. A pharmaceutical composition comprising a therapeutically effective amount of the polypeptide of claim 1, and a pharmaceutically acceptable carrier.

4. A pharmaceutical composition comprising a therapeutically effective amount of the dimeric fusion protein of claim 2, and a pharmaceutically acceptable carrier.

* * * * *